US011786557B2

(12) United States Patent
Dudakov et al.

(10) Patent No.: US 11,786,557 B2
(45) Date of Patent: Oct. 17, 2023

(54) LUTEINIZING HORMONE RECEPTOR BINDING AGENTS AND LUTEINIZING HORMONE AGONISTS TO IDENTIFY, EXPAND, ABLATE AND MODIFY STEM CELLS

(71) Applicants: Fred Hutchinson Cancer Center, Seattle, WA (US); Memorial Sloan Kettering Cancer Center, New York, NY (US)

(72) Inventors: Jarrod Dudakov, Seattle, WA (US); Marcel van den Brink, New York, NY (US); Enrico Velardi, New York, NY (US); Hans-Peter Kiem, Seattle, WA (US); Stefan Radtke, Seattle, WA (US); Scott James, New York, NY (US)

(73) Assignee: Fred Hutchinson Cancer Center, Seattle, WA (US)

( * ) Notice: Subject to any disclaimer, the term of this patent is extended or adjusted under 35 U.S.C. 154(b) by 620 days.

(21) Appl. No.: 16/753,277

(22) PCT Filed: Oct. 2, 2018

(86) PCT No.: PCT/US2018/054004
§ 371 (c)(1),
(2) Date: Apr. 2, 2020

(87) PCT Pub. No.: WO2019/070740
PCT Pub. Date: Apr. 11, 2019

(65) Prior Publication Data
US 2020/0237827 A1 Jul. 30, 2020

Related U.S. Application Data

(60) Provisional application No. 62/566,897, filed on Oct. 2, 2017.

(51) Int. Cl.
*A61K 35/28* (2015.01)
*A61P 35/00* (2006.01)
*C12N 5/0789* (2010.01)
*C12N 15/86* (2006.01)
*A61K 35/12* (2015.01)

(52) U.S. Cl.
CPC .............. *A61K 35/28* (2013.01); *A61K 35/12* (2013.01); *A61P 35/00* (2018.01); *C12N 5/0647* (2013.01); *C12N 15/86* (2013.01)

(58) Field of Classification Search
None
See application file for complete search history.

(56) References Cited

U.S. PATENT DOCUMENTS 5,444,167 A 8/1995 Pettersson
6,919,209 B1 7/2005 Chatterjee et al.

2002/0127652 A1 9/2002 Schambye et al.
2003/0219786 A1 11/2003 Tayar et al.
2005/0020524 A1 1/2005 Boyd
2014/0348744 A1 11/2014 Pinski
2015/0037296 A1 2/2015 Denaro et al.
2015/0266973 A1 9/2015 Jarjour et al.
2017/0226176 A1 8/2017 Perales-Puchalt et al.

FOREIGN PATENT DOCUMENTS

WO WO9814592 A2 4/1998
WO WO03028711 A2 4/2003
WO WO2005115304 A2 12/2005
WO WO2016094880 6/2016
WO WO2016118780 7/2016
WO WO2016160618 A2 10/2016

OTHER PUBLICATIONS

Akritopoulou-Zanze, et al., "Synthesis and biological evaluation of 5-substituted 1,4-dihydroindeno[1,2-c]pyrazoles as multitargeted receptor tyrosine kinase inhibitors," Bioorganic & Medicinal Chemistry Letters, vol. 17, No. 11, 2007, pp. 3136-3140.
Anno, et al., "Dose Response Relationships for Acute Ionizing-Radiation Lethality," Health Physics, vol. 84, No. 5, 2003, pp. 565-575.
Broxmeyer, et al., "HLA-DR human histocompatibility leukocyte antigens-restricted lymphocyte-monocyte interactions in the release from monocytes of acidic isoferritins that suppress hematopoietic progenitor cells.," Journal of Clinical Investigation, vol. 73, No. 4, 1984, pp. 939-953.
Chen, et al., "TSC-mTOR maintains quiescence and function of hematopoietic stem cells by repressing mitochondrial biogenesis and reactive oxygen species," J. Exp. Med., vol. 205, No. 10, 2008, pp. 2397-2408.
Cheng, et al., "Hematopoietic Stem Cell Quiescence Maintained by p21cip1/waf1," Science, vol. 287, No. 5459, 2000, pp. 1804-1808.
Choi & Smitz, "Luteinizing hormone and human chorionic gonadotropin: Origins of difference," Molecular and Cellular Endocrinology, vol. 383, No. 1-2, 2014, pp. 203-213.
Chow, et al., "The tyrosine kinase inhibitor AMN107 (Nilotinib) exhibits off-target effects in lymphoblastic cell lines," Leukemia & Lymphoma, vol. 48, No. 7, 2007, pp. 1379-1388.
Craddock, et al., "Antibodies to VLA4 integrin mobilize long-term repopulating cells and augment cytokine-induced mobilization in primates and mice," Blood, vol. 90, No. 12, 1997, pp. 4779-4788.

(Continued)

Primary Examiner — Russell G Fiebig
(74) Attorney, Agent, or Firm — Lee & Hayes PC; C. Rachal Winger

(57) ABSTRACT

The use of luteinizing hormone receptor (LHR) binding agents and luteinizing hormone (LH) agonists to enrich for primitive hematopoietic stem cell (pHSC) populations, to target pHSC for ablation, and/or to expand pHSC populations are described. The methods can be used to prepare therapeutic hematopoietic stem cell (HSC) populations, to prepare patients for therapeutic HSC transplants, and/or to treat malignancies, such as those associated with hyperproliferative HSC.

19 Claims, 29 Drawing Sheets
Specification includes a Sequence Listing.

(56) References Cited

OTHER PUBLICATIONS

Dainiak, Nicholas, "Hematologic consequences of exposure to ionizing radiation," Experimental Hematology, vol. 30, No. 6, 2002, pp. 513-528.
Davies and Metzger, "Structural basis of antibody function," Annual Review of Immunology, vol. 1, 1983, pp. 87-117.
Delic, et al., "Leydig cell function in the pubertal rat following local testicular irradiation," Radiother. Oncol., vol. 5, No. 1, 1986, pp. 29-37.
Delic, et al., "Serum androgen binding protein and follicle stimulating hormone as indices of Sertoli cell function in the irradiated testis.," British Journal of Cancer, vol. 53, Suppl. 7, 1986, pp. 105-107.
Doan, et al., "Epidermal growth factor regulates hematopoietic regeneration after radiation injury," Nature Medicine, vol. 19, No. 3, 2013, pp. 295-304.
Drouet & Herodin, "Radiation victim management and the haematologist in the future: time to revisit therapeutic guidelines?," International Journal of Radiation Biology, vol. 86, No. 8, 2010, pp. 636-648.
Dudakov, et al., "Sex Steroid Ablation Enhances Hematopoietic Recovery following Cytotoxic Antineoplastic Therapy in Aged Mice," Journal of Immunology, vol. 183, No. 11, 2009, pp. 7084-7094.
Dudakov, et al., "Withdrawal of Sex Steroids Reverses Age- and Chemotherapy-Related Defects in Bone Marrow Lymphopoiesis," Journal of Immunology, vol. 182, No. 10, 2009, pp. 6247-6260.
Esser, et al., "IFNalpha activates dormant haematopoietic stem cells in vivo," Nature, vol. 458, 2009, pp. 904-908.
Goldberg, et al., "Sex Steroid Ablation Enhances Immune Reconstitution Following Cytotoxic Antineoplastic Therapy in Young Mice," Journal of Immunology, vol. 184, No. 11, 2010, pp. 6014-6024.
Hai, et al., "Infertility in Female Mice with a Gain-of-Function Mutation in the Luteinizing Hormone Receptor is Due to Irregular Estrous Cyclicity, Anovulation, Hormonal Alterations, and Polycystic Ovaries," Biology of Reproduction, vol. 93, No. 1, 2015, pp. 1-11.
Heng, et al., "The Immunological Genome Project: networks of gene expression in immune cells," Nature Immunology, vol. 9, No. 10, 2008, pp. 1091-1094.
Herodin & Drouet, "Cytokine-based treatment of accidentally irradiated victims and new approaches," Experimental Hematology, vol. 33, No. 10, 2005, pp. 1071-1080.
Himburg, et al., "Pleiotrophin mediates hematopoietic regeneration via activation of RAS," Journal of Clinical Investigation, vol. 124, No. 11, 2014, pp. 4753-4758.
Huntsman, et al., "Human hematopoietic stem cells from mobilized peripheral blood can be purified based on CD49f Integrin expression," Blood, vol. 126, No. 13, 2015, pp. 1631-1633.
Itoh, et al., "Reproducible establishment of hemopoietic supportive stromal cell lines from murine bone marrow," Exp. Hematology, vol. 17, No. 2, 1989, pp. 145-153.
Jin, et al., "Differentiation of two types of mobilized peripheral blood stem cells by microRNA and cDNA expression analysis," Journal of Translational Medicine, vol. 6, No. 39, 2008, 12 pages.
Jo, et al., "Chemotaxis of primitive hematopoietic cells in response to stromal cell-derived factor-1," Journal of Clinical Investigation, vol. 105, No. 1, 2000, pp. 101-111.
Johnson, et al., "Mitigation of hematologic radiation toxicity in mice through pharmacological quiescence induced by CDK4/6 inhibition," Journal of Clinical Investigation, vol. 120, No. 7, 2010, pp. 2528-2536.
Kharas & Gritsman, "Akt: A double-edged sword for hematopoietic stem cells" Cell Cycle, vol. 9, No. 7, 2010, pp. 1223-1224.
Kharas, et al., "Constitutively active AKT depletes hematopoietic stem cells and induces leukemia in mice," Blood, vol. 115, No. 7, 2010, pp. 1406-1415.
Khong, et al., "Enhanced Hematopoietic Stem Cell Function Mediates Immune Regeneration following Sex Steroid Blockade," Stem Cell Reports, vol. 4, No. 3, 2015, pp. 445-458.
Kodo, et al., "Antibody synthesis by bone marrow cells in vitro following primary and booster tetanus toxoid Immunization in humans," Journal of Clinical Investigation, vol. 73, No. 5, 1984, pp. 1377-1384.
Koukourakis, "Radiation damage and radioprotectants: new concepts in the era of molecular medicine," British Institute of Radiology, vol. 85, 2012, pp. 313-330.
Lazebnik, et al., "Cleavage of poly(ADP-ribose) polymerase by a proteinase with properties like Ice," Nature, vol. 371, 1994, pp. 346-347.
Lei, et al., "Targeted disruption of luteinizing hormone/human chorionic gonadotropin receptor gene," Mol. Endocrinol., vol. 15, No. 1, 2001, pp. 184-200.
Luo, et al., "Superovulation strategies for 6 commonly used mouse strains" J. Am. Assoc. Lab. Anim. Sci., vol. 50, No. 4, 2011, pp. 471-478.
Mak, et al., "Male pheromone-stimulated neurogenesis in the adult female brain: possible role in mating behavior.," Nature Neuroscience, vol. 10, No. 8, 2007, pp. 1003-1011.
McGee & Narayan, "Precocious Puberty and Leydig Cell Hyperplasia in Male Mice With a Gain of Function Mutation in the LH Receptor Gene," Endocrinology, vol. 154, No. 10, 2013, pp. 3900-3913.
Meistrich, Marvin, "Male gonadal toxicity," Pediatric Blood & Cancer, vol. 53, No. 2, 2009, pp. 261-266.
Mierzejewska, et al., "Hematopoietic Stem/Progenitor Cells Express Several Functional Sex Hormone Receptors—Novel Evidence for a Potential Developmental Link Between Hematopoiesis and Primordial Germ Cells," Stem Cells and Development, vol. 24, No. 8, 2015, pp. 927-937.
Nakada, et al., "Oestrogen increases haematopoietic stem-cell self-renewal in females and during pregnancy," Nature, Mol. 505, No. 7484, 2014, pp. 555-558.
Notta, et al., "Isolation of Single Human Hematopoietic Stem Cells Capable of Long-Term Multilineage Engraftment," Science, vol. 333, No. 6039, 2011, pp. 218-221.
Opferman, et al., "Obligate Role of Anti-Apoptotic MCL-1 in the Survival of Hematopoietic Stem Cells," Science, vol. 307, No. 5712, 2005, pp. 1101-1104.
Papayannopoulou, et al., "Anti-VLA4/VCAM-1-induced mobilization requires cooperative signaling through the kit/mkit ligand pathway," Blood, vol. 91, No. 7, 1998, pp. 2231-2239.
Pelus, Louis, "Peripheral blood stem cell mobilization: new regimens, new cells, where do we stand," Curr. Opin. Hematol., vol. 15, No. 4, 2008, pp. 285-292.
Qing, et al., "Bcl2 overexpression rescues the hematopoietic stem cell defects in Ku7O-deficient mice by restoration of quiescence," Blood, vol. 123, No. 7, 2014, pp. 1002-1011.
Radtke, et al., "The frequency of multipotent CD133+CD45RA—CD34+ hematopoietic stem cells is not increased in fetal liver compared with adult stem cell sources," Experimental Hematology, vol. 44, No. 6, 2016, pp. 502-507.
Randall & Weissman, "Phenotypic and functional changes induced at the clonal level in hematopoietic stem cells after 5-fluorouracil treatment," Blood, vol. 89, No. 10, 1997, pp. 3596-3606.
Rashid, et al., "Comparison of GK1.5 and chimeric rat/mouse GK1.5 anti-CD4 antibodies for prolongation of skin allograft survival and suppression of alloantibody production in mice," Journal of Immunology, vol. 148, No. 5, 1992, pp. 1382-1388.
Reisner, et al., "Allogeneic hemopoietic stem cell transplantation using mouse spleen cells fractionated by lectins: in vitro study of cell fractions," PNAS USA, vol. 77, No. 2, 1980, pp. 1164-1168.
Sanchez-Aguilera, et al., "Estrogen Signaling Selectively Induces Apoptosis of Hematopoietic Progenitors and Myeloid Neoplasms without Harming Steady-State Hematopoiesis," Cell Stem Cell, vol. 15, No. 6, 2014, pp. 791-804.
Seita, et al., "Gene Expression Commons: An Open Platform for Absolute Gene Expression Profiling," PLoS One, vol. 7, No. 7, 2012, 11 pages.
Shalet, et al., "Vulnerability of the human Leydig cell to radiation damage is dependent upon age," Journal of Endocrinology, vol. 120, No. 1, 1989, pp. 161-165.

(56) References Cited

OTHER PUBLICATIONS

Shiraishi & Ascoli, "Lutropin/Choriogonadotropin Stimulate the Proliferation of Primary Cultures of Rat Leydig Cells through a Pathway that Involves Activation of the Extracellularly Regulated Kinase 1/2 Cascade," Endocrinology, vol. 148, No. 7, 2007, pp. 3214-3225.
Singh & Yadav, "Role of cytokines and growth factors in radioprotection," Experimental and Molecular Pathology, vol. 78, No. 2, 2005, pp. 156-169.
Thurmond, et al., "Role of Estrogen Receptor alpha in Hematopoietic Stem Cell Development and B Lymphocyte Maturation in the Male Mouse," Endocrinology, vol. 141, No. 7, 2000, pp. 2309-2318.
Tricot, et al., "Mobilization of peripheral blood stem cells in myeloma with either pegfilgrastim or filgrastim following chemotherapy," Haematologica, vol. 93, No. 11, 2008, pp. 1739-1742.
Tsai, et al., "Nrf2 regulates haematopoietic stem cell function," Nature Cell Biology, vol. 15, No. 3, 2013, pp. 309-316.
Velardi, et al., "Sex steroid blockade enhances thymopoiesis by modulating Notch signaling," Journal of Experimental Medicine, vol. 211, No. 12, 2014, pp. 2341-2349.
Wang, et al., "Fine-tuning p53 activity through C-terminal modification significantly contributes to HSC homeostasis and mouse radiosensitivity," Genes & Development, vol. 25, 2011, pp. 1426-1438.
Wang, et al., "Total body irradiation selectively induces murine hematopoietic stem cell senescence," Blood, vol. 107, No. 1, 2006, pp. 358-366.
Weaver, et al., "Mobilization of peripheral blood stem cells following myelosuppressive chemotherapy: a randomized comparison of filgrastim, sargramostim, or sequential sargramostim and filgrastim," Bone Marrow Transplantation, vol. 27, Suppl. 2, 2001, pp. S23-S29.
Williams, et al., "Animal Models for Medical Countermeasures to Radiation Exposure," Radiation Research, vol. 173, No. 4, 2010, pp. 557-578.
Williams, et al., "Pluripotential hematopoietic stem cells in post-5-fluorouracil murine bone marrow express the Thy-1 antigen," Journal of Immunology, vol. 135, No. 2, 1985, pp. 1004-1011.
Yu, et al., "HES1 Inhibits Cycling of Hematopoietic Progenitor Cells via DNA Binding," Stem Cells, vol. 24, No. 4, 2006, pp. 876-888.
Zhang, et al., "Normal prenatal but arrested postnatal sexual development of luteinizing hormone receptor knockout (LuRKO) mice," Mol Endocrinol., vol. 15, No. 1, 2001, pp. 172-183.
Zsebo, et al., "Radioprotection of mice by recombinant rat stem cell factor," PNAS USA, vol. 89, No. 20, 1992, pp. 9464-9468.
Abdelbaset-Ismail, et al, "Human Haematopoietic stem/progenitor cells express several functional sex hormone receptors," J. Cell Mol. Med., vol. 20, No. 1, 2016, pp. 134-146.
Invitation to Pay dated Jan. 25, 2019 for International Application No. PCT/US2018/054004, 3 pages.
Majeti, et al, "Identification of a Hierarchy of Multipotent Hematopoietic Progenitors in Human Cord Blood," Cell Stem Cell, vol. 1, No. 6, Cell Press, 2007, pp. 635-645.
Naldini, "A Comeback for Gene Therapy," Science, vol. 326, 2009, 3 pages.
Search Report and Written Opinion dated Mar. 22, 2019 for International Application No. PCT/US18/54004, 22 pages.
Tatesu, et al, "A Novel Approach in Expanding CD34+CD90+ and CD34+CD38+CD90+ Cells Associated with Enhanced in Vivo Repopulating Potential," Blood, vol. 120, No. 21, 2012, pp. 1-3.
Urbanska, et al, "Follicle-stimulating hormone receptor as a target in the redirected T-cell therapy for Cancer," Cancer Immunol. Res., vol. 3, No. 10, 2015, pp. 1130-1137.
Extended European Search Report dated May 19, 2021, for European Application No. 18864802.6, 8 pages.
Meduri, et al., "Luteinizing Hormone/Human Chorionic Gonadotropin Receptors in Breast Cancer," Cancer Research, 1997, pp. 857-864.
Parrott et al., "Expression and actions of both the follicle stimulating hormone receptor and the luteinizing hormone receptor in normal ovarian surface epithelium and ovarian cancer," Mol. Cell. Endocrinol., vol. 172, No. 1-2, 2001, pp. 213-222.

FIG. 5A

| Population | Phenotype |
|---|---|
| LT-HSC | Lin⁻Sca1⁺ckit⁺CD150⁺CD48⁻Flt3⁻ |
| ST-HSC | Lin⁻Sca1⁺ckit⁺CD150⁻CD48⁻Flt3⁻ |
| MPP | Lin⁻Sca1⁺ckit⁺CD150⁻CD48⁻Flt3⁺ |
| MP | Lin⁻Sca1⁻ckit⁺ |
| CMP | Lin⁻Sca1⁻ckit⁺CD150⁻CD34⁺FcγR$^{lo}$ |
| Pre-MEP | Lin⁻Sca1⁻ckit⁺CD150⁺CD34⁺FcγR$^{lo}$ |
| MEP | Lin⁻Sca1⁻ckit⁺CD34⁻FcγR⁻CD150⁻ |
| Megakaryocyte | CD45⁺TER119⁻CD41⁺CD61⁺ |
| Macrophage | CD45⁺TER119⁻CD11b⁺Gr1⁻ |
| MSC | CD45⁻TER119⁻PDGFRα⁺CD51⁺CD31⁻ |
| EC | CD45⁻TER119⁻PDGFRα⁻CD51⁻CD31⁺ |
| Osteoblast | CD45⁻TER119⁻PDGFRα⁻CD51⁺CD31⁻ |

FIG. 5B

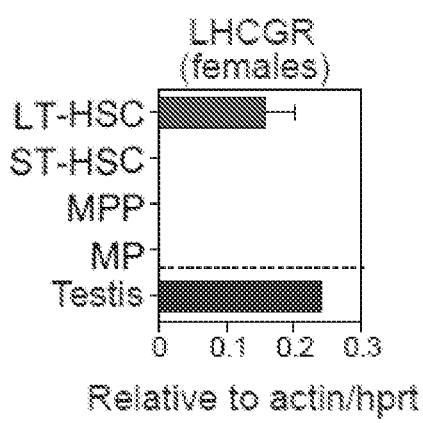

Mouse LH-CAR design

Human LH-CAR design

Mouse LH-CAR design

Human LH-CAR design

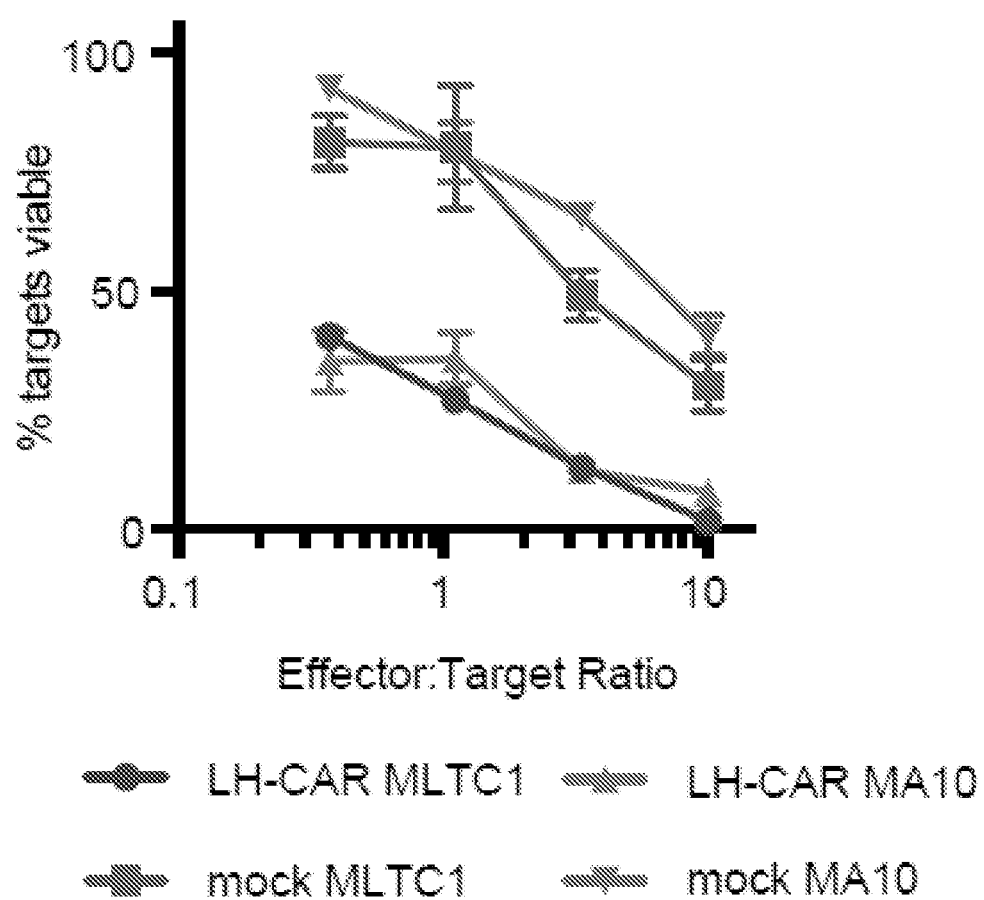

FIG. 11

Luteinizing hormone receptor [Homo sapiens]

MKQRFSALQLLKLLLLLQPPLPRALREALCPEPCNCVPDGALRCPGPTAGLTRLSLAYL
PVKVIPSQAFRGLNEVIKIEISQIDSLERIEANAFDNLLNLSEILIQNTKNLRYIEPGAFINLP
RLKYLSICNTGIRKFPDVTKVFSSESNFILEICDNLHITTIPGNAFQGMNNESVTLKLYGN
GFEEVQSHAFNGTTLTSLELKENVHLEKMHNGAFRGATGPKTLDISSTKLQALPSYGL
ESIQRLIATSSYSLKKLPSRETFVNLLEATLTYPSHCCAFRNLPTKEQNFSHSISENFSK
QCESTVRKVNNKTLYSSMLAESELSGWDYEYGFCLPKTPRCAPEPDAFNPCEDIMGY
DFLRVLIWLINILAIMGNMTVLFVLLTSRYKLTVPRFLMCNLSFADFCMGLYLLLIASVDS
QTKGQYYNHAIDWQTGSGCSTAGFFTVFASELSVYTLTVITLERWHTITYAIHLDQKLR
LRHAILIMLGGWLFSSLIAMLPLVGVSNYMKVSICFPMDVETTLSQVYILTILILNVVAFFII
CACYIKIYFAVRNPELMATNKDTKIAKKMAILIFTDFTCMAPISFFAISAAFKVPLITVTNSK
VLLVLFYPINSCANPFLYAIFTKTFQRDFFLLLSKFGCCKRRAELYRRKDFSAYTSNCKN
GFTGSNKPSQSTLKLSTLHCQGTALLDKTRYTEC (SEQ ID NO: 1)

Luteinizing hormone receptor [Mus musculus]

MGRRVPALRQLLVLAMLVLKQSQLHSPELSGSRCPEPCDCAPDGALRCPGPRAGLA
RLSLTYLPVKVIPSQAFRGLNEVVKIEISQSDSLERIEANAFDNLLNLSEILIQNTKNLLYIE
PGAFTNLPRLKYLSICNTGIRTLPDVSKISSSEFNFILEICDNLYITTIPGNAFQGMNNESI
TLKLYGNGFEEVQSHAFNGTTLISLELKENIYLEKMHSGTFQGATGPSILDVSSTKLQAL
PSHGLESIQTLIATSSYSLKTLPSREKFTSLLVATLTYPSHCCAFRNLPKKEQNFSFSIFE
NFSKQCESTVREANNETLYSAIFEENELSGWDYDYDFCSPKTLQCTPEPDAFNPCEDI
MGYAFLRVLIWLINILAIFGNLTVLFVLLTSRYKLTVPRFLMCNLSFADFCMGLYLLLIASV
DSQTKGQYYNHAIDWQTGSGCSAAGFFTVFASELSVYTLTVITLERWHTITYAVQLDQ
KLRLRHAIPIMLGGWIFSTLMATLPLVGVSSYMKVSICLPMDVESTLSQVYILSILLLNAV
AFVVICACYVRIYFAVQNPELTAPNKDTKIAKKMAILIFTDFTCMAPISFFAISAAFKVPLIT
VTNSKVLLVLFYPVNSCANPFLYAVFTKAFQRDFFLLLSRFGCCKHRAELYRRKEFSAC
TFNSKNGFPRSSKPSQAALKLSIVHCQQPTPPRVLIQ (SEQ ID NO: 2)

Luteinizing hormone receptor [Rattus norvegicus]

MGRRVPALRQLLVLAVLLLKPSQLQSRELSGSRCPEPCDCAPDGALRCPGPRAGLAR
LSLTYLPVKVIPSQAFRGLNEVVKIEISQSDSLERIEANAFDNLLNLSELLIQNTKNLLYIE
PGAFTNLPRLKYLSICNTGIRTLPDVTKISSSEFNFILEICDNLHITTIPGNAFQGMNNESV
TLKLYGNGFEEVQSHAFNGTTLISLELKENIYLEKMHSGAFQGATGPSILDISSTKLQAL
PSHGLESIQTLIALSSYSLKTLPSKEKFTSLLVATLTYPSHCCAFRNLPKKEQNFSFSIFE
NFSKQCESTVRKADNETLYSAIFEENELSGWDYDYGFCSPKTLQCAPEPDAFNPCEDI
MGYAFLRVLIWLINILAIFGNLTVLFVLLTSRYKLTVPRFLMCNLSFADFCMGLYLLLIASV
DSQTKGQYYNHAIDWQTGSGCGAAGFFTVFASELSVYTLTVITLERWHTITYAVQLDQ
KLRLRHAIPIMLGGWLFSTLIATMPLVGISNYMKVSICLPMDVESTLSQVYILSILILNVVA
FVVICACYIRIYFAVQNPELTAPNKDTKIAKKMAILIFTDFTCMAPISFFAISAAFKVPLITV
TNSKILLVLFYPVNSCANPFLYAIFTKAFQRDFLLLLSRFGCCKRRAELYRRKEFSAYTS
NCKNGFPGASKPSQATLKLSTVHCQQPIPPRALTH (SEQ ID NO: 3)

FIG. 12

Variant of CD3ζ and a portion of the 4-1BB intracellular signaling domain

4-1BB

```
DNA: AAACGGGGCAGAAAGAAACTCCTGTATATATTCAAACAACCATTTATG
 AA: K   R   G   R   K   K   L   L   Y   I   F   K   Q   P   F   M

DNA: AGACCAGTACAAACTACTCAAGAGGAAGATGGCTGTAGCTGCCGATTTCCA
 AA: R   P   V   Q   T   T   Q   E   E   D   G   C   S   C   R   F   P
                                                              CD3Zeta
DNA: GAAGAAGAAGAAGGAGGATGTGAACTGCGGGTGAAG:TTCAGCAGAAGCGCC
 AA: E   E   E   E   G   G   C   E   L   R   V   K   F   S   R   S   A DNA: GACGCCCTGCCTACCAGCAGGGCCAGAATCAGCTGTACAACGAGCTGAAC
 AA: D   A   P   A   Y   Q   Q   G   Q   N   Q   L   Y   N   E   L   N DNA: CTGGGCAGAAGGGAAGAGTACGACGTCCTGGATAAGCGGAGAGGCCGGGAC
 AA: L   G   R   R   E   E   Y   D   V   L   D   K   R   R   G   R   D DNA: CCTGAGATGGGCGGCAAGCCTCGGCGGAAGAACCCCCAGGAAGGCCTGTAT
 AA: P   E   M   G   G   K   P   R   R   K   N   P   Q   E   G   L   Y DNA: AACGAACTGCAGAAAGACAAGATGGCCGAGGCCTACAGCGAGATCGGCATG
 AA: N   E   L   Q   K   D   K   M   A   E   A   Y   S   E   I   G   M DNA: AAGGGCGAGCGGAGGCGGGGCAAGGGCCACGACGGCCTGTATCAGGGCCTG
 AA: K   G   E   R   R   R   G   K   G   H   D   G   L   Y   Q   G   L

DNA: TCCACCGCCACCAAGGATACCTACGACGCCCTGCACATGCAGGCCCTGCCC

AA: S   T   A   T   K   D   T   Y   D   A   L   H   M   Q   A   L   P

DNA: CCAAGG (SEQ ID NO: 4)

AA: P   R (SEQ ID NO: 5)
```

FIG. 13A

Mouse LH-CAR cDNA (CD28 CD3z format):

ATGGCCTCACCGTTGACCCGCTTTCTGTCGCTGAACCTGCTGCTGCTGGGTGAGT
CGATTATCCTGGGGAGTGGAGAAGCTTCCAGGGGCCCCCTTCGGCCACTGTGCC
GGCCTGTCAACGCAACTCTGGCCGCAGAGAATGAGTTCTGCCCAGTCTGCATCAC
CTTCACCACCAGCATCTGTGCCGGCTACTGTCCTAGCATGGTCCGAGTACTGCCG
GCTGCTTTGCCTCCTGTGCCTCAGCCAGTGTGCACCTACCGGGAGCTGCGCTTCG
CATCTGTCCGCCTCCCTGGCTGCCCACCGGGTGTAGACCCCATAGTCTCCTTTCC
TGTAGCCCTCAGCTGCCGCTGTGGGCCCTGCCGGCTCAGTAGCTCTGACTGTGG
GGGTCCCAGGACTCAACCAATGGCCTGTGACCTCCCCACCTCCCCGGCCTCCTC
CTCCTCGGTGGAGGTGGATCAGGTGGAGGTGGATCTGGTGGAGGTGGATCTTC
CTGATGGAGACTTTATTATTCAGGGTTGCCCAGAATGTAAACTAAAGGAAAATAAAT
ACTTCTCCAAGCTAGGAGCCCCCATCTACCAGTGTATGGGCTGTTGCTTCTCCAGG
GCATATCCCACTCCTGCCAGGTCCAAGAAGACAATGCTGGTTCCAAAGAATATTAC
CTCGGAGGCCACATGCTGTGTGGCCAAAGCATTTACTAAGGCCACAGTAATGGGA
AATGCCAGAGTGGAGAATCATACGGAGTGCCACTGTAGCACTTGCTACTACCACAA
GTCGGAACAAAAACTCATCTCAGAAGAGGATCTGGCGGCCGCATCTACTACTACC
AAGCCAGTGCTGCGAACTCCCTCACCTGTGCACCCTACCGGGACATCTCAGCCCC
AGAGACCAGAAGATTGTCGGCCCCGTGGCTCAGTGAAGGGGACCGGATTGGACT
TCGCCTGTGATATTTACATCTGGGCACCCTTGGCCGGAATCTGCGTGGCCCTTCTG
CTGTCCTTGATCATCACTCTCATCTGCTACAATAGTAGAAGGAACAGACTCCTTCAA
AGTGACTACATGAACATGACTCCCCGGAGGCCTGGGCTCACTCGAAAGCCTTACC
AGCCCTACGCCCTGCCAGAGACTTTGCAGCGTACCGCCCCAGAGCAAAATTCAG
CAGGAGTGCAGAGACTGCTGCCAACCTGCAGGACCCCAACCAGCTCTACAATGAG
CTCAATCTAGGGCGAAGAGAGGAATATGACGTCTTGGAGAAGAAGCGGGCTCGG
GATCCAGAGATGGGAGGCAAACAGCAGAGGAGGAGGAACCCCCAGGAAGGCGTA
TACAATGCACTGCAGAAAGACAAGATGGCAGAAGCCTACAGTGAGATCGGCACAA
AAGGCGAGAGGCGGAGAGGCAAGGGGCACGATGGCCTTTACCAGGGTCTCAGCA
CTGCCACCAAGGACACCTATGATGCCCTGCATATGCAGACCCTGGCCCCTCGCGG
TACCGGTCAATGTACTAACTACGCTTTGTTGAAACTCGCTGGCGATGTTGAAAGTA
ACCCCGGTCCTGGATCCATGAACCCAGCCATCAGCGTCGCTCTCCTGCTCTCAGT
CTTGCAGGTGTCCCGAGGGCAGAAGGTGACCAGCCTGACAGCCTGCCTGGTGAA
CCAAAACCTTCGCCTGGACTGCCGCCATGAGAATAACACCAAGGATAACTCCATCC
AGCATGAGTTCAGCCTGACCCGAGAGAAGAGGAAGCACGTGCTCTCAGGCACCCT
CGGGATACCCGAGCACACGTACCGCTCCCGCGTCACCCTCTCCAACCAGCCCTAT
ATCAAGGTCCTTACCCTAGCCAACTTCACCACCAAGGATGAGGCGACTACTTTTG
TGAGCTTCGAGTCTCGGGCGCGAATCCATGAGCTCCAATAAAGTATCAGTGTGT
ATAGAGACAAACTGGTCAAGTGTGGCGGCATAAGCCTGCTGGTTCAGAACACATC
CTGGATGCTGCTGCTGCTGCTTTCCCTCTCCCTCCTCCAAGCCCTGGACTTCATTT
CTCTG (SEQ ID NO: 6)

FIG. 13A (cont'd)

Mouse LH-CAR Translation:

MASPLTRFLSLNLLLLGESIILGSGEASRGPLRPLCRPVNATLAAENEFCPVCITFTTSICAGYC
PSMVRVLPAALPPVPQPVCTYRELRFASVRLPGCPPGVDPIVSFPVALSCRCGPCRLSSSDC
GGPRTQPMACDLPHLPGLLLLGGGGSGGGGSGGGGSLPDGDFIIQGCPECKLKENKYFSKL
GAPIYQCMGCCFSRAYPTPARSKKTMLVPKNITSEATCCVAKAFTKATVMGNARVENHTECH
CSTCYYHKSEQKLISEEDLAAASTTTKPVLRTPSPVHPTGTSQPQRPEDCRPRGSVKGTGLD
FACDIYIWAPLAGICVALLLSLIITLICYNSRRNRLLQSDYMNMTPRRPGLTRKPYQPYAPARDF
AAYRPRAKFSRSAETAANLQDPNQLYNELNLGRREEYDVLEKKRARDPEMGGKQQRRRNP
QEGVYNALQKDKMAEAYSEIGTKGERRRGKGHDGLYQGLSTATKDTYDALHMQTLAPRGTG
QCTNYALLKLAGDVESNPGPGSMNPAISVALLLSVLQVSRGQKVTSLTACLVNQNLRLDCRH
ENNTKDNSIQHEFSLTREKRKHVLSGTLGIPEHTYRSRVTLSNQPYIKVLTLANFTTKDEGDYF
CELRVSGANPMSSNKSISVYRDKLVKCGGISLLVQNTSWMLLLLLSLSLLQALDFISL (SEQ ID
NO: 7)

Mouse LH-CAR Translation Subcomponents:

Signal Peptide: MASPLTRFLSLNLLLLGESIILGSGEA (SEQ ID NO: 8)

LH beta subunit: SRGPLRPLCRPVNATLAAENEFCPVCITFTTSICAGYCPSMVRVLPAALPP
VPQPVCTYRELRFASVRLPGCPPGVDPIVSFPVALSCRCGPCRLSSSDCGGPRTQPMACDL
PHLPGLLLL (SEQ ID NO: 9)

Linker: GGGGSGGGGSGGGGS (SEQ ID NO: 10)

LH alpha subunit: LPDGDFIIQGCPECKLKENKYFSKLGAPIYQCMGCCFSRAYPTPARSKK
TMLVPKNITSEATCCVAKAFTKATVMGNARVENHTECHCSTCYYHKS (SEQ ID NO: 11)

Myc: EQKLISEEDL (SEQ ID NO: 12)

CD8 Hinge: STTTKPVLRTPSPVHPTGTSQPQRPEDCRPRGSVKGTGLDFACD (SEQ ID NO: 13)

CD8 Transmembrane Domain: IYIWAPLAGICVALLLSLIITLICY (SEQ ID NO: 14)

CD28 Cytoplasmic: NSRRNRLLQSDYMNMTPRRPGLTRKPYQPYAPARDFAAYRP (SEQ ID NO: 15)

CD3 zeta:
RAKFSRSAETAANLQDPNQLYNELNLGRREEYDVLEKKRARDPEMGGKQQRRRNPQEGVY
NALQKDKMAEAYSEIGTKGERRRGKGHDGLYQGLSTATKDTYDALHMQTLAPR (SEQ ID NO: 16)

E2A: QCTNYALLKLAGDVESNPGP (SEQ ID NO: 17)

Thy1.1:MNPAISVALLLSVLQVSRGQKVTSLTACLVNQNLRLDCRHENNTKDNSIQHEFSLTRE
KRKHVLSGTLGIPEHTYRSRVTLSNQPYIKVLTLANFTTKDEGDYFCELRVSGANPMSSNKSIS
VYRDKLVKCGGISLLVQNTSWMLLLLLSLSLLQALDFISL (SEQ ID NO: 18)

FIG. 13B

Human LH-CAR cDNA (4-1BB CD3z format)

ATGGAGACAGACACACTCCTGCTATGGGTGCTGCTGCTCTGGGTTCCAGGTTCCA
CAGGTTCCAGGGAGCCGCTTCGGCCATGGTGCCACCCCATCAATGCCATCCTGGC
TGTCGAGAAGGAGGGCTGCCCAGTGTGCATCACCGTCAACACCACCATCTGTGCC
GGCTACTGCCCCACCATGATGCGCGTGCTGCAGGCGGTCCTGCCGCCCTGCCT
CAGGTGGTGTGCACCTACCGTGATGTGCGCTTCGAGTCCATCCGGCTCCCTGGCT
GCCCGCGTGGTGTGGACCCCGTGGTCTCCTTCCCTGTGGCTCTCAGCTGTCGCTG
TGGACCCTGCCGCCGCAGCACCTCTGACTGTGGGGGTCCCAAAGACCACCCCTT
GACCTGTGACCACCCCAACTCTCAGGCCTCCTCTTCCTCGGTGGAGGTGGATCA
GGTGGAGGTGGATCTGGTGGAGGTGGATCTGCTCCTGATGTGCAGGATTGCCCA
GAATGCACGCTACAGGAAAACCCATTCTTCTCCCAGCCGGGTGCCCCAATACTTCA
GTGCATGGGCTGCTGCTTCTCTAGAGCATATCCCACTCCACTAAGGTCCAAGAAGA
CGATGTTGGTCCAAAAGAACGTCACCTCAGAGTCCACTTGCTGTGTAGCTAAATCA
TATAACAGGGTCACAGTAATGGGGGGTTTCAAAGTGGAGAACCACACGGCGTGCC
ACTGCAGTACTTGTTATTATCACAAATCTGAACAAAAACTCATCTCAGAAGAGGATC
TGGCGGCCGCAATTGAAGTTATGTATCCTCCTCCTTACCTAGACAATGAGAAGAGC
AATGGAACCATTATCCATGTGAAAGGGAAACACCTTTGTCCAAGTCCCCTATTTCC
CGGACCTTCTAAGCCCTTCTGGGTGCTGGTGGTGGTGGGCGGGGTGCTGGCCTG
CTACAGCCTGCTGGTGACAGTGGCCTTCATCATCTTTTGGGTGAAACGGGGCAGA
AAGAAACTCCTGTATATATTCAAACAACCATTTATGAGACCAGTACAAACTACTCAA
GAGGAAGATGGCTGTAGCTGCCGATTTCCAGAAGAAGAAGAAGGAGGATGTGAAC
TGCGGGTGAAGTTCAGCAGAAGCGCCGACGCCCCTGCCTACCAGCAGGGCCAGA
ATCAGCTGTACAACGAGCTGAACCTGGGCAGAAGGGAAGAGTACGACGTCCTGGA
TAAGCGGAGAGGCCGGGACCCTGAGATGGGCGGCAAGCCTCGGCGGAAGAACC
CCCAGGAAGGCCTGTATAACGAACTGCAGAAAGACAAGATGGCCGAGGCCTACAG
CGAGATCGGCATGAAGGGCGAGCGGAGGCGGGGCAAGGGCCACGACGGCCTGT
ATCAGGGCCTGTCCACCGCCACCAAGGATACCTACGACGCCCTGCACATGCAGGC
CCTGCCCCCAAGG (SEQ ID NO: 19)

FIG. 13B (cont'd)

Human LH-CAR Translation:

METDTLLLWVLLLWVPGSTGSREPLRPWCHPINAILAVEKEGCPVCITVNTTICAGYCP
TMMRVLQAVLPPLPQVVCTYRDVRFESIRLPGCPRGVDPVVSFPVALSCRCGPCRRS
TSDCGGPKDHPLTCDHPQLSGLLFLGGGGSGGGGSGGGGSAPDVQDCPECTLQEN
PFFSQPGAPILQCMGCCFSRAYPTPLRSKKTMLVQKNVTSESTCCVAKSYNRVTVMG
GFKVENHTACHCSTCYYHKSEQKLISEEDLAAAIEVMYPPPYLDNEKSNGTIIHVKGKH
LCPSPLFPGPSKPFWVLVVVGGVLACYSLLVTVAFIIFWVKRGRKKLLYIFKQPFMRPV
QTTQEEDGCSCRFPEEEEGGCELRVKFSRSADAPAYQQGQNQLYNELNLGRREEYD
VLDKRRGRDPEMGGKPRRKNPQEGLYNELQKDKMAEAYSEIGMKGERRRGKGHDG
LYQGLSTATKDTYDALHMQALPPR (SEQ ID NO: 20)

Human LH-CAR Translation Subcomponents:

Signal Peptide: METDTLLLWVLLLWVPGSTG (SEQ ID NO: 21)

LH beta subunit: SREPLRPWCHPINAILAVEKEGCPVCITVNTTICAGYCPTMMRVLQA
VLPPLPQVVCTYRDVRFESIRLPGCPRGVDPVVSFPVALSCRCGPCRRSTSDCGGPK
DHPLTCDHPQLSGLLFL (SEQ ID NO: 22)

Linker: GGGGSGGGGSGGGGS (SEQ ID NO: 10)

LH alpha subunit: APDVQDCPECTLQENPFFSQPGAPILQCMGCCFSRAYPTPLRSKK
TMLVQKNVTSESTCCVAKSYNRVTVMGGFKVENHTACHCSTCYYHKS (SEQ ID NO: 23)

Myc: EQKLISEEDL (SEQ ID NO: 12)

CD28 Hinge: IEVMYPPPYLDNEKSNGTIIHVKGKHLCPSPLFPGPSKP (SEQ ID NO: 24)

CD28 Transmembrane Domain: FWVLVVVGGVLACYSLLVTVAFIIFWV (SEQ ID NO: 25)

4-1BB: KRGRKKLLYIFKQPFMRPVQTTQEEDGCSCRFPEEEEGGCEL (SEQ ID NO: 26)

CD3 zeta: RVKFSRSADAPAYQQGQNQLYNELNLGRREEYDVLDKRRGRDPEMG
GKPRRKNPQEGLYNELQKDKMAEAYSEIGMKGERRRGKGHDGLYQGLSTATKDTYD
ALHMQALPPR (SEQ ID NO: 27)

SEQUENCE LISTING

<160> NUMBER OF SEQ ID NOS: 90

<210> SEQ ID NO 1
<211> LENGTH: 699
<212> TYPE: PRT
<213> ORGANISM: Homo sapiens

<400> SEQUENCE: 1

Met Lys Gln Arg Phe Ser Ala Leu Gln Leu Leu Lys Leu Leu Leu Leu

-continued

```
1               5                   10                  15
Leu Gln Pro Pro Leu Pro Arg Ala Leu Arg Glu Ala Leu Cys Pro Glu
                20                  25                  30

Pro Cys Asn Cys Val Pro Asp Gly Ala Leu Arg Cys Pro Gly Pro Thr
                35                  40                  45

Ala Gly Leu Thr Arg Leu Ser Leu Ala Tyr Leu Pro Val Lys Val Ile
        50                  55                  60

Pro Ser Gln Ala Phe Arg Gly Leu Asn Glu Val Ile Lys Ile Glu Ile
65                  70                  75                  80

Ser Gln Ile Asp Ser Leu Glu Arg Ile Glu Ala Asn Ala Phe Asp Asn
                85                  90                  95

Leu Leu Asn Leu Ser Glu Ile Leu Ile Gln Asn Thr Lys Asn Leu Arg
                100                 105                 110

Tyr Ile Glu Pro Gly Ala Phe Ile Asn Leu Pro Arg Leu Lys Tyr Leu
                115                 120                 125

Ser Ile Cys Asn Thr Gly Ile Arg Lys Phe Pro Asp Val Thr Lys Val
                130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
                180                 185                 190

Ala Phe Asn Gly Thr Thr Leu Thr Ser Leu Glu Leu Lys Glu Asn Val
                195                 200                 205

His Leu Glu Lys Met His Asn Gly Ala Phe Arg Gly Ala Thr Gly Pro
                210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
                260                 265                 270

Leu Thr Tyr Pro Ser His Cys Cys Ala Phe Arg Asn Leu Pro Thr Lys
                275                 280                 285

Glu Gln Asn Phe Ser His Ser Ile Ser Glu Asn Phe Ser Lys Gln Cys
                290                 295                 300

Glu Ser Thr Val Arg Lys Val Asn Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335

Leu Pro Lys Thr Pro Arg Cys Ala Pro Glu Pro Asp Ala Phe Asn Pro
                340                 345                 350

Cys Glu Asp Ile Met Gly Tyr Asp Phe Leu Arg Val Leu Ile Trp Leu
                355                 360                 365

Ile Asn Ile Leu Ala Ile Met Gly Asn Met Thr Val Leu Phe Val Leu
                370                 375                 380

Leu Thr Ser Arg Tyr Lys Leu Thr Val Pro Arg Phe Leu Met Cys Asn
385                 390                 395                 400

Leu Ser Phe Ala Asp Phe Cys Met Gly Leu Tyr Leu Leu Leu Ile Ala
                405                 410                 415

Ser Val Asp Ser Gln Thr Lys Gly Gln Tyr Tyr Asn His Ala Ile Asp
                420                 425                 430
```

-continued

Trp Gln Thr Gly Ser Gly Cys Ser Thr Ala Gly Phe Phe Thr Val Phe
            435                 440                 445

Ala Ser Glu Leu Ser Val Tyr Thr Leu Thr Val Ile Thr Leu Glu Arg
    450                 455                 460

Trp His Thr Ile Thr Tyr Ala Ile His Leu Asp Gln Lys Leu Arg Leu
465                 470                 475                 480

Arg His Ala Ile Leu Ile Met Leu Gly Gly Trp Leu Phe Ser Ser Leu
                485                 490                 495

Ile Ala Met Leu Pro Leu Val Gly Val Ser Asn Tyr Met Lys Val Ser
            500                 505                 510

Ile Cys Phe Pro Met Asp Val Glu Thr Thr Leu Ser Gln Val Tyr Ile
        515                 520                 525

Leu Thr Ile Leu Ile Leu Asn Val Val Ala Phe Phe Ile Ile Cys Ala
    530                 535                 540

Cys Tyr Ile Lys Ile Tyr Phe Ala Val Arg Asn Pro Glu Leu Met Ala
545                 550                 555                 560

Thr Asn Lys Asp Thr Lys Ile Ala Lys Lys Met Ala Ile Leu Ile Phe
                565                 570                 575

Thr Asp Phe Thr Cys Met Ala Pro Ile Ser Phe Phe Ala Ile Ser Ala
            580                 585                 590

Ala Phe Lys Val Pro Leu Ile Thr Val Thr Asn Ser Lys Val Leu Leu
        595                 600                 605

Val Leu Phe Tyr Pro Ile Asn Ser Cys Ala Asn Pro Phe Leu Tyr Ala
    610                 615                 620

Ile Phe Thr Lys Thr Phe Gln Arg Asp Phe Leu Leu Leu Ser Lys
625                 630                 635                 640

Phe Gly Cys Cys Lys Arg Arg Ala Glu Leu Tyr Arg Arg Lys Asp Phe
                645                 650                 655

Ser Ala Tyr Thr Ser Asn Cys Lys Asn Gly Phe Thr Gly Ser Asn Lys
            660                 665                 670

Pro Ser Gln Ser Thr Leu Lys Leu Ser Thr Leu His Cys Gln Gly Thr
        675                 680                 685

Ala Leu Leu Asp Lys Thr Arg Tyr Thr Glu Cys
    690                 695

<210> SEQ ID NO 2
<211> LENGTH: 700
<212> TYPE: PRT
<213> ORGANISM: Mus musculus

<400> SEQUENCE: 2

Met Gly Arg Arg Val Pro Ala Leu Arg Gln Leu Leu Val Leu Ala Met
1               5                   10                  15

Leu Val Leu Lys Gln Ser Gln Leu His Ser Pro Glu Leu Ser Gly Ser
            20                  25                  30

Arg Cys Pro Glu Pro Cys Asp Cys Ala Pro Asp Gly Ala Leu Arg Cys
        35                  40                  45

Pro Gly Pro Arg Ala Gly Leu Ala Arg Leu Ser Leu Thr Tyr Leu Pro
    50                  55                  60

Val Lys Val Ile Pro Ser Gln Ala Phe Arg Gly Leu Asn Glu Val Val
65                  70                  75                  80

Lys Ile Glu Ile Ser Gln Ser Asp Ser Leu Glu Arg Ile Glu Ala Asn
                85                  90                  95

Ala Phe Asp Asn Leu Leu Asn Leu Ser Glu Ile Leu Ile Gln Asn Thr

```
            100                 105                 110
Lys Asn Leu Leu Tyr Ile Glu Pro Gly Ala Phe Thr Asn Leu Pro Arg
        115                 120                 125

Leu Lys Tyr Leu Ser Ile Cys Asn Thr Gly Ile Arg Thr Leu Pro Asp
    130                 135                 140

Val Ser Lys Ile Ser Ser Ser Glu Phe Asn Phe Ile Leu Glu Ile Cys
145                 150                 155                 160

Asp Asn Leu Tyr Ile Thr Thr Ile Pro Gly Asn Ala Phe Gln Gly Met
                165                 170                 175

Asn Asn Glu Ser Ile Thr Leu Lys Leu Tyr Gly Asn Gly Phe Glu Glu
            180                 185                 190

Val Gln Ser His Ala Phe Asn Gly Thr Thr Leu Ile Ser Leu Glu Leu
        195                 200                 205

Lys Glu Asn Ile Tyr Leu Glu Lys Met His Ser Gly Thr Phe Gln Gly
    210                 215                 220

Ala Thr Gly Pro Ser Ile Leu Asp Val Ser Ser Thr Lys Leu Gln Ala
225                 230                 235                 240

Leu Pro Ser His Gly Leu Glu Ser Ile Gln Thr Leu Ile Ala Thr Ser
                245                 250                 255

Ser Tyr Ser Leu Lys Thr Leu Pro Ser Arg Glu Lys Phe Thr Ser Leu
            260                 265                 270

Leu Val Ala Thr Leu Thr Tyr Pro Ser His Cys Cys Ala Phe Arg Asn
        275                 280                 285

Leu Pro Lys Lys Glu Gln Asn Phe Ser Phe Ser Ile Phe Glu Asn Phe
    290                 295                 300

Ser Lys Gln Cys Glu Ser Thr Val Arg Glu Ala Asn Asn Glu Thr Leu
305                 310                 315                 320

Tyr Ser Ala Ile Phe Glu Glu Asn Glu Leu Ser Gly Trp Asp Tyr Asp
                325                 330                 335

Tyr Asp Phe Cys Ser Pro Lys Thr Leu Gln Cys Thr Pro Glu Pro Asp
            340                 345                 350

Ala Phe Asn Pro Cys Glu Asp Ile Met Gly Tyr Ala Phe Leu Arg Val
        355                 360                 365

Leu Ile Trp Leu Ile Asn Ile Leu Ala Ile Phe Gly Asn Leu Thr Val
    370                 375                 380

Leu Phe Val Leu Leu Thr Ser Arg Tyr Lys Leu Thr Val Pro Arg Phe
385                 390                 395                 400

Leu Met Cys Asn Leu Ser Phe Ala Asp Phe Cys Met Gly Leu Tyr Leu
                405                 410                 415

Leu Leu Ile Ala Ser Val Asp Ser Gln Thr Lys Gly Gln Tyr Tyr Asn
            420                 425                 430

His Ala Ile Asp Trp Gln Thr Gly Ser Gly Cys Ser Ala Ala Gly Phe
        435                 440                 445

Phe Thr Val Phe Ala Ser Glu Leu Ser Val Tyr Thr Leu Thr Val Ile
    450                 455                 460

Thr Leu Glu Arg Trp His Thr Ile Thr Tyr Ala Val Gln Leu Asp Gln
465                 470                 475                 480

Lys Leu Arg Leu Arg His Ala Ile Pro Ile Met Leu Gly Gly Trp Ile
                485                 490                 495

Phe Ser Thr Leu Met Ala Thr Leu Pro Leu Val Gly Val Ser Ser Tyr
            500                 505                 510

Met Lys Val Ser Ile Cys Leu Pro Met Asp Val Glu Ser Thr Leu Ser
        515                 520                 525
```

```
Gln Val Tyr Ile Leu Ser Ile Leu Leu Asn Ala Val Ala Phe Val
            530                 535                 540

Val Ile Cys Ala Cys Tyr Val Arg Ile Tyr Phe Ala Val Gln Asn Pro
545                 550                 555                 560

Glu Leu Thr Ala Pro Asn Lys Asp Thr Lys Ile Ala Lys Lys Met Ala
                565                 570                 575

Ile Leu Ile Phe Thr Asp Phe Thr Cys Met Ala Pro Ile Ser Phe Phe
            580                 585                 590

Ala Ile Ser Ala Ala Phe Lys Val Pro Leu Ile Thr Val Thr Asn Ser
        595                 600                 605

Lys Val Leu Leu Val Leu Phe Tyr Pro Val Asn Ser Cys Ala Asn Pro
610                 615                 620

Phe Leu Tyr Ala Val Phe Thr Lys Ala Phe Gln Arg Asp Phe Phe Leu
625                 630                 635                 640

Leu Leu Ser Arg Phe Gly Cys Cys Lys His Arg Ala Glu Leu Tyr Arg
                645                 650                 655

Arg Lys Glu Phe Ser Ala Cys Thr Phe Asn Ser Lys Asn Gly Phe Pro
            660                 665                 670

Arg Ser Ser Lys Pro Ser Gln Ala Ala Leu Lys Leu Ser Ile Val His
        675                 680                 685

Cys Gln Gln Pro Thr Pro Pro Arg Val Leu Ile Gln
690                 695                 700

<210> SEQ ID NO 3
<211> LENGTH: 700
<212> TYPE: PRT
<213> ORGANISM: Rattus norvegicus

<400> SEQUENCE: 3

Met Gly Arg Arg Val Pro Ala Leu Arg Gln Leu Leu Val Leu Ala Val
1               5                   10                  15

Leu Leu Leu Lys Pro Ser Gln Leu Gln Ser Arg Glu Leu Ser Gly Ser
            20                  25                  30

Arg Cys Pro Glu Pro Cys Asp Cys Ala Pro Asp Gly Ala Leu Arg Cys
        35                  40                  45

Pro Gly Pro Arg Ala Gly Leu Ala Arg Leu Ser Leu Thr Tyr Leu Pro
    50                  55                  60

Val Lys Val Ile Pro Ser Gln Ala Phe Arg Gly Leu Asn Glu Val Val
65                  70                  75                  80

Lys Ile Glu Ile Ser Gln Ser Asp Ser Leu Glu Arg Ile Glu Ala Asn
                85                  90                  95

Ala Phe Asp Asn Leu Leu Asn Leu Ser Glu Leu Leu Ile Gln Asn Thr
            100                 105                 110

Lys Asn Leu Leu Tyr Ile Glu Pro Gly Ala Phe Thr Asn Leu Pro Arg
        115                 120                 125

Leu Lys Tyr Leu Ser Ile Cys Asn Thr Gly Ile Arg Thr Leu Pro Asp
    130                 135                 140

Val Thr Lys Ile Ser Ser Ser Glu Phe Asn Phe Ile Leu Glu Ile Cys
145                 150                 155                 160

Asp Asn Leu His Ile Thr Thr Ile Pro Gly Asn Ala Phe Gln Gly Met
                165                 170                 175

Asn Asn Glu Ser Val Thr Leu Lys Leu Tyr Gly Asn Gly Phe Glu Glu
            180                 185                 190

Val Gln Ser His Ala Phe Asn Gly Thr Thr Leu Ile Ser Leu Glu Leu
```

```
            195                 200                 205
Lys Glu Asn Ile Tyr Leu Glu Lys Met His Ser Gly Ala Phe Gln Gly
    210                 215                 220

Ala Thr Gly Pro Ser Ile Leu Asp Ile Ser Ser Thr Lys Leu Gln Ala
225                 230                 235                 240

Leu Pro Ser His Gly Leu Glu Ser Ile Gln Thr Leu Ile Ala Leu Ser
                245                 250                 255

Ser Tyr Ser Leu Lys Thr Leu Pro Ser Lys Glu Lys Phe Thr Ser Leu
            260                 265                 270

Leu Val Ala Thr Leu Thr Tyr Pro Ser His Cys Cys Ala Phe Arg Asn
        275                 280                 285

Leu Pro Lys Lys Glu Gln Asn Phe Ser Phe Ser Ile Phe Glu Asn Phe
290                 295                 300

Ser Lys Gln Cys Glu Ser Thr Val Arg Lys Ala Asp Asn Glu Thr Leu
305                 310                 315                 320

Tyr Ser Ala Ile Phe Glu Glu Asn Glu Leu Ser Gly Trp Asp Tyr Asp
                325                 330                 335

Tyr Gly Phe Cys Ser Pro Lys Thr Leu Gln Cys Ala Pro Glu Pro Asp
            340                 345                 350

Ala Phe Asn Pro Cys Glu Asp Ile Met Gly Tyr Ala Phe Leu Arg Val
        355                 360                 365

Leu Ile Trp Leu Ile Asn Ile Leu Ala Ile Phe Gly Asn Leu Thr Val
370                 375                 380

Leu Phe Val Leu Leu Thr Ser Arg Tyr Lys Leu Thr Val Pro Arg Phe
385                 390                 395                 400

Leu Met Cys Asn Leu Ser Phe Ala Asp Phe Cys Met Gly Leu Tyr Leu
                405                 410                 415

Leu Leu Ile Ala Ser Val Asp Ser Gln Thr Lys Gly Gln Tyr Tyr Asn
            420                 425                 430

His Ala Ile Asp Trp Gln Thr Gly Ser Gly Cys Gly Ala Ala Gly Phe
        435                 440                 445

Phe Thr Val Phe Ala Ser Glu Leu Ser Val Tyr Thr Leu Thr Val Ile
450                 455                 460

Thr Leu Glu Arg Trp His Thr Ile Thr Tyr Ala Val Gln Leu Asp Gln
465                 470                 475                 480

Lys Leu Arg Leu Arg His Ala Ile Pro Ile Met Leu Gly Gly Trp Leu
                485                 490                 495

Phe Ser Thr Leu Ile Ala Thr Met Pro Leu Val Gly Ile Ser Asn Tyr
            500                 505                 510

Met Lys Val Ser Ile Cys Leu Pro Met Asp Val Glu Ser Thr Leu Ser
        515                 520                 525

Gln Val Tyr Ile Leu Ser Ile Leu Leu Asn Val Ala Phe Val
530                 535                 540

Val Ile Cys Ala Cys Tyr Ile Arg Ile Tyr Phe Ala Val Gln Asn Pro
545                 550                 555                 560

Glu Leu Thr Ala Pro Asn Lys Asp Thr Lys Ile Ala Lys Lys Met Ala
                565                 570                 575

Ile Leu Ile Phe Thr Asp Phe Thr Cys Met Ala Pro Ile Ser Phe Phe
            580                 585                 590

Ala Ile Ser Ala Ala Phe Lys Val Pro Leu Ile Thr Val Thr Asn Ser
        595                 600                 605

Lys Ile Leu Leu Val Leu Phe Tyr Pro Val Asn Ser Cys Ala Asn Pro
610                 615                 620
```

```
Phe Leu Tyr Ala Ile Phe Thr Lys Ala Phe Gln Arg Asp Phe Leu Leu
625                 630                 635                 640

Leu Leu Ser Arg Phe Gly Cys Cys Lys Arg Arg Ala Glu Leu Tyr Arg
            645                 650                 655

Arg Lys Glu Phe Ser Ala Tyr Thr Ser Asn Cys Lys Asn Gly Phe Pro
            660                 665                 670

Gly Ala Ser Lys Pro Ser Gln Ala Thr Leu Lys Leu Ser Thr Val His
        675                 680                 685

Cys Gln Gln Pro Ile Pro Pro Arg Ala Leu Thr His
    690                 695                 700

<210> SEQ ID NO 4
<211> LENGTH: 462
<212> TYPE: DNA
<213> ORGANISM: Artificial Sequence
<220> FEATURE:
<223> OTHER INFORMATION: Variant of CD3zeta and a portion of the 4-1BB
      intracellular signaling domain

<400> SEQUENCE: 4
aaacggggca gaaagaaact cctgtatata ttcaaacaac catttatgag accagtacaa        60
actactcaag aggaagatgg ctgtagctgc cgatttccag aagaagaaga aggaggatgt       120
gaactgcggg tgaagttcag cagaagcgcc gacgccgcctg cctaccagca gggccagaat     180
cagctgtaca acgagctgaa cctgggcaga agggaagagt acgacgtcct ggataagcgg      240
agaggccggg accctgagat gggcggcaag cctcggcgga agaaccccca ggaaggcctg      300
tataacgaac tgcagaaaga caagatggcc gaggcctaca gcgagatcgg catgaagggc     360
gagcggaggc ggggcaaggg ccacgacggc ctgtatcagg gcctgtccac cgccaccaag     420 gataccctacg acgccctgca catgcaggcc ctgcccccaa gg                       462

<210> SEQ ID NO 5
<211> LENGTH: 154
<212> TYPE: PRT
<213> ORGANISM: Artificial Sequence
<220> FEATURE:
<223> OTHER INFORMATION: Variant of CD3zeta and a portion of the 4-1BB
      intracellular signaling domain

<400> SEQUENCE: 5

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Arg Val Lys Phe Ser Arg
        35                  40                  45

Ser Ala Asp Ala Pro Ala Tyr Gln Gln Gly Gln Asn Gln Leu Tyr Asn
    50                  55                  60

Glu Leu Asn Leu Gly Arg Arg Glu Glu Tyr Asp Val Leu Asp Lys Arg
65                  70                  75                  80

Arg Gly Arg Asp Pro Glu Met Gly Gly Lys Pro Arg Arg Lys Asn Pro
            85                  90                  95

Gln Glu Gly Leu Tyr Asn Glu Leu Gln Lys Asp Lys Met Ala Glu Ala
        100                 105                 110

Tyr Ser Glu Ile Gly Met Lys Gly Glu Arg Arg Arg Gly Lys Gly His
    115                 120                 125

Asp Gly Leu Tyr Gln Gly Leu Ser Thr Ala Thr Lys Asp Thr Tyr Asp
```

Ala Leu His Met Gln Ala Leu Pro Pro Arg
145             150

<210> SEQ ID NO 6
<211> LENGTH: 2046
<212> TYPE: DNA
<213> ORGANISM: Artificial Sequence
<220> FEATURE:
<223> OTHER INFORMATION: LH-CAR cDNA

<400> SEQUENCE: 6

| | | | | | |
|---|---|---|---|---|---|
| atggcctcac | cgttgacccg | ctttctgtcg | ctgaacctgc | tgctgctggg | tgagtcgatt | 60 |
| atcctgggga | gtggagaagc | ttccaggggc | cccttcggc | cactgtgccg | gcctgtcaac | 120 |
| gcaactctgg | ccgcagagaa | tgagttctgc | cagtctgca | tcaccttcac | caccagcatc | 180 |
| tgtgccggct | actgtcctag | catggtccga | gtactgccgg | ctgctttgcc | tcctgtgcct | 240 |
| cagccagtgt | gcacctaccg | ggagctgcgc | ttcgcatctg | tccgcctccc | tggctgccca | 300 |
| ccgggtgtag | accccatagt | ctcctttcct | gtagccctca | gctgccgctg | tgggccctgc | 360 |
| cggctcagta | gctctgactg | tggggtcccc | aggactcaac | caatggcctg | tgacctcccc | 420 |
| cacctccccg | gcctcctcct | cctcggtgga | ggtggatcag | gtggaggtgg | atctggtgga | 480 |
| ggtggatctc | ttcctgatgg | agactttatt | attcagggtt | gcccagaatg | taaactaaag | 540 |
| gaaaataaat | acttctccaa | gctaggagcc | cccatctacc | agtgtatggg | ctgttgcttc | 600 |
| tccagggcat | atcccactcc | tgccaggtcc | aagaagacaa | tgctggttcc | aagaatatt | 660 |
| acctcggagg | ccacatgctg | tgtggccaaa | gcatttacta | aggccacagt | aatgggaaat | 720 |
| gccagagtgg | agaatcatac | ggagtgccac | tgtagcactt | gctactacca | caagtcggaa | 780 |
| caaaaactca | tctcagaaga | ggatctggcg | ccgcatctca | ctactaccaa | gccagtgctg | 840 |
| cgaactccct | cacctgtgca | cctaccggga | catctcagc | cccagagacc | agaagattgt | 900 |
| cggccccgtg | gctcagtgaa | ggggaccgga | ttggacttcg | cctgtgatat | ttacatctgg | 960 |
| gcacccttgg | ccggaatctg | cgtggcccttt | ctgctgtcct | tgatcatcac | tctcatctgc | 1020 |
| tacaatagta | gaaggaacag | actccttcaa | agtgactaca | tgaacatgac | tccccggagg | 1080 |
| cctgggctca | ctcgaaagcc | ttaccagccc | tacgcccctg | ccagagactt | tgcagcgtac | 1140 |
| cgccccagag | caaaattcag | caggagtgca | gagactgctg | caacctgca | ggaccccaac | 1200 |
| cagctctaca | tgagctcaa | tctagggcga | gagaggaat | atgacgtctt | ggagaagaag | 1260 |
| cgggctcggg | atccagagat | gggaggcaaa | cagcagagga | ggaggaaccc | caggaaggc | 1320 |
| gtatacaatg | cactgcagaa | agacaagatg | gcagaagcct | acagtgagat | cggcacaaaa | 1380 |
| ggcgagaggc | ggagaggcaa | ggggcacgat | ggcctttacc | agggtctcag | cactgccacc | 1440 |
| aaggacacct | atgatgccct | gcatatgcag | accctggccc | ctcgcggtac | cggtcaatgt | 1500 |
| actaactacg | ctttgttgaa | actcgctggc | gatgttgaaa | gtaaccccgg | tcctggatcc | 1560 |
| atgaacccag | ccatcagcgt | cgctctcctg | ctctcagtct | tgcaggtgtc | ccgagggcag | 1620 |
| aaggtgacca | gcctgacagc | ctgcctggtg | aaccaaaacc | ttcgcctgga | ctgccgccat | 1680 |
| gagaataaca | ccaaggataa | ctccatccag | catgagttca | gcctgacccg | agagaagagg | 1740 |
| aagcacgtgc | tctcaggcac | cctcgggata | cccgagcaca | cgtaccgctc | ccgcgtcacc | 1800 |
| ctctccaacc | agcccatat | caaggtcctt | acctagcca | acttcaccac | caaggatgag | 1860 |
| ggcgactact | ttgtgagct | tcgagtctcg | ggcgcgaatc | ccatgagctc | aataaaagt | 1920 |

```
atcagtgtgt atagagacaa actggtcaag tgtggcggca taagcctgct ggttcagaac    1980
acatcctgga tgctgctgct gctgctttcc ctctccctcc tccaagccct ggacttcatt    2040
tctctg                                                                2046
```

<210> SEQ ID NO 7
<211> LENGTH: 682
<212> TYPE: PRT
<213> ORGANISM: Artificial Sequence
<220> FEATURE:
<223> OTHER INFORMATION: LH-CAR translation

<400> SEQUENCE: 7

```
Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Ser Arg Gly Pro Leu
            20                  25                  30

Arg Pro Leu Cys Arg Pro Val Asn Ala Thr Leu Ala Ala Glu Asn Glu
        35                  40                  45

Phe Cys Pro Val Cys Ile Thr Phe Thr Thr Ser Ile Cys Ala Gly Tyr
    50                  55                  60

Cys Pro Ser Met Val Arg Val Leu Pro Ala Ala Leu Pro Pro Val Pro
65                  70                  75                  80

Gln Pro Val Cys Thr Tyr Arg Glu Leu Arg Phe Ala Ser Val Arg Leu
                85                  90                  95

Pro Gly Cys Pro Pro Gly Val Asp Pro Ile Val Ser Phe Pro Val Ala
            100                 105                 110

Leu Ser Cys Arg Cys Gly Pro Cys Arg Leu Ser Ser Ser Asp Cys Gly
        115                 120                 125

Gly Pro Arg Thr Gln Pro Met Ala Cys Asp Leu Pro His Leu Pro Gly
    130                 135                 140

Leu Leu Leu Leu Gly Gly Gly Ser Gly Gly Gly Ser Gly Gly
145                 150                 155                 160

Gly Gly Ser Leu Pro Asp Gly Asp Phe Ile Ile Gln Gly Cys Pro Glu
                165                 170                 175

Cys Lys Leu Lys Glu Asn Lys Tyr Phe Ser Lys Leu Gly Ala Pro Ile
            180                 185                 190

Tyr Gln Cys Met Gly Cys Cys Phe Ser Arg Ala Tyr Pro Thr Pro Ala
        195                 200                 205

Arg Ser Lys Lys Thr Met Leu Val Pro Lys Asn Ile Thr Ser Glu Ala
    210                 215                 220

Thr Cys Cys Val Ala Lys Ala Phe Thr Lys Ala Thr Val Met Gly Asn
225                 230                 235                 240

Ala Arg Val Glu Asn His Thr Glu Cys His Cys Ser Thr Cys Tyr Tyr
                245                 250                 255

His Lys Ser Glu Gln Lys Leu Ile Ser Glu Glu Asp Leu Ala Ala Ala
            260                 265                 270

Ser Thr Thr Thr Lys Pro Val Leu Arg Thr Pro Ser Pro Val His Pro
        275                 280                 285

Thr Gly Thr Ser Gln Pro Gln Arg Pro Glu Asp Cys Arg Pro Arg Gly
    290                 295                 300

Ser Val Lys Gly Thr Gly Leu Asp Phe Ala Cys Asp Ile Tyr Ile Trp
305                 310                 315                 320

Ala Pro Leu Ala Gly Ile Cys Val Ala Leu Leu Leu Ser Leu Ile Ile
                325                 330                 335
```

-continued

Thr Leu Ile Cys Tyr Asn Ser Arg Arg Asn Arg Leu Leu Gln Ser Asp
           340                 345                 350

Tyr Met Asn Met Thr Pro Arg Arg Pro Gly Leu Thr Arg Lys Pro Tyr
        355                 360                 365

Gln Pro Tyr Ala Pro Ala Arg Asp Phe Ala Ala Tyr Arg Pro Arg Ala
    370                 375                 380

Lys Phe Ser Arg Ser Ala Glu Thr Ala Ala Asn Leu Gln Asp Pro Asn
385                 390                 395                 400

Gln Leu Tyr Asn Glu Leu Asn Leu Gly Arg Arg Glu Glu Tyr Asp Val
                405                 410                 415

Leu Glu Lys Lys Arg Ala Arg Asp Pro Glu Met Gly Gly Lys Gln Gln
            420                 425                 430

Arg Arg Arg Asn Pro Gln Glu Gly Val Tyr Asn Ala Leu Gln Lys Asp
        435                 440                 445

Lys Met Ala Glu Ala Tyr Ser Glu Ile Gly Thr Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Thr Leu Ala Pro Arg Gly
                485                 490                 495

Thr Gly Gln Cys Thr Asn Tyr Ala Leu Leu Lys Leu Ala Gly Asp Val
            500                 505                 510

Glu Ser Asn Pro Gly Pro Gly Ser Met Asn Pro Ala Ile Ser Val Ala
        515                 520                 525

Leu Leu Leu Ser Val Leu Gln Val Ser Arg Gly Gln Lys Val Thr Ser
    530                 535                 540

Leu Thr Ala Cys Leu Val Asn Gln Asn Leu Arg Leu Asp Cys Arg His
545                 550                 555                 560

Glu Asn Asn Thr Lys Asp Asn Ser Ile Gln His Glu Phe Ser Leu Thr
                565                 570                 575

Arg Glu Lys Arg Lys His Val Leu Ser Gly Thr Leu Gly Ile Pro Glu
            580                 585                 590

His Thr Tyr Arg Ser Arg Val Thr Leu Ser Asn Gln Pro Tyr Ile Lys
        595                 600                 605

Val Leu Thr Leu Ala Asn Phe Thr Thr Lys Asp Glu Gly Asp Tyr Phe
    610                 615                 620

Cys Glu Leu Arg Val Ser Gly Ala Asn Pro Met Ser Ser Asn Lys Ser
625                 630                 635                 640

Ile Ser Val Tyr Arg Asp Lys Leu Val Lys Cys Gly Gly Ile Ser Leu
                645                 650                 655

Leu Val Gln Asn Thr Ser Trp Met Leu Leu Leu Leu Leu Ser Leu Ser
            660                 665                 670

Leu Leu Gln Ala Leu Asp Phe Ile Ser Leu
        675                 680

<210> SEQ ID NO 8
<211> LENGTH: 27
<212> TYPE: PRT
<213> ORGANISM: Artificial Sequence
<220> FEATURE:
<223> OTHER INFORMATION: LH-CAR Signal Peptide

<400> SEQUENCE: 8

Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala
            20                  25

<210> SEQ ID NO 9
<211> LENGTH: 121
<212> TYPE: PRT
<213> ORGANISM: Artificial Sequence
<220> FEATURE:
<223> OTHER INFORMATION: LH beta subunit of LH-CAR

<400> SEQUENCE: 9

Ser Arg Gly Pro Leu Arg Pro Leu Cys Arg Pro Val Asn Ala Thr Leu
1               5                   10                  15

Ala Ala Glu Asn Glu Phe Cys Pro Val Cys Ile Thr Phe Thr Thr Ser
            20                  25                  30

Ile Cys Ala Gly Tyr Cys Pro Ser Met Val Arg Val Leu Pro Ala Ala
        35                  40                  45

Leu Pro Pro Val Pro Gln Pro Val Cys Thr Tyr Arg Glu Leu Arg Phe
    50                  55                  60

Ala Ser Val Arg Leu Pro Gly Cys Pro Pro Gly Val Asp Pro Ile Val
65                  70                  75                  80

Ser Phe Pro Val Ala Leu Ser Cys Arg Cys Gly Pro Cys Arg Leu Ser
                85                  90                  95

Ser Ser Asp Cys Gly Gly Pro Arg Thr Gln Pro Met Ala Cys Asp Leu
            100                 105                 110

Pro His Leu Pro Gly Leu Leu Leu Leu
        115                 120

<210> SEQ ID NO 10
<211> LENGTH: 15
<212> TYPE: PRT
<213> ORGANISM: Artificial Sequence
<220> FEATURE:
<223> OTHER INFORMATION: LH-CAR linker subcomponent

<400> SEQUENCE: 10

Gly Gly Gly Gly Ser Gly Gly Gly Ser Gly Gly Gly Ser
1               5                   10                  15

<210> SEQ ID NO 11
<211> LENGTH: 96
<212> TYPE: PRT
<213> ORGANISM: Artificial Sequence
<220> FEATURE:
<223> OTHER INFORMATION: LH alpha subunit of LH-CAR

<400> SEQUENCE: 11

Leu Pro Asp Gly Asp Phe Ile Ile Gln Gly Cys Pro Glu Cys Lys Leu
1               5                   10                  15

Lys Glu Asn Lys Tyr Phe Ser Lys Leu Gly Ala Pro Ile Tyr Gln Cys
            20                  25                  30

Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glu Ala Thr Cys Cys
    50                  55                  60

Val Ala Lys Ala Phe Thr Lys Ala Thr Val Met Gly Asn Ala Arg Val
65                  70                  75                  80

Glu Asn His Thr Glu Cys His Cys Ser Thr Cys Tyr Tyr His Lys Ser
                85                  90                  95

```
<210> SEQ ID NO 12
<211> LENGTH: 10
<212> TYPE: PRT
<213> ORGANISM: Artificial Sequence
<220> FEATURE:
<223> OTHER INFORMATION: Myc tag of LH-CAR

<400> SEQUENCE: 12

Glu Gln Lys Leu Ile Ser Glu Glu Asp Leu
1               5                   10

<210> SEQ ID NO 13
<211> LENGTH: 44
<212> TYPE: PRT
<213> ORGANISM: Artificial Sequence
<220> FEATURE:
<223> OTHER INFORMATION: LH-CAR CD8 Hinge

<400> SEQUENCE: 13

Ser Thr Thr Thr Lys Pro Val Leu Arg Thr Pro Ser Pro Val His Pro
1               5                   10                  15

Thr Gly Thr Ser Gln Pro Gln Arg Pro Glu Asp Cys Arg Pro Arg Gly
            20                  25                  30

Ser Val Lys Gly Thr Gly Leu Asp Phe Ala Cys Asp
        35                  40

<210> SEQ ID NO 14
<211> LENGTH: 25
<212> TYPE: PRT
<213> ORGANISM: Artificial Sequence
<220> FEATURE:
<223> OTHER INFORMATION: LH-CAR CD8 transmembrane domain

<400> SEQUENCE: 14

Ile Tyr Ile Trp Ala Pro Leu Ala Gly Ile Cys Val Ala Leu Leu Leu
1               5                   10                  15

Ser Leu Ile Ile Thr Leu Ile Cys Tyr
            20                  25

<210> SEQ ID NO 15
<211> LENGTH: 41
<212> TYPE: PRT
<213> ORGANISM: Artificial Sequence
<220> FEATURE:
<223> OTHER INFORMATION: LH-CAR CD28 cytoplasmic subcomponent

<400> SEQUENCE: 15

Asn Ser Arg Arg Asn Arg Leu Leu Gln Ser Asp Tyr Met Asn Met Thr
1               5                   10                  15

Pro Arg Arg Pro Gly Leu Thr Arg Lys Pro Tyr Gln Pro Tyr Ala Pro
            20                  25                  30

Ala Arg Asp Phe Ala Ala Tyr Arg Pro
        35                  40

<210> SEQ ID NO 16
<211> LENGTH: 113
<212> TYPE: PRT
<213> ORGANISM: Artificial Sequence
<220> FEATURE:
<223> OTHER INFORMATION: LH-CAR CD3 zeta subcomponent

<400> SEQUENCE: 16

Arg Ala Lys Phe Ser Arg Ser Ala Glu Thr Ala Ala Asn Leu Gln Asp
1               5                   10                  15
```

```
Pro Asn Gln Leu Tyr Asn Glu Leu Asn Leu Gly Arg Arg Glu Tyr
            20                  25                  30

Asp Val Leu Glu Lys Lys Arg Ala Arg Asp Pro Glu Met Gly Gly Lys
        35                  40                  45

Gln Gln Arg Arg Arg Asn Pro Gln Glu Gly Val Tyr Asn Ala Leu Gln
    50                  55                  60

Lys Asp Lys Met Ala Glu Ala Tyr Ser Glu Ile Gly Thr Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Thr Leu Ala Pro
            100                 105                 110

Arg

<210> SEQ ID NO 17
<211> LENGTH: 20
<212> TYPE: PRT
<213> ORGANISM: Artificial Sequence
<220> FEATURE:
<223> OTHER INFORMATION: LH-CAR E2A subcomponent

<400> SEQUENCE: 17

Gln Cys Thr Asn Tyr Ala Leu Leu Lys Leu Ala Gly Asp Val Glu Ser
1               5                   10                  15

Asn Pro Gly Pro
            20

<210> SEQ ID NO 18
<211> LENGTH: 162
<212> TYPE: PRT
<213> ORGANISM: Artificial Sequence
<220> FEATURE:
<223> OTHER INFORMATION: LH-CAR Thy1.1 subcomponent

<400> SEQUENCE: 18

Met Asn Pro Ala Ile Ser Val Ala Leu Leu Leu Ser Val Leu Gln Val
1               5                   10                  15

Ser Arg Gly Gln Lys Val Thr Ser Leu Thr Ala Cys Leu Val Asn Gln
            20                  25                  30

Asn Leu Arg Leu Asp Cys Arg His Glu Asn Asn Thr Lys Asp Asn Ser
        35                  40                  45

Ile Gln His Glu Phe Ser Leu Thr Arg Glu Lys Arg Lys His Val Leu
    50                  55                  60

Ser Gly Thr Leu Gly Ile Pro Glu His Thr Tyr Arg Ser Arg Val Thr
65                  70                  75                  80

Leu Ser Asn Gln Pro Tyr Ile Lys Val Leu Thr Leu Ala Asn Phe Thr
                85                  90                  95

Thr Lys Asp Glu Gly Asp Tyr Phe Cys Glu Leu Arg Val Ser Gly Ala
            100                 105                 110

Asn Pro Met Ser Ser Asn Lys Ser Ile Ser Val Tyr Arg Asp Lys Leu
        115                 120                 125

Val Lys Cys Gly Gly Ile Ser Leu Leu Val Gln Asn Thr Ser Trp Met
    130                 135                 140

Leu Leu Leu Leu Leu Ser Leu Ser Leu Leu Gln Ala Leu Asp Phe Ile
145                 150                 155                 160

Ser Leu
```

<210> SEQ ID NO 19
<211> LENGTH: 1443
<212> TYPE: DNA
<213> ORGANISM: Artificial Sequence
<220> FEATURE:
<223> OTHER INFORMATION: LH-CAR cDNA

<400> SEQUENCE: 19

```
atggagacag acacactcct gctatgggtg ctgctgctct gggttccagg ttccacaggt      60
tccagggagc cgcttcggcc atggtgccac cccatcaatg ccatcctggc tgtcgagaag     120
gagggctgcc cagtgtgcat caccgtcaac accaccatct gtgccggcta ctgccccacc     180
atgatgcgcg tgctgcaggc ggtcctgccg cccctgcctc aggtggtgtg cacctaccgt     240
gatgtgcgct tcgagtccat ccggctccct ggctgcccgc gtggtgtgga ccccgtggtc     300
tccttccctg tggctctcag ctgtcgctgt ggaccctgcc gccgcagcac tctgactgt      360
gggggtccca agaccacccc cttgacctgt gaccaccccc aactctcagg cctcctcttc     420
ctcggtggag gtggatcagg tggaggtgga tctggtggag gtggatctgc tcctgatgtg     480
caggattgcc agaatgcac gctacaggaa acccattct tctcccagcc gggtgcccca      540
atacttcagt gcatgggctg ctgcttctct agagcatatc ccactccact aaggtccaag     600
aagacgatgt tggtccaaaa gaacgtcacc tcagagtcca cttgctgtgt agctaaatca     660
tataacaggg tcacagtaat gggggttc aaagtggaga accacacggc gtgccactgc       720
agtacttgtt attatcacaa atctgaacaa aaactcatct cagaagagga tctggcggcc     780
gcaattgaag ttatgtatcc tcctccttac ctagacaatg aagagcaa tggaaccatt       840
atccatgtga agggaaaaca cctttgtcca agtccctat ttccggacc ttctaagccc       900
ttctgggtgc tggtggtggt gggcggggtg ctggcctgct acagcctgct ggtgacagtg     960
gccttcatca tctttttggg tgaaacgggc agaaagaaac tcctgtatat attcaaacaa    1020
ccatttatga ccagtaca aactactcaa gaggaagatg ctgtagctg ccgatttcca       1080
gaagaagaag aaggaggatg tgaactgcgg gtgaagttca gcagaagcgc cgacgcccct    1140
gcctaccagc agggccagaa tcagctgtac aacgagctga acctgggcag aagggaagag    1200
tacgacgtcc tggataagcg agagggccgg gaccctgaga tgggcggcaa gcctcggcgg    1260
aagaaccccc aggaaggcct gtataacgaa ctgcagaaag acaagatggc cgaggcctac    1320
agcgagatcg gcatgaaggg cgagcggagg cggggcaagg gccacgacgg cctgtatcag    1380
ggcctgtcca ccgccaccaa ggatacctac gacgccctgc acatgcaggc cctgcccca     1440
agg                                                                 1443
```

<210> SEQ ID NO 20
<211> LENGTH: 481
<212> TYPE: PRT
<213> ORGANISM: Artificial Sequence
<220> FEATURE:
<223> OTHER INFORMATION: LH-CAR translation

<400> SEQUENCE: 20

```
Met Glu Thr Asp Thr Leu Leu Leu Trp Val Leu Leu Leu Trp Val Pro
1               5                   10                  15

Gly Ser Thr Gly Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
        35                  40                  45

Val Asn Thr Thr Ile Cys Ala Gly Tyr Cys Pro Thr Met Met Arg Val
```

-continued

```
            50                  55                  60
Leu Gln Ala Val Leu Pro Pro Leu Pro Gln Val Val Cys Thr Tyr Arg
 65                      70                  75                  80

Asp Val Arg Phe Glu Ser Ile Arg Leu Pro Gly Cys Pro Arg Gly Val
                     85                  90                  95

Asp Pro Val Val Ser Phe Pro Val Ala Leu Ser Cys Arg Cys Gly Pro
                100                 105                 110

Cys Arg Arg Ser Thr Ser Asp Cys Gly Gly Pro Lys Asp His Pro Leu
                115                 120                 125

Thr Cys Asp His Pro Gln Leu Ser Gly Leu Leu Phe Leu Gly Gly Gly
                130                 135                 140

Gly Ser Gly Gly Gly Ser Gly Gly Gly Ser Ala Pro Asp Val
145                 150                 155                 160

Gln Asp Cys Pro Glu Cys Thr Leu Gln Glu Asn Pro Phe Phe Ser Gln
                165                 170                 175

Pro Gly Ala Pro Ile Leu Gln Cys Met Gly Cys Cys Phe Ser Arg Ala
                180                 185                 190

Tyr Pro Thr Pro Leu Arg Ser Lys Lys Thr Met Leu Val Gln Lys Asn
                195                 200                 205

Val Thr Ser Glu Ser Thr Cys Cys Val Ala Lys Ser Tyr Asn Arg Val
                210                 215                 220

Thr Val Met Gly Gly Phe Lys Val Glu Asn His Thr Ala Cys His Cys
225                 230                 235                 240

Ser Thr Cys Tyr Tyr His Lys Ser Glu Gln Lys Leu Ile Ser Glu Glu
                245                 250                 255

Asp Leu Ala Ala Ala Ile Glu Val Met Tyr Pro Pro Tyr Leu Asp
                260                 265                 270

Asn Glu Lys Ser Asn Gly Thr Ile Ile His Val Lys Gly Lys His Leu
                275                 280                 285

Cys Pro Ser Pro Leu Phe Pro Gly Pro Ser Lys Pro Phe Trp Val Leu
                290                 295                 300

Val Val Val Gly Gly Val Leu Ala Cys Tyr Ser Leu Leu Val Thr Val
305                 310                 315                 320

Ala Phe Ile Ile Phe Trp Val Lys Arg Gly Arg Lys Lys Leu Leu Tyr
                325                 330                 335

Ile Phe Lys Gln Pro Phe Met Arg Pro Val Gln Thr Thr Gln Glu Glu
                340                 345                 350

Asp Gly Cys Ser Cys Arg Phe Pro Glu Glu Glu Glu Gly Gly Cys Glu
                355                 360                 365

Leu Arg Val Lys Phe Ser Arg Ser Ala Asp Ala Pro Ala Tyr Gln Gln
                370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Gly Arg Asp Pro Glu Met Gly Gly
                405                 410                 415

Lys Pro Arg Arg Lys Asn Pro Gln Glu Gly Leu Tyr Asn Glu Leu Gln
                420                 425                 430

Lys Asp Lys Met Ala Glu Ala Tyr Ser Glu Ile Gly Met Lys Gly Glu
                435                 440                 445

Arg Arg Arg Gly Lys Gly His Asp Gly Leu Tyr Gln Gly Leu Ser Thr
                450                 455                 460

Ala Thr Lys Asp Thr Tyr Asp Ala Leu His Met Gln Ala Leu Pro Pro
465                 470                 475                 480
```

Arg

<210> SEQ ID NO 21
<211> LENGTH: 20
<212> TYPE: PRT
<213> ORGANISM: Artificial Sequence
<220> FEATURE:
<223> OTHER INFORMATION: LH-CAR signal peptide

<400> SEQUENCE: 21

Met Glu Thr Asp Thr Leu Leu Leu Trp Val Leu Leu Leu Trp Val Pro
1               5                   10                  15

Gly Ser Thr Gly
            20

<210> SEQ ID NO 22
<211> LENGTH: 121
<212> TYPE: PRT
<213> ORGANISM: Artificial Sequence
<220> FEATURE:
<223> OTHER INFORMATION: LH beta subunit of LH-CAR

<400> SEQUENCE: 22

Ser Arg Glu Pro Leu Arg Pro Trp Cys His Pro Ile Asn Ala Ile Leu
1               5                   10                  15

Ala Val Glu Lys Glu Gly Cys Pro Val Cys Ile Thr Val Asn Thr Thr
                20                  25                  30

Ile Cys Ala Gly Tyr Cys Pro Thr Met Met Arg Val Leu Gln Ala Val
            35                  40                  45

Leu Pro Pro Leu Pro Gln Val Val Cys Thr Tyr Arg Asp Val Arg Phe
    50                  55                  60

Glu Ser Ile Arg Leu Pro Gly Cys Pro Arg Gly Val Asp Pro Val Val
65                  70                  75                  80

Ser Phe Pro Val Ala Leu Ser Cys Arg Cys Gly Pro Cys Arg Arg Ser
                85                  90                  95

Thr Ser Asp Cys Gly Gly Pro Lys Asp His Pro Leu Thr Cys Asp His
            100                 105                 110

Pro Gln Leu Ser Gly Leu Leu Phe Leu
        115                 120

<210> SEQ ID NO 23
<211> LENGTH: 92
<212> TYPE: PRT
<213> ORGANISM: Artificial Sequence
<220> FEATURE:
<223> OTHER INFORMATION: LH alpha subunit of LH-CAR

<400> SEQUENCE: 23

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
                20                  25                  30

Phe Ser Arg Ala Tyr Pro Thr Pro Leu Arg Ser Lys Lys Thr Met Leu
            35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 24
<211> LENGTH: 39
<212> TYPE: PRT
<213> ORGANISM: Artificial Sequence
<220> FEATURE:
<223> OTHER INFORMATION: LH-CAR CD28 hinge

<400> SEQUENCE: 24

Ile Glu Val Met Tyr Pro Pro Pro Tyr Leu Asp Asn Glu Lys Ser Asn
1               5                   10                  15
Gly Thr Ile Ile His Val Lys Gly Lys His Leu Cys Pro Ser Pro Leu
            20                  25                  30
Phe Pro Gly Pro Ser Lys Pro
        35

<210> SEQ ID NO 25
<211> LENGTH: 27
<212> TYPE: PRT
<213> ORGANISM: Artificial Sequence
<220> FEATURE:
<223> OTHER INFORMATION: LH-CAR CD28 transmembrane domain

<400> SEQUENCE: 25

Phe Trp Val Leu Val Val Val Gly Gly Val Leu Ala Cys Tyr Ser Leu
1               5                   10                  15
Leu Val Thr Val Ala Phe Ile Ile Phe Trp Val
            20                  25

<210> SEQ ID NO 26
<211> LENGTH: 42
<212> TYPE: PRT
<213> ORGANISM: Artificial Sequence
<220> FEATURE:
<223> OTHER INFORMATION: LH-CAR 4-1BB subcomponent

<400> SEQUENCE: 26

Lys Arg Gly Arg Lys Lys Leu Leu Tyr Ile Phe Lys Gln Pro Phe Met
1               5                   10                  15
Arg Pro Val Gln Thr Thr Gln Glu Glu Asp Gly Cys Ser Cys Arg Phe
            20                  25                  30
Pro Glu Glu Glu Glu Gly Gly Cys Glu Leu
        35                  40

<210> SEQ ID NO 27
<211> LENGTH: 112
<212> TYPE: PRT
<213> ORGANISM: Artificial Sequence
<220> FEATURE:
<223> OTHER INFORMATION: LH-CAR CD3 zeta subcomponent

<400> SEQUENCE: 27

Arg Val Lys Phe Ser Arg Ser Ala Asp Ala Pro Ala Tyr Gln Gln Gly
1               5                   10                  15
Gln Asn Gln Leu Tyr Asn Glu Leu Asn Leu Gly Arg Arg Glu Glu Tyr
            20                  25                  30
Asp Val Leu Asp Lys Arg Arg Gly Arg Asp Pro Glu Met Gly Gly Lys
            35                  40                  45
Pro Arg Arg Lys Asn Pro Gln Glu Gly Leu Tyr Asn Glu Leu Gln Lys
        50                  55                  60
Asp Lys Met Ala Glu Ala Tyr Ser Glu Ile Gly Met Lys Gly Glu Arg

```
                65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
               100                 105                 110

<210> SEQ ID NO 28
<211> LENGTH: 9
<212> TYPE: PRT
<213> ORGANISM: Artificial Sequence
<220> FEATURE:
<223> OTHER INFORMATION: CDRH1 of anti-LHR Binding Agent

<400> SEQUENCE: 28

Gly Tyr Ser Ile Thr Ser Gly Tyr Gly
1               5

<210> SEQ ID NO 29
<211> LENGTH: 7
<212> TYPE: PRT
<213> ORGANISM: Artificial Sequence
<220> FEATURE:
<223> OTHER INFORMATION: CDRH2 of anti-LHR Binding Agent

<400> SEQUENCE: 29

Ile His Tyr Ser Gly Ser Thr
1               5

<210> SEQ ID NO 30
<211> LENGTH: 6
<212> TYPE: PRT
<213> ORGANISM: Artificial Sequence
<220> FEATURE:
<223> OTHER INFORMATION: CDRH3 of anti-LHR Binding Agent

<400> SEQUENCE: 30

Ala Arg Ser Leu Arg Tyr
1               5

<210> SEQ ID NO 31
<211> LENGTH: 5
<212> TYPE: PRT
<213> ORGANISM: Artificial Sequence
<220> FEATURE:
<223> OTHER INFORMATION: CDRL1 of anti-LHR Binding Agent

<400> SEQUENCE: 31

Ser Ser Val Asn Tyr
1               5

<210> SEQ ID NO 32
<211> LENGTH: 9
<212> TYPE: PRT
<213> ORGANISM: Artificial Sequence
<220> FEATURE:
<223> OTHER INFORMATION: CDRL3 of anti-LHR Binding Agent

<400> SEQUENCE: 32

His Gln Trp Ser Ser Tyr Pro Tyr Thr
1               5

<210> SEQ ID NO 33
<211> LENGTH: 8
<212> TYPE: PRT
<213> ORGANISM: Artificial Sequence
<220> FEATURE:
```

<223> OTHER INFORMATION: CDRH1 of anti-LHR Binding Agent

<400> SEQUENCE: 33

Gly Phe Ser Leu Thr Thr Tyr Gly
1               5

<210> SEQ ID NO 34
<211> LENGTH: 7
<212> TYPE: PRT
<213> ORGANISM: Artificial Sequence
<220> FEATURE:
<223> OTHER INFORMATION: CDRH2 of anti-LHR Binding Agent

<400> SEQUENCE: 34

Ile Trp Gly Asp Gly Ser Thr
1               5

<210> SEQ ID NO 35
<211> LENGTH: 9
<212> TYPE: PRT
<213> ORGANISM: Artificial Sequence
<220> FEATURE:
<223> OTHER INFORMATION: CDRH3 of anti-LHR Binding Agent

<400> SEQUENCE: 35

Ala Glu Gly Ser Ser Leu Phe Ala Tyr
1               5

<210> SEQ ID NO 36
<211> LENGTH: 12
<212> TYPE: PRT
<213> ORGANISM: Artificial Sequence
<220> FEATURE:
<223> OTHER INFORMATION: CDRL1 of anti-LHR Binding Agent

<400> SEQUENCE: 36

Gln Ser Leu Leu Asn Ser Gly Asn Gln Lys Asn Tyr
1               5                   10

<210> SEQ ID NO 37
<211> LENGTH: 9
<212> TYPE: PRT
<213> ORGANISM: Artificial Sequence
<220> FEATURE:
<223> OTHER INFORMATION: CDRL3 of anti-LHR Binding Agent

<400> SEQUENCE: 37

Gln Asn Asp Tyr Ser Tyr Pro Leu Thr
1               5

<210> SEQ ID NO 38
<211> LENGTH: 8
<212> TYPE: PRT
<213> ORGANISM: Artificial Sequence
<220> FEATURE:
<223> OTHER INFORMATION: CDRH1 of anti-LHR Binding Agent

<400> SEQUENCE: 38

Gly Tyr Ser Phe Thr Gly Tyr Tyr
1               5

<210> SEQ ID NO 39
<211> LENGTH: 8
<212> TYPE: PRT
<213> ORGANISM: Artificial Sequence
<220> FEATURE:
<223> OTHER INFORMATION: CDRH2 of anti-LHR Binding Agent

<400> SEQUENCE: 39

Ile Tyr Pro Tyr Asn Gly Val Ser
1               5

<210> SEQ ID NO 40
<211> LENGTH: 14
<212> TYPE: PRT
<213> ORGANISM: Artificial Sequence
<220> FEATURE:
<223> OTHER INFORMATION: CDRH3 of anti-LHR Binding Agent

<400> SEQUENCE: 40

Ala Arg Glu Arg Gly Leu Tyr Gln Leu Arg Ala Met Asp Tyr
1               5                   10

<210> SEQ ID NO 41
<211> LENGTH: 6
<212> TYPE: PRT
<213> ORGANISM: Artificial Sequence
<220> FEATURE:
<223> OTHER INFORMATION: CDRL1 of anti-LHR Binding Agent

<400> SEQUENCE: 41

Gln Ser Ile Ser Asn Asn
1               5

<210> SEQ ID NO 42
<211> LENGTH: 9
<212> TYPE: PRT
<213> ORGANISM: Artificial Sequence
<220> FEATURE:
<223> OTHER INFORMATION: CDRL3 of anti-LHR Binding Agent

<400> SEQUENCE: 42

Gln Gln Ser Asn Ser Trp Pro Tyr Thr
1               5

<210> SEQ ID NO 43
<211> LENGTH: 111
<212> TYPE: PRT
<213> ORGANISM: Artificial Sequence
<220> FEATURE:
<223> OTHER INFORMATION: Anti-LHR Binding Agent includes a heavy chain

<400> SEQUENCE: 43

Glu Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Gly Trp His Arg Gln Phe Pro Gly Asn Lys Leu Glu Trp Met Gly
        35                  40                  45

Tyr Ile His Tyr Ser Gly Ser Thr Thr Tyr Asn Pro Ser Leu Lys Ser
    50                  55                  60

Arg Ile Ser Ile Ser Arg Asp Thr Ser Lys Asn Gln Phe Phe Leu Gln
65                  70                  75                  80

Leu Asn Ser Val Thr Thr Glu Asp Thr Ala Thr Tyr Tyr Cys Ala Arg
                85                  90                  95

Ser Leu Arg Tyr Trp Gly Gln Gly Thr Thr Leu Thr Val Ser Ser
            100                 105                 110

<210> SEQ ID NO 44
<211> LENGTH: 106

<212> TYPE: PRT
<213> ORGANISM: Artificial Sequence
<220> FEATURE:
<223> OTHER INFORMATION: Anti-LHR Binding Agent includes a light chain

<400> SEQUENCE: 44

Asp Ile Val Met Thr Gln Thr Pro Ala Ile Met Ser Ala Ser Pro Gly
1               5                   10                  15

Gln Lys Val Thr Ile Thr Cys Ser Ala Ser Ser Val Asn Tyr Met
            20                  25                  30

His Trp Tyr Gln Gln Lys Leu Gly Ser Ser Pro Lys Leu Trp Ile Tyr
        35                  40                  45

Asp Thr Ser Lys Leu Ala Pro Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ser Tyr Phe Cys His Gln Trp Ser Ser Tyr Pro Tyr Thr
                85                  90                  95

Phe Gly Ser Gly Thr Lys Leu Glu Ile Lys
            100                 105

<210> SEQ ID NO 45
<211> LENGTH: 115
<212> TYPE: PRT
<213> ORGANISM: Artificial Sequence
<220> FEATURE:
<223> OTHER INFORMATION: Anti-LHR Binding Agent includes a heavy chain

<400> SEQUENCE: 45

Gln Val Gln Leu Lys Glu Ser Gly Pro Gly Leu Val Ala Pro Ser Gln
1               5                   10                  15

Ser Leu Ser Arg Arg Cys Thr Val Ser Gly Phe Ser Leu Thr Thr Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Tyr Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Glu Gly Ser Ser Leu Phe Ala Tyr Trp Gly Gln Gly Thr Leu Val Thr
            100                 105                 110

Val Ser Ala
        115

<210> SEQ ID NO 46
<211> LENGTH: 113
<212> TYPE: PRT
<213> ORGANISM: Artificial Sequence
<220> FEATURE:
<223> OTHER INFORMATION: Anti-LHR Binding Agent includes a light chain
<220> FEATURE:
<221> NAME/KEY: misc_feature
<222> LOCATION: (89)..(89)
<223> OTHER INFORMATION: Xaa can be any naturally occurring amino acid

<400> SEQUENCE: 46

Asp Ile Val Met Thr Gln Ser Pro Ser Ser Leu Thr Val Thr Ala Gly
1               5                   10                  15

```
Glu Lys Val Thr Met Ser Cys Lys Ser Ser Gln Ser Leu Leu Asn Ser
                 20                  25                  30

Gly Asn Gln Lys Asn Tyr Leu Thr Trp Tyr Gln Lys Pro Gly Gln
             35                  40                  45

Pro Pro Lys Leu Leu Ile Tyr Trp Ala Ser Thr Arg Gln Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Xaa Ala Val Tyr Tyr Cys Gln Asn
                 85                  90                  95

Asp Tyr Ser Tyr Pro Leu Thr Phe Gly Ser Gly Thr Lys Leu Glu Ile
                100                 105                 110

Lys
```

<210> SEQ ID NO 47
<211> LENGTH: 103
<212> TYPE: PRT
<213> ORGANISM: Artificial Sequence
<220> FEATURE:
<223> OTHER INFORMATION: Anti-LHR Binding Agent includes a heavy chain

<400> SEQUENCE: 47

```
Glu Val Gln Leu Glu Gln Ser Gly Gly Gly Leu Val Gln Pro Gly Gly
 1               5                  10                  15

Ser Arg Lys Leu Ser Cys Ala Ala Ser Gly Phe Thr Phe Ser Ser Phe
                 20                  25                  30

Gly Met His Trp Val Arg Gln Ala Pro Glu Lys Gly Leu Glu Trp Val
             35                  40                  45

Ala Tyr Ile Ser Ser Gly Ser Ser Thr Leu His Tyr Ala Asp Thr Val
 50                  55                  60

Lys Gly Arg Phe Thr Ile Ser Arg Asp Asn Pro Lys Asn Thr Leu Phe
 65                  70                  75                  80

Leu Gln Met Lys Leu Pro Ser Leu Cys Tyr Leu Leu Gly Ser Arg
                 85                  90                  95

Asn Leu Ser His Arg Leu Leu
                100
```

<210> SEQ ID NO 48
<211> LENGTH: 107
<212> TYPE: PRT
<213> ORGANISM: Artificial Sequence
<220> FEATURE:
<223> OTHER INFORMATION: Anti-LHR Binding Agent includes a light chain

<400> SEQUENCE: 48

```
Asp Ile Val Leu Thr Gln Thr Pro Ser Ser Leu Ser Ala Ser Leu Gly
 1               5                  10                  15

Asp Thr Ile Thr Ile Thr Cys His Ala Ser Gln Asn Ile Asn Val Trp
                 20                  25                  30

Leu Phe Trp Tyr Gln Gln Lys Pro Gly Asn Ile Pro Lys Leu Leu Ile
             35                  40                  45

Tyr Lys Ala Ser Asn Leu Leu Thr Gly Val Pro Ser Arg Phe Ser Gly
 50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Gly Gln Ser Phe Pro Trp
                 85                  90                  95
```

```
Thr Phe Gly Gly Gly Thr Lys Leu Glu Ile Lys
            100                 105
```

<210> SEQ ID NO 49
<211> LENGTH: 121
<212> TYPE: PRT
<213> ORGANISM: Artificial Sequence
<220> FEATURE:
<223> OTHER INFORMATION: Anti-LHR Binding Agent includes a heavy chain

<400> SEQUENCE: 49

```
Gln Val Lys Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Asn Ile Leu Asp Trp Ile
        35                  40                  45

Gly Tyr Ile Tyr Pro Tyr Asn Gly Val Ser Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Gly Leu Tyr Gln Leu Arg Ala Met Asp Tyr Trp Gly
            100                 105                 110

Gln Gly Thr Ser Val Thr Val Ser Ser
        115                 120
```

<210> SEQ ID NO 50
<211> LENGTH: 107
<212> TYPE: PRT
<213> ORGANISM: Artificial Sequence
<220> FEATURE:
<223> OTHER INFORMATION: Anti-LHR Binding Agent includes a light chain

<400> SEQUENCE: 50

```
Asp Ile Val Leu Thr Gln Thr Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Asn Ala Ser Gln Ser Ile Ser Gly Ile Pro Ser Lys Phe Ser Gly
    50                  55                  60

Ser Gly Ser Gly Thr Asp Phe Thr Leu Arg Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Ser Gly Thr Lys Leu Glu Ile Lys
            100                 105
```

<210> SEQ ID NO 51
<211> LENGTH: 10
<212> TYPE: PRT
<213> ORGANISM: Artificial Sequence
<220> FEATURE:
<223> OTHER INFORMATION: Recombinant LH agonist

<400> SEQUENCE: 51

```
Glu His Trp Ser Tyr Gly Leu Arg Pro Gly
```

```
<210> SEQ ID NO 52
<211> LENGTH: 15
<212> TYPE: PRT
<213> ORGANISM: Artificial Sequence
<220> FEATURE:
<223> OTHER INFORMATION: Variant Fc region

<400> SEQUENCE: 52

Glu Pro Lys Ser Cys Asp Lys Thr His Thr Cys Pro Pro Cys Pro
1               5                   10                  15

<210> SEQ ID NO 53
<211> LENGTH: 12
<212> TYPE: PRT
<213> ORGANISM: Artificial Sequence
<220> FEATURE:
<223> OTHER INFORMATION: Variant Fc region

<400> SEQUENCE: 53

Glu Arg Lys Cys Cys Val Glu Cys Pro Pro Cys Pro
1               5                   10

<210> SEQ ID NO 54
<211> LENGTH: 16
<212> TYPE: PRT
<213> ORGANISM: Artificial Sequence
<220> FEATURE:
<223> OTHER INFORMATION: Variant Fc region

<400> SEQUENCE: 54

Glu Leu Lys Thr Pro Leu Gly Asp Thr His Thr Cys Pro Arg Cys Pro
1               5                   10                  15

<210> SEQ ID NO 55
<211> LENGTH: 12
<212> TYPE: PRT
<213> ORGANISM: Artificial Sequence
<220> FEATURE:
<223> OTHER INFORMATION: Variant Fc region

<400> SEQUENCE: 55

Glu Ser Lys Tyr Gly Pro Pro Cys Pro Ser Cys Pro
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Variant Fc region

<400> SEQUENCE: 56

Glu Ser Lys Tyr Gly Pro Pro Cys Pro Pro Cys Pro
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Variant Fc region

<400> SEQUENCE: 57

Tyr Gly Pro Pro Cys Pro Pro Cys Pro
1               5
```

```
<210> SEQ ID NO 58
<211> LENGTH: 10
<212> TYPE: PRT
<213> ORGANISM: Artificial Sequence
<220> FEATURE:
<223> OTHER INFORMATION: Variant Fc region

<400> SEQUENCE: 58

Lys Tyr Gly Pro Pro Cys Pro Pro Cys Pro
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Variant Fc region

<400> SEQUENCE: 59

Glu Val Val Lys Tyr Gly Pro Pro Cys Pro Pro Cys Pro
1               5                   10

<210> SEQ ID NO 60
<211> LENGTH: 220
<212> TYPE: PRT
<213> ORGANISM: Artificial Sequence
<220> FEATURE:
<223> OTHER INFORMATION: CD28 signaling region

<400> SEQUENCE: 60

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220
```

```
<210> SEQ ID NO 61
<211> LENGTH: 29
<212> TYPE: PRT
<213> ORGANISM: Artificial Sequence
<220> FEATURE:
<223> OTHER INFORMATION: ITAM1

<400> SEQUENCE: 61

Ala Pro Ala Tyr Gln Gln Gly Gln Asn Gln Leu Tyr Asn Glu Leu Asn
1               5                   10                  15

Leu Gly Arg Arg Glu Glu Tyr Asp Val Leu Asp Lys Arg
            20                  25

<210> SEQ ID NO 62
<211> LENGTH: 29
<212> TYPE: PRT
<213> ORGANISM: Artificial Sequence
<220> FEATURE:
<223> OTHER INFORMATION: ITAM2

<400> SEQUENCE: 62

Pro Gln Arg Arg Lys Asn Pro Gln Glu Gly Leu Tyr Asn Glu Leu Gln
1               5                   10                  15

Lys Asp Lys Met Ala Glu Ala Tyr Ser Glu Ile Gly Met
            20                  25

<210> SEQ ID NO 63
<211> LENGTH: 29
<212> TYPE: PRT
<213> ORGANISM: Artificial Sequence
<220> FEATURE:
<223> OTHER INFORMATION: ITAM3

<400> SEQUENCE: 63

Glu Arg Arg Arg Gly Lys Gly His Asp Gly Leu Tyr Gln Gly Leu Ser
1               5                   10                  15

Thr Ala Thr Lys Asp Thr Tyr Asp Ala Leu His Met Gln
            20                  25

<210> SEQ ID NO 64
<211> LENGTH: 48
<212> TYPE: PRT
<213> ORGANISM: Artificial Sequence
<220> FEATURE:
<223> OTHER INFORMATION: IgG1 heavy chain hinge sequence

<400> SEQUENCE: 64

Cys Thr Cys Gly Ala Gly Cys Cys Cys Ala Ala Ala Thr Cys Thr Thr
1               5                   10                  15

Gly Thr Gly Ala Cys Ala Ala Ala Ala Cys Thr Cys Ala Cys Ala Cys
            20                  25                  30

Ala Thr Gly Cys Cys Cys Ala Cys Cys Gly Thr Gly Cys Cys Cys Gly
        35                  40                  45

<210> SEQ ID NO 65
<211> LENGTH: 51
<212> TYPE: PRT
<213> ORGANISM: Artificial Sequence
<220> FEATURE:
<223> OTHER INFORMATION: CD8 hinge domain

<400> SEQUENCE: 65

Pro Ala Lys Pro Thr Thr Thr Pro Ala Pro Arg Pro Pro Thr Pro Ala
1               5                   10                  15
```

```
Pro Thr Ile Ala Ser Gln Pro Leu Ser Leu Arg Pro Glu Ala Cys Arg
            20                  25                  30

Pro Ala Ala Gly Gly Ala Val His Thr Arg Gly Leu Asp Phe Ala Cys
        35                  40                  45

Asp Ile Tyr
    50

<210> SEQ ID NO 66
<211> LENGTH: 49
<212> TYPE: PRT
<213> ORGANISM: Artificial Sequence
<220> FEATURE:
<223> OTHER INFORMATION: CD8 hinge domain

<400> SEQUENCE: 66

Lys Val Asn Ser Thr Thr Thr Lys Pro Val Leu Arg Thr Pro Ser Pro
1               5                   10                  15

Val His Pro Thr Gly Thr Ser Gln Pro Gln Arg Pro Glu Asp Cys Arg
            20                  25                  30

Pro Arg Gly Ser Val Lys Gly Thr Gly Leu Asp Phe Ala Cys Asp Ile
        35                  40                  45

Tyr

<210> SEQ ID NO 67
<211> LENGTH: 51
<212> TYPE: PRT
<213> ORGANISM: Artificial Sequence
<220> FEATURE:
<223> OTHER INFORMATION: CD8 hinge domain

<400> SEQUENCE: 67

Pro Val Lys Pro Thr Thr Thr Pro Ala Pro Arg Pro Pro Thr Gln Ala
1               5                   10                  15

Pro Ile Thr Thr Ser Gln Arg Val Ser Leu Arg Pro Gly Thr Cys Gln
            20                  25                  30

Pro Ser Ala Gly Ser Thr Val Glu Ala Ser Gly Leu Asp Leu Ser Cys
        35                  40                  45

Asp Ile Tyr
    50

<210> SEQ ID NO 68
<211> LENGTH: 119
<212> TYPE: PRT
<213> ORGANISM: Artificial Sequence
<220> FEATURE:
<223> OTHER INFORMATION: intermediate length spacer including an IgG4
      hinge and a CH3 region

<400> SEQUENCE: 68

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80
```

Arg Leu Thr Val Asp Lys Ser Arg Trp Gln Glu Gly Asn Val Phe Ser
            85                  90                  95

Cys Ser Val Met His Glu Ala Leu His Asn His Tyr Thr Gln Lys Ser
        100                 105                 110

Leu Ser Leu Ser Leu Gly Lys
        115

<210> SEQ ID NO 69
<211> LENGTH: 229
<212> TYPE: PRT
<213> ORGANISM: Artificial Sequence
<220> FEATURE:
<223> OTHER INFORMATION: longer length spacer including an IgG4 hinge
      and a CH3 region

<400> SEQUENCE: 69

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
        100                 105                 110

Ser Ile Glu Lys Thr Ile Ser Lys Ala Lys Gly Gln Pro Arg Glu Pro
    115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
        180                 185                 190

Thr Val Asp Lys Ser Arg Trp Gln Glu Gly Asn Val Phe Ser Cys Ser
    195                 200                 205

Val Met His Glu Ala Leu His Asn His Tyr Thr Gln Lys Ser Leu Ser
210                 215                 220

Leu Ser Leu Gly Lys
225

<210> SEQ ID NO 70
<211> LENGTH: 21
<212> TYPE: PRT
<213> ORGANISM: Artificial Sequence
<220> FEATURE:
<223> OTHER INFORMATION: CD8 transmembrane domain

<400> SEQUENCE: 70

Ile Tyr Ile Trp Ala Pro Leu Ala Gly Thr Cys Gly Val Leu Leu Leu
1               5                   10                  15

Ser Leu Val Ile Thr

```
                20

<210> SEQ ID NO 71
<211> LENGTH: 21
<212> TYPE: PRT
<213> ORGANISM: Artificial Sequence
<220> FEATURE:
<223> OTHER INFORMATION: CD8 transmembrane domain

<400> SEQUENCE: 71

Ile Trp Ala Pro Leu Ala Gly Ile Cys Ala Val Leu Leu Leu Ser Leu
1               5                   10                  15

Val Ile Thr Leu Ile
            20

<210> SEQ ID NO 72
<211> LENGTH: 8
<212> TYPE: PRT
<213> ORGANISM: Artificial Sequence
<220> FEATURE:
<223> OTHER INFORMATION: CAR linker sequence

<400> SEQUENCE: 72

Gly Gly Gly Ser Gly Gly Gly Ser
1               5

<210> SEQ ID NO 73
<211> LENGTH: 11
<212> TYPE: PRT
<213> ORGANISM: Artificial Sequence
<220> FEATURE:
<223> OTHER INFORMATION: CAR linker sequence

<400> SEQUENCE: 73

Gly Gly Gly Ser Gly Gly Gly Ser Gly Gly Ser
1               5                   10

<210> SEQ ID NO 74
<211> LENGTH: 110
<212> TYPE: PRT
<213> ORGANISM: Artificial Sequence
<220> FEATURE:
<223> OTHER INFORMATION: CH2 sequence

<400> SEQUENCE: 74

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 75
<211> LENGTH: 107
<212> TYPE: PRT
```

```
<213> ORGANISM: Artificial Sequence
<220> FEATURE:
<223> OTHER INFORMATION: CH3 sequence

<400> SEQUENCE: 75

Gly Gln Pro Arg Glu Pro Gln Val Tyr Thr Leu Pro Pro Ser Gln Glu
1               5                   10                  15
Glu Met Thr Lys Asn Gln Val Ser Leu Thr Cys Leu Val Lys Gly Phe
            20                  25                  30
Tyr Pro Ser Asp Ile Ala Val Glu Trp Glu Ser Asn Gly Gln Pro Glu
        35                  40                  45
Asn Asn Tyr Lys Thr Thr Pro Pro Val Leu Asp Ser Asp Gly Ser Phe
    50                  55                  60
Phe Leu Tyr Ser Arg Leu Thr Val Asp Lys Ser Arg Trp Gln Glu Gly
65                  70                  75                  80
Asn Val Phe Ser Cys Ser Val Met His Glu Ala Leu His Asn His Tyr
                85                  90                  95
Thr Gln Lys Ser Leu Ser Leu Ser Leu Gly Lys
            100                 105

<210> SEQ ID NO 76
<211> LENGTH: 8
<212> TYPE: PRT
<213> ORGANISM: Artificial Sequence
<220> FEATURE:
<223> OTHER INFORMATION: STREP tag

<400> SEQUENCE: 76

Trp Arg His Pro Gln Phe Gly Gly
1               5

<210> SEQ ID NO 77
<211> LENGTH: 8
<212> TYPE: PRT
<213> ORGANISM: Artificial Sequence
<220> FEATURE:
<223> OTHER INFORMATION: STREP TAG II

<400> SEQUENCE: 77

Trp Ser His Pro Gln Phe Glu Lys
1               5

<210> SEQ ID NO 78
<211> LENGTH: 8
<212> TYPE: PRT
<213> ORGANISM: Artificial Sequence
<220> FEATURE:
<223> OTHER INFORMATION: Flag Tag

<400> SEQUENCE: 78

Asp Tyr Lys Asp Asp Asp Asp Lys
1               5

<210> SEQ ID NO 79
<211> LENGTH: 8
<212> TYPE: PRT
<213> ORGANISM: Artificial Sequence
<220> FEATURE:
<223> OTHER INFORMATION: Xpress tag

<400> SEQUENCE: 79

Asp Leu Tyr Asp Asp Asp Asp Lys
1               5
```

```
<210> SEQ ID NO 80
<211> LENGTH: 15
<212> TYPE: PRT
<213> ORGANISM: Artificial Sequence
<220> FEATURE:
<223> OTHER INFORMATION: Avi tag

<400> SEQUENCE: 80

Gly Leu Asn Asp Ile Phe Glu Ala Gln Lys Ile Glu Trp His Glu
1               5                   10                  15

<210> SEQ ID NO 81
<211> LENGTH: 26
<212> TYPE: PRT
<213> ORGANISM: Artificial Sequence
<220> FEATURE:
<223> OTHER INFORMATION: Calmodulin tag

<400> SEQUENCE: 81

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 82
<211> LENGTH: 9
<212> TYPE: PRT
<213> ORGANISM: Artificial Sequence
<220> FEATURE:
<223> OTHER INFORMATION: HA tag

<400> SEQUENCE: 82

Tyr Pro Tyr Asp Val Pro Asp Tyr Ala
1               5

<210> SEQ ID NO 83
<211> LENGTH: 13
<212> TYPE: PRT
<213> ORGANISM: Artificial Sequence
<220> FEATURE:
<223> OTHER INFORMATION: Softag1

<400> SEQUENCE: 83

Ser Leu Ala Glu Leu Leu Asn Ala Gly Leu Gly Gly Ser
1               5                   10

<210> SEQ ID NO 84
<211> LENGTH: 8
<212> TYPE: PRT
<213> ORGANISM: Artificial Sequence
<220> FEATURE:
<223> OTHER INFORMATION: Softag3

<400> SEQUENCE: 84

Thr Gln Asp Pro Ser Arg Val Gly
1               5

<210> SEQ ID NO 85
<211> LENGTH: 14
<212> TYPE: PRT
<213> ORGANISM: Artificial Sequence
<220> FEATURE:
<223> OTHER INFORMATION: V5 tag

<400> SEQUENCE: 85

Gly Lys Pro Ile Pro Asn Pro Leu Leu Gly Leu Asp Ser Thr
```

-continued

```
<210> SEQ ID NO 86
<211> LENGTH: 24
<212> TYPE: PRT
<213> ORGANISM: Artificial Sequence
<220> FEATURE:
<223> OTHER INFORMATION: T2A

<400> SEQUENCE: 86

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 87
<211> LENGTH: 21
<212> TYPE: PRT
<213> ORGANISM: Artificial Sequence
<220> FEATURE:
<223> OTHER INFORMATION: T2A

<400> SEQUENCE: 87

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 88
<211> LENGTH: 22
<212> TYPE: PRT
<213> ORGANISM: Artificial Sequence
<220> FEATURE:
<223> OTHER INFORMATION: P2A

<400> SEQUENCE: 88

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 89
<211> LENGTH: 24
<212> TYPE: PRT
<213> ORGANISM: Artificial Sequence
<220> FEATURE:
<223> OTHER INFORMATION: E2A

<400> SEQUENCE: 89

Gly Ser Gly Gln Cys Thr Asn Tyr Ala Leu Leu Lys Leu Ala Gly Asp
1               5                   10                  15

Val Glu Ser Asn Pro Gly Pro Pro
            20

<210> SEQ ID NO 90
<211> LENGTH: 25
<212> TYPE: PRT
<213> ORGANISM: Artificial Sequence
<220> FEATURE:
<223> OTHER INFORMATION: F2A
```

```
<400> SEQUENCE: 90

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```

LUTEINIZING HORMONE RECEPTOR BINDING AGENTS AND LUTEINIZING HORMONE AGONISTS TO IDENTIFY, EXPAND, ABLATE AND MODIFY STEM CELLS

CROSS-REFERENCE TO RELATED APPLICATIONS

This application is a U.S. National Stage Entry of PCT/US2018/054004 filed Oct. 2, 2018, which claims priority to U.S. Provisional Patent Application No. 62/566,897 filed Oct. 2, 2017, the entire contents of both of which are incorporated by reference herein.

STATEMENT REGARDING FEDERALLY SPONSORED RESEARCH OR DEVELOPMENT

This invention was made with government support under HL069929 and CA008748 awarded by the National Institutes of Health. The government has certain rights in the invention.

STATEMENT REGARDING SEQUENCE LISTING

The Sequence Listing associated with this application is provided in text format in lieu of a paper copy and is hereby incorporated by reference into the specification. The name of the text file containing the Sequence Listing is 29H9647_ST25.txt. The text file is 8.25 KB, was created on Mar. 31, 2020, and is being submitted electronically via EFS-Web.

FIELD OF THE DISCLOSURE

The use of luteinizing hormone receptor (LHR) binding agents and luteinizing hormone (LH) agonists to enrich for primitive hematopoietic stem cell (pHSC) populations, to target pHSC for ablation, and/or to expand pHSC populations are described. The methods can be used to prepare therapeutic hematopoietic stem cell (HSC) populations, to prepare patients for therapeutic HSC transplants or genetic cell therapies, and/or to treat malignancies, such as those associated with hyperproliferative HSC.

BACKGROUND OF THE DISCLOSURE

Hematopoietic stem cells (HSC) are stem cells that can give rise to all blood cell types such as white blood cells and red blood cells. The therapeutic administration of HSC can be used to treat a variety of side-effects of radiation exposure (e.g, cancer treatment or accidental), cancers (e.g., malignant blood cancers), and genetic blood disorders. For example, HSC can be administered to reconstitute the immune systems of individuals following radiation exposure. In individuals with malignant blood cancers, HSC can be used as transplants. In this use, the existing malignant hematopoietic system of an individual is ablated and HSC are provided as a therapeutic treatment to generate a properly functioning hematopoietic system. This transplant/therapeutic approach can also be used to treat a variety of genetic blood disorders and infections as described in more detail elsewhere herein. In various therapeutic uses of HSC, it can be beneficial to isolate primitive hematopoietic stem cell (pHSC) specifically and to genetically-modify these HSC to provide corrected cellular function.

In the clinical and therapeutic setting, the current gold standard for isolation of HSC is through the use of molecules that bind to the CD34 protein on the cellular surface of HSC. Singular use of the CD34 HSC cell surface marker, however, leads to a mixed or heterogeneous population of cells that have distinct phenotypes and characteristics because cells in addition to the most primitive HSC express CD34, including downstream progenitor cells. Due to the heterogeneity of these cell populations, there are several major limitations with using CD34 to identify HSCs. For example, the numbers of CD34-expressing cells isolated from blood and bone marrow products require large volumes of reagents for manipulation, which can be cost prohibitive if genetic manipulation of the HSCs is required. Thus, the field has widely recognized that there continues to be an unmet need to identify a more enriched, true (i.e., most primitive) HSC population, as well as methods to expand these cell populations for therapeutic uses.

As indicated, while HSCs are administered for therapeutic purposes, in many treatment regimens it is important to remove existing HSCs within a patient before the therapeutic administration. For example, hematopoietic stem cell transplant (HSCT) is primarily indicated to treat malignancies and blood disorders and requires intensive conditioning of a patient's tissues (e.g., bone marrow tissue) to remove existing HSCs prior to engraftment of the therapeutic HSC. Current non-targeted conditioning methods include, for example, irradiation (e.g., total body irradiation (TBI)) and DNA alkylating/modifying agents. These conditioning methods are highly toxic to multiple organ systems, and completely wipe out the hematopoietic and immune systems, frequently leading to life-threatening complications precluding the use of HSCT for less dire, but still severe, conditions such as autoimmune diseases.

Thus, there is significant room for improvement in the ability to prepare pHSC populations, ablate pHSC populations in vivo, and modify pHSC populations for therapeutic uses.

SUMMARY OF THE DISCLOSURE

The current disclosure addresses many drawbacks of the prior art. First, the current disclosure describes use of luteinizing hormone/choriogonadotropin receptor (LHR) binding agents and luteinizing hormone agonists to isolate, enrich and/or expand stem cell populations including the most primitive populations of human hematopoietic stem cells (pHSC). Using highly purified pHSC populations reduces the heterogeneity of cell populations providing more pure and homogenous therapeutic cell populations with stem cell capability for expansion and use. In particular embodiments, LHR binding agents can be used to enrich for and isolate pHSC. In particular embodiments, LH agonists can be used to expand pHSC.

Additionally, the current disclosure provides targeting LHR-expressing HSC for selective ablation during conditioning before a HSC transplant and/or genetic cell therapy. The described targeted and selective ablation reduces undesirable toxicity and minimizes the incidence of serious adverse reactions observed with currently utilized non-targeted conditioning methods. Moreover, selective ablation of HSC from HSC microenvironments (i.e., the HSC niche) opens the niche for the engraftment of donor stem cells. The efficiency of engraftment can be significantly enhanced by selective ablation, as compared to engraftment without selective ablation.

In particular embodiments, the current disclosure provides targeting LHR-expressing hyperproliferative HSC. Such embodiments can be used to treat malignancies associated with hyperproliferative HSC, such as hematopoietic cancers. These treatments can be performed independently of or in conjunction with selective ablation during conditioning before a HSC transplant or infusion of genetically modified cells.

Particular embodiments directed to the ablation of HSC can utilize LHR binding agents that result in selective ablation of LHR-expressing HSC. Examples of LHR binding agents include, for example, an LHR-binding antibody conjugated to a toxin, a bi-specific antibody, an LHR-binding bispecific T cell engaging (BiTE) antibody, or a chimeric antigen receptor (CAR)-modified immune cell.

BRIEF DESCRIPTION OF THE FIGURES

FIGS. 5A-5D. (5A) Cell populations and phenotypes. (5B) LHCGR expression pattern in HSCPs derived from female mice. (5C) LHCGR expression was a peculiarity of LT-HSCs with little or no expression found on purified BM stromal cells. (5D) These findings were consistent with publicly accessible gene expression databases.

FIGS. 10A-10D. LH-CAR redirects T cells to kill primary mouse Leydig testis cell tumors cell lines and LHCGR-transduced C1498 leukemia. (10A) Chimeric antigen receptor (CAR) designed based on natural ligand for the LHCGR receptor (luteinizing hormone) comprised by glycoprotein hormones alpha chain, linker, and luteinizing hormone beta subunit (10A, left panel was used to generate described experimental results). (10B) Mouse T cells were transduced with a retrovirus encoding myc tagged mouse LH-CAR containing CD28 costimulatory domain and CD3 zeta followed by a Thy1.1 reporter. Flow cytometry demonstrated co-expression of myc tag (CAR) and Thy1.1 reporter gene. (10C) Mouse T cells were transduced with the LH-CAR or mock transduced and incubated overnight with firefly luciferase-transduced MLTC1 and MA10 Leydig cell lines expressing LHCGR. Viable targets were assessed via luciferase assay. (10D) Mouse T cells were transduced with the LH-CAR or mock transduced and incubated overnight with firefly luciferase-transduced C1498 leukemia cell line also transduced to express LHCGR. Viable targets were assessed via luciferase assay after three days of co-culture.

FIG. 11. Luteinizing hormone receptor sequences (SEQ ID NOs: 1-3).

FIG. 12. Signaling domain including a variant of CD3 zeta and a portion of the 4-1BB intracellular signaling domain (DNA (SEQ ID NO: 4) and protein (SEQ ID NO: 5).

FIGS. 13A, 13B. LH-CAR. (13A) Mouse LH-CAR cDNA (SEQ ID NO: 6), Mouse LH-CAR translation (SEQ ID NO: 7) and subcomponents thereof including signal peptide (SEQ ID NO: 8), LH beta subunit (SEQ ID NO: 9), linker (SEQ ID NO: 10), LH alpha subunit (SEQ ID NO: 11), Myc (SEQ ID NO: 12), CD8 hinge (SEQ ID NO: 13), CD8 transmembrane domain (SEQ ID NO: 14), CD28 cytoplasmic (SEQ ID NO: 15), CD3 zeta (SEQ ID NO: 16), 2A (SEQ ID NO: 17), and Thy1.1 (SEQ ID NO: 18); (13B) human LH-CAR cDNA (SEQ ID NO: 19), human LH-CAR translation (SEQ ID NO: 20) and subcomponents thereof including signal peptide (SEQ ID NO: 21), LH beta subunit (SEQ ID NO: 22), linker (SEQ ID NO: 10), LH alpha subunit (SEQ ID NO: 23), Myc (SEQ ID NO: 12), CD28 hinge (SEQ ID NO: 24), CD28 transmembrane domain: (SEQ ID NO: 25), 4-1BB (SEQ ID NO: 26), and CD3 zeta (SEQ ID NO: 27).

DETAILED DISCLOSURE

Figure 1A:
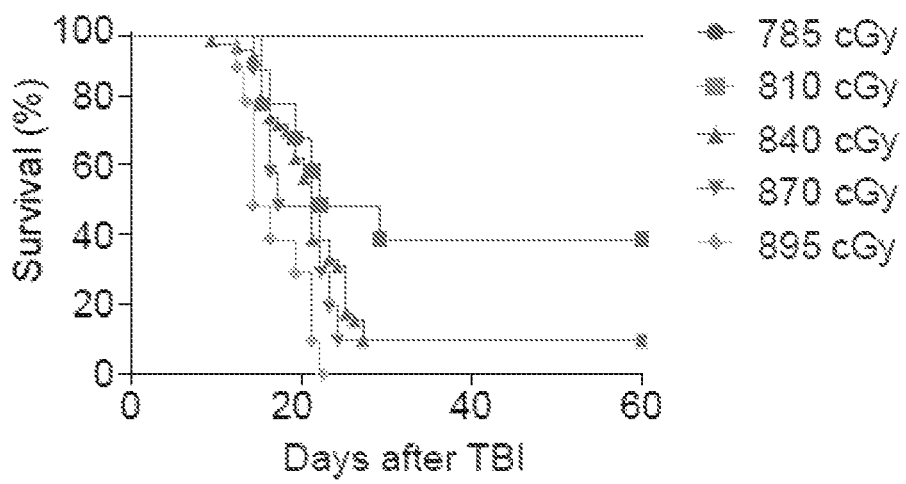
FIGS. 1A-1D. (1A) A lethal total body irradiation (L-TBI) dose of 840 cGy mediated lethality in more than 90% of mice. (1B) Mouse lethality was a result of bone marrow failure, as transplant of BM Lin$^-$Sca1$^+$ckit$^+$ (LSK) cells 3 days after L-TBI completely rescued all mice. (1C) Treatment of the mice 24 h and 15 days after L-TBI did not significantly enhance the survival benefit. (1D) A statistically significant benefit in survival in female mice given LHRH-Ant was also found.

There is significant room for improvement in the ability to prepare homogenous primitive hematopoietic stem cell (pHSC) populations, ablate pHSC populations in vivo, and modify pHSC populations for therapeutic uses.

The current disclosure provides improvements through the use of luteinizing hormone/choriogonadotropin receptor (LHR) binding agents to generate populations of the most primitive populations of human stem cells; use of LH agonists to promote HSC expansion; targeting LHR-expressing HSC for selective ablation during conditioning before a HSC transplant and/or infusion of genetically modified cells; and/or as an independent or complementary treatment to ablate hyperproliferative HSC associated with hematopoietic cancers. Particular embodiments may also use LH agonists to enhance HSC transfection/transduction in treatments utilizing genetic modification. Each of these aspects of the current disclosure are now described in more detail.

I. Use of the Luteinizing Hormone/Choriogonadotropin Receptor (LHR) Binding Agents to Isolate/Enrich for Primitive Populations of Human or Mouse Stem Cells. Stem cells are defined by their ability to form multiple cell types (multipotency) and their ability to self-renew. Hematopoietic stem cells (HSC) refer to stem cells that can differentiate into the hematopoietic lineage and give rise to all blood cell types such as white blood cells and red blood cells, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells).

The current disclosure provides use of the luteinizing hormone/choriogonadotropin receptor (LHR) binding agents to generate and expand populations of human and mouse pHSC including: human HSC1 and/or HSC2 and mouse long-term HSCs (LT-HSCs). In addition to expression of LHR (which is nearly absent on multipotent progenitors (MPPs) and multi-lymphoid progenitors (MLPs)), in particular embodiments, human HSC1 can be identified by the following profile: CD34+/CD38−/CD45RA−/CD90+ or CD34+/CD45RA−/CD90+ and mouse LT-HSC can be identified by Lin−Sca1+ckit+CD150+CD48−Flt3−CD34− (where Lin represents the absence of expression of any marker of mature cells including CD3, Cd4, CD8, CD11b, CD11c, NK1.1, Gr1, and TER119). Thus, HSC1 can include the marker profile: LHR+/CD34+/CD38−/CD45RA−/CD90+. In addition to expression of LHR, in particular embodiments, HSC1 can be identified by the following profile: Lin−/CD34+/CD38−/CD45RA−/CD90+/CD49f+. Thus, HSC1 can include the marker profile: LHR+/Lin−/CD34+/CD38−/CD45RA−/CD90+/CD49f+. In addition to expression of LHR, in particular embodiments, HSC2 can be identified by the following profile: CD34+/CD38−/CD45RA−/CD90−/CD49f+. Thus, HSC2 can include the marker profile: LHR+/CD34+/CD38−/CD45RA−/CD90−/CD49f+. Based on the foregoing profiles, expression of LHR can be combined with presence or absence of the following one or more markers to prepare HSC1 and/or HSC2 cell populations: Lin/CD34/CD38/CD45RA/CD90/CD49f as well as CD133. Various other combinations may also be used so long as the marker combination reliably isolates HSC1 or HSC2.

Sources of HSC to generate pHSC populations include cord blood, mobilized peripheral blood and bone marrow. Methods regarding collection, anti-coagulation and processing, etc. of blood samples are well known in the art. See, for example, Alsever et al., 1941, N.Y. St. J. Med. 41:126; De Gowin, et al., 1940, J. Am. Med. Ass. 114:850; Smith, et al., 1959, J. Thorac. Cardiovasc. Surg. 38:573; Rous and Turner, 1916, J. Exp. Med. 23:219; and Hum, 1968, Storage of Blood, Academic Press, New York, pp. 26-160.

HSC in peripheral blood are preferably mobilized prior to collection. Peripheral blood HSC can be mobilized by any method. Peripheral blood HSC can be mobilized by treating the subject with any agent(s), described herein or known in the art, that increase the number of HSC circulating in the peripheral blood of the subject. For example, in particular embodiments, peripheral blood is mobilized by treating the subject with one or more cytokines or growth factors (e.g., G-CSF, kit ligand (KL), IL-I, IL-7, IL-8, IL-11, Flt3 ligand, SCF, thrombopoietin, or GM-CSF (such as sargramostim)). Different types of G-CSF that can be used in the methods for mobilization of peripheral blood include filgrastim and longer acting G-CSF-pegfilgrastim. In particular embodiments, peripheral blood is mobilized by treating the subject with one or more chemokines (e.g., macrophage inflammatory protein-1α (MIP1α/CCL3)), chemokine receptor ligands (e.g., chemokine receptor 2 ligands GROβ and GROβ$_{Δ4}$), chemokine receptor analogs (e.g., stromal cell derived factor-1α (SDF-1α) protein analogs such as CTCE-0021, CTCE-0214, or SDF-1α such as Met-SDF-Iβ), or chemokine receptor antagonists (e.g., chemokine (C-X-C motif) receptor 4 (CXCR4) antagonists such as AMD3100).

In particular embodiments, peripheral blood is mobilized by treating the subject with one or more anti-integrin signaling agents (e.g., function blocking anti-very late antigen 4 (VLA-4) antibody, or anti-vascular cell adhesion molecule 1 (VCAM-1)).

In particular embodiments, peripheral blood is mobilized by treating the subject with one or more cytotoxic drugs such as cyclophosphamide, etoposide or paclitaxel.

In particular embodiments, peripheral blood can be mobilized by administering to a subject one or more of the agents listed above for a certain period of time. For example, the subject can be treated with one or more agents (e.g., G-CSF) via injection (e.g., subcutaneous, intravenous or intraperitoneal), once daily or twice daily, for 1, 2, 3, 4, 5, 6, 7, 8, 9, 10, 11, 12, 13 or 14 days prior to collection of HSC. In specific embodiments, HSC are collected within 1, 2, 3, 4, 5, 6, 7, 8, 12, 14, 16, 18, 20 or 24 hours after the last dose of an agent used for mobilization of HSC into peripheral blood. In particular embodiments, HSC are mobilized by treating the subject with two or more different types of agents described above or known in the art, such as a growth factor (e.g., G-CSF) and a chemokine receptor antagonist (e.g., CXCR4 receptor antagonist such as AM D3100), or a growth factor (e.g., G-CSF or KL) and an anti-integrin agent (e.g., function blocking VLA-4 antibody). In particular embodiments, different types of mobilizing agents are administered concurrently or sequentially. For additional information regarding methods of mobilization of peripheral blood see, e.g., Craddock et al., 1997, Blood 90(12):4779-4788; Jin et al., 2008, Journal of Translational Medicine 6:39; Pelus, 2008, Curr. Opin. Hematol. 15(4):285-292; Papayannopoulou et al., 1998, Blood 91(7):2231-2239; Tricot et al., 2008, Haematologica 93(11):1739-1742; and Weaver et al., 2001, Bone Marrow Transplantation 27(2): S23-S29).

HSC from peripheral blood can be collected from the blood through a syringe or catheter inserted into a subject's vein. For example, in particular embodiments, the peripheral blood can be collected using an apheresis machine. Blood flows from the vein through the catheter into an apheresis machine, which separates the white blood cells, including HSC from the rest of the blood and then returns the remainder of the blood to the subject's body. Apheresis can be performed for several days (e.g., 1 to 5 days) until enough HSC have been collected.

HSC from bone marrow can be obtained, e.g., directly from bone marrow from the posterior iliac crest by needle aspiration (see, e.g., Kodo et al., 1984, J. Clin Invest. 73:1377-1384), or from the blood following pre-treatment with cytokines (such as G-CSF and/or AMD3100) that induce cells to be released from the bone marrow compartment.

Enrichment/isolation of pHSC can be performed using any appropriate technique that is not unduly detrimental to the viability of the enriched for/isolated cells. Examples include magnetic separation using, for example, antibody-coated magnetic beads; fluorescence activated cell sorting (FACS; Williams et al., 1985, J. Immunol. 135:1004; Lu et al., 1986, Blood 68(1):126-133); affinity chromatography; cytotoxic agents joined to a monoclonal antibody or used in conjunction with a monoclonal antibody, e.g., complement and cytotoxins; "panning" with antibody attached to a solid matrix, e.g., plate, or other convenient technique (Broxmeyer et al., 1984, J. Clin. Invest. 73:939-953), agglutination using a lectin such as soybean (Reisner et al., 1980, Proc. Natl. Acad. Sci. U.S.A. 77:1164); etc.

Enrichment/isolation thus refers to a process wherein the percentage of target cells (i.e., HSC1 and/or HSC2 for human samples; LT-HSCs and ST-HSCs for mouse samples) in the sample is increased (relative to the percentage in the sample before the enrichment/isolation procedure). In particular embodiments, the increase in the number of target cells is an increase in the percentage of target cells in the enriched sample, relative to the sample prior to the enrichment/isolation procedure, for example at least a 25-, 50-, 75-, 100-, 150, 200-, 250-, 300-, 350-fold increase. In particular embodiments, LHR+HSC1 and/or LHR+HSC2 human cells, or LHR+LT-HSGs and/or LHR+ST-HSCs mouse cells, are enriched for/isolated using a binding agent specific for LHR, which binding agent is conjugated to a magnetic bead, and a magnetic cell separation device to separate out the LHR+HSC1 and/or LHR+HSC2 cells. As indicated, binding agents for other pHSC markers can also be used in combination with LHR (e.g., LHR+/CD34+; LHR+/CD34+/CD38−/CD45RA−/CD90+; LHR+/Lin−/CD34+/CD38−/CD45RA−/CD90+/CD49f; LHR+/CD34+/CD38−/CD45RA−/CD90−/CD49f+). In particular embodiments, using anti-LHR binding agents in combination with other HSC1 and/or HSC2 markers (or LHR+LT-HSGs and/or LHR+ST-HSGs mouse cells), results in target cells enriched to >80% of the population; >85% of the population; >90% of the population; >95% of the population; >99% of the population; or 100% of the population.

In particular embodiments, binding agents to assist in the preparation of pHSC populations include the LH alpha subunit and the LH beta subunit. The alpha subunit includes DCPECTLQENP FFSQPGAPILQCMGCCFSRAYPTPLR-SKKTMLVQKNVTSESTCCVAKSYN-RVTVMGGFKVENHTA CHCSTCYYHKS (SEQ ID NO: 23 (human)) or GCPECKLKENKYFSKLGAPIYQCM GCCFSR AYPTPARSKKTMLVPKNITSEATC CVAK AFTKATVMGNARVENHTECHCSTCYYHKS (SEQ ID NO: 11 (mouse)). In particular embodiments, the LH beta subunit includes SREPLRPWCHPINAILAVE KEG-CPVCITVNTTICAGYCPTMMRVLQAVLPPLPQVVC-TYRDVRFESIRLPGCPRGVDPVVSFPVALSCRCGPCR-RSTSDCGGPKDHPLTCDHPQLSGLLFL (SEQ ID NO: 22 (human)) or SRGPLRPLCRP VNATLAAENEFCPVC-ITFTTSICAGYCPSMVRVLPAALPPVPQPVCTYRELR-FASVRLPGCPPGVDP IVSFPVALSCRCGPCRLSSS-DCGGPRTQPMACDLPHLPGLLLL (SEQ ID NO: 9 (mouse)).

In particular embodiments, binding agents to assist in the preparation of pHSC populations include antibodies or binding fragments thereof. Numerous antibodies that bind LHR or other HSC1/HSC2 markers are commercially available. For example, anti-LHR antibodies are commercially available from Abcam, Invitrogen, Alomone Labs, Novus Biologicals, Origene Technologies, Bio-Rad, Abbexa, St. John's Laboratory, Millipore Sigma, LifeSpan Biosciences, etc.

Anti-LHR antibodies utilized or produced according to the methods disclosed herein have high affinity for LHR. The same is true for antibodies that bind to other HSC1 and/or HSC2 markers. In particular embodiments "affinity" refers to the strength of the sum total of noncovalent interactions between a single binding site of an antibody and its target marker. Unless indicated otherwise, "binding affinity" refers to intrinsic binding affinity which reflects a 1:1 interaction between members of a binding pair (i.e., antibody and target marker). The affinity of an antibody for its target marker can generally be represented by the dissociation constant (Kd) or the association constant ($K_A$). Affinity can be measured by common methods known in the art.

In particular embodiments, binding affinities can be assessed in relevant in vitro conditions, such as a buffered salt solution approximating physiological pH (7.4) at room temperature or 37° C.

In particular embodiments, "bind" means that the antibody associates with its target marker with a dissociation constant (1(D) of $10^{-8}$ M or less, in particular embodiments of from $10^{-5}$ M to $10^{-13}$ M, in particular embodiments of from $10^{-5}$ M to $10^{-10}$ M, in particular embodiments of from $10^{-5}$ M to $10^{-}$ M, in particular embodiments of from $10^{-8}$ M to $10^{-13}$ M, or in particular embodiments of from $10^{-9}$ M to $10^{-13}$ M. The term can be further used to indicate that the antibody does not bind to other biomolecules present, (e.g., it binds to other biomolecules with a dissociation constant (KD) of $10^{-4}$ M or more, in particular embodiments of from $10^{-4}$ M to 1 M).

In particular embodiments, "bind" means that the antibody associates with its target marker with an affinity constant (i.e., association constant, $K_A$) of $10^7$ $M^{-1}$ or more, in particular embodiments of from $10^5$ $M^{-1}$ to $10^{13}$ $M^{-1}$, in particular embodiments of from $10^5$ $M^{-1}$ to $10^{10}$ $M^{-1}$, in particular embodiments of from $10^5$ $M^{-1}$ to $10^8$ $M^{-1}$, in particular embodiments of from $10^7$ $M^{-1}$ to $10^{13}$ $M^{-1}$, or in particular embodiments of from $10^7$ $M^{-1}$ to $10^8$ $M^{-1}$. The term can be further used to indicate that the antibody does not bind to other biomolecules present, (e.g., it binds to other biomolecules with an association constant ($K_A$) of $10^4$ $M^{-1}$ or less, in particular embodiments of from $10^4$ $M^{-1}$ to 1 $M^{-1}$).

Naturally occurring antibody structural units include a tetramer. Each tetramer includes two pairs of polypeptide chains, each pair having one light chain and one heavy chain.

The amino-terminal portion of each chain includes a variable region that is responsible for target marker recognition and epitope binding. The variable regions exhibit the same general structure of relatively conserved framework regions (FR) joined by three hyper variable regions, also called complementarity determining regions (CDRs). The CDRs from the two chains of each pair are aligned by the framework regions, which enables binding to a specific target marker epitope. From N-terminal to C-terminal, both light and heavy chain variable regions include the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk, J. Mol. Biol., 196:901-917 (1987); Chothia et al., Nature, 342:878-883 (1989).

Within full-length light and heavy chains, the variable and constant regions are joined by a "J" region of amino acids, with the heavy chain also including a "D" region of amino acids. See, e.g., Fundamental Immunology, Ch. 7 (Paul, W., ed., 2nd ed. Raven Press, N.Y. (1989)).

Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, IgG1, IgG2, IgG3, and IgG4. IgA is similarly subdivided into subclasses including IgA1 and IgA2.

CDRs from antibodies that bind target markers can be utilized to aid in the preparation of pHSC populations in a variety of binding domain formats. For example, particular embodiments can include binding fragments of an antibody, e.g., Fv, Fab, Fab', F(ab')$_2$, Fc, and single chain Fv fragments (scFvs) or any effective binding fragments of an antibody that bind specifically to the targeted marker.

A single chain variable fragment (scFv) is a fusion protein of the variable regions of the heavy and light chains of immunoglobulins connected with a short linker peptide. Fv fragments include the $V_L$ and $V_H$ domains of a single arm of an antibody, but lack the constant regions. Although the two domains of the Fv fragment, $V_L$ and $V_H$, are coded by separate genes, they can be joined, using, for example, recombinant methods, by a synthetic linker that enables them to be made as a single protein chain in which the $V_L$ and $V_H$ regions pair to form monovalent molecules (single chain Fv (scFv)). For additional information regarding Fv and scFv, see e.g., Bird, et al., Science 242 (1988) 423-426; Huston, et al., Proc. Natl. Acad. Sci. USA 85 (1988) 5879-5883; Plueckthun, in The Pharmacology of Monoclonal Antibodies, vol. 113, Rosenburg and Moore (eds.), Springer-Verlag, N.Y.), (1994) 269-315; WO1993/16185; U.S. Pat. Nos. 5,571,894; and 5,587,458.

A Fab fragment is a monovalent antibody fragment including $V_L$, $V_H$, CL and CH1 domains. A F(ab')$_2$ fragment is a bivalent fragment including two Fab fragments linked by a disulfide bridge at the hinge region. Diabodies include two epitope-binding sites that may be bivalent. See, for example, EP 0404097; WO1993/01161; and Holliger, et al., Proc. Natl. Acad. Sci. USA 90 (1993) 6444-6448. Dual affinity retargeting antibodies (DART™; based on the diabody format but featuring a C-terminal disulfide bridge for additional stabilization (Moore et al., Blood 117, 4542-51 (2011))) can also be formed. Antibody fragments can also include isolated CDRs. For a review of antibody fragments, see Hudson, et al., Nat. Med. 9 (2003) 129-134.

Unless otherwise indicated, the term "antibody" includes antibodies including two full-length heavy chains and two full-length light chains, the fragments as described above, and variants described more fully below. Furthermore, unless explicitly excluded, antibodies can include monoclonal antibodies, human or humanized antibodies, bispecific antibodies, polyclonal antibodies, linear antibodies, minibodies, domain antibodies, synthetic antibodies, chimeric antibodies, antibody fusions, and fragments thereof, respectively.

A monoclonal antibody refers to an antibody obtained from a population of substantially homogeneous antibodies, i.e., the individual antibodies including the population are identical and/or bind the same target marker epitope, except for possible variant antibodies, e.g., containing naturally occurring mutations or arising during production of a monoclonal antibody preparation, such variants generally being present in minor amounts. In contrast to polyclonal antibody preparations, which include different antibodies directed against different epitopes of an antigen, each monoclonal antibody of a monoclonal antibody preparation is directed against a single epitope on an antigen. Thus, the modifier "monoclonal" indicates the character of the antibody as being obtained from a substantially homogeneous population of antibodies, and is not to be construed as requiring production of the antibody by any particular method. For example, monoclonal antibodies can be made by a variety of techniques, including the hybridoma method, recombinant DNA methods, and methods utilizing transgenic animals containing all or part of the human immunoglobulin loci.

In particular embodiments, an anti-LHR binding agent includes a CDRH1 including GYSITSGYG (SEQ ID NO:

28); a CDRH2 including IHYSGST (SEQ ID NO: 29); a CDRH3 including ARSLRY (SEQ ID NO: 30); and a CDRL1 including SSVNY (SEQ ID NO: 31); a CDRL2 including DTS; and a CDRL3 including HQWSSYPYT (SEQ ID NO: 32).

In particular embodiments, an anti-LHR binding agent includes a CDRH1 including GFSLTTYG (SEQ ID NO: 33); a CDRH2 including IWGDGST (SEQ ID NO: 34); and a CDRH3 including AEGSSLFAY (SEQ ID NO: 35); and a CDRL1 including QSLLNSGNQKNY (SEQ ID NO: 36); a CDRL2 including WAS; and a CDRL3 including QNDYSYPLT (SEQ ID NO: 37).

In particular embodiments, an anti-LHR binding agent includes a CDRH1 including GYSFTGYY (SEQ ID NO: 38); a CDRH2 including IYPYNGVS (SEQ ID NO: 39); and a CDRH3 including ARERGLYQLRAMDY (SEQ ID NO: 40); and a CDRL1 including QSISNN (SEQ ID NO: 41); a CDRL2 including NAS; and a CDRL3 including QQSNSWPYT (SEQ ID NO: 42).

In particular embodiments, an anti-LHR binding agent includes a heavy chain including EVQLQESGPDLVKPSQSLSLTCTVTGYSITSGYGWHRQFPGNKLEWMGYIHYSGSTTYNPSLKSRI SISRDTSKNQFFLQLNSVTTEDTATYYCARSLRYWGQGTTLTVSS (SEQ ID NO: 43) and a light chain including DIVMTQTPAIMSASPGQKVTITCSASSSVNYMHVVYQQKLGSSPKLWIY DTSKLAPG VPARFSGSGSGTSYSLTISSMEAEDAASYFCHQWSSYPYTFGSGTKLEIK (SEQ ID NO: 44).

In particular embodiments, an anti-LHR binding agent includes a heavy chain including QVQLKESGPGLVAPSQSLSrrCTVSGFSLTTYGVSVVVRQPPGKGLEWLGVIWGDGSTYYHSALISR LSISKDNSKSQVFLKLNSLQTDDTATYYCAEGSSLFAYWGQGTLVTVSA (SEQ ID NO: 45) and a light chain including DIVMTQSPSSLTVTAGEKVTMSCKSSQSLLNSGNQKNYLTWYQQKPGQPPKL LIYWASTRQSGVPDRFTGSG- SGTDFTLTISSVQAEDXAVYYCQNDYSYPLTFGSGTKLEIK (SEQ ID NO: 46).

In particular embodiments, an anti-LHR binding agent includes a heavy chain including EVQLEQSGGGLVQPGGSRKLSCAASGFTFSSFGMHWVRQAPEKGLEVVVAYISSGSSTLHYADTV KGRFTISRDNPKNTLFLQMKLPSLCYGLLGSRNLSHRLL (SEQ ID NO: 47) and a light chain including DIVLTQTPSSLSASLGDTITITCHASQNINVWLFVWYQQKPGNIPKLLIYKASNLLTGV- PSRFSGSGSGT GFTLTISSLQPEDIATYYCQQGQSFPWTFGGGTKLEIK (SEQ ID NO: 48).

In particular embodiments, an anti-LHR binding agent includes a heavy chain including QVKLQQSGPELVKPGASVKISCKASGYSFTGYYMHWVKQSHGNILDWIGYIYPYNGVSSYNQKFK GKATLTVDKSSSTAYMELRSLTSEDSAVYYCARERGLYQLRAMDYWGQGTSVTVSS (SEQ ID NO: 49) and a light chain including DIVLTQTPATLSVTPGDSVSLSCRASQSISNNLHWYQQKSHES PRLLIKNASQSISGIPSKFSGSGSGTDFTLRINSVETEDFGMYFCQQSNSWPYTFGSGTKLEIK (SEQ ID NO: 50).

II. Use of LH Agonists to Promote pHSC Expansion. Particular embodiments include expanding LHR+HSC1 and/or LHR+HSC2 cells (or LHR+LT-HSCs and/or LHR+ ST-HSCs mouse cells) by contacting the cells with an LH agonist to aid in the preparation of pHSC populations with sufficient numbers for a therapeutic use.

LH agonists include natural LH agonists and functional LH agonists. Natural LH agonists can include the native mammalian LH. The native mammalian LH is a gonadotropin secreted by the anterior lobe of the pituitary. LH is a heterodimer including non-covalently bound alpha and beta subunits. The alpha subunit is common among LH, FSH and hCG, and the beta subunit is specific for each hormone.

In particular embodiments, the LH agonist is LH (see, for example, U.S. Pat. No. 5,444,167). In particular embodiments, an LH agonist is recombinantly produced human LH. In particular embodiments, an LH agonist includes the sequence: EHWSYGLRPG (SEQ ID NO: 51).

In particular embodiments, a natural LH agonist is a protein which (1) includes a polypeptide that shares at least 90% sequence identity to the native human LH; and (2) possesses the biological activity of the native mammalian LH.

A functional LH agonist is a compound that binds to and activates LHR, although it does not necessarily share at least 90% sequence identity with LH. In particular embodiments, a functional LH agonist useful in the present disclosure may have the native alpha subunit, with the beta subunit having mutations. Alternatively, the LH may have the native beta subunit, with the alpha subunit having mutations. The functional LH agonist may also have both the alpha and beta subunit sharing a substantial sequence similarity with a native, corresponding subunit, but the entire sequence including less than 90% sequence identity with LH. Thus, in particular embodiments, LH analogs include a deletional, insertional, or substitutional mutants of a native LH subunit.

LH orthologues encompass LH from other species and the naturally occurring variants thereof.

LH and human chorionic gonadotropin (hCG) bind to the same LH receptor. In particular embodiments, hCG is used clinically as a surrogate for LH.

In particular embodiments, fresh LH can be added to culture conditions on a daily basis, every other day, every third day, or every fourth day at a dose of, for example, 0.05, 0.5, 5, 50 and/or 500 nM.

Particular embodiments include expansion in culture conditions including StemSpan supplemented with penicillin/streptomycin and 50-150 ng/ml (e.g., 100 ng/ml) stem cell factor (SCF; also known as the c-kit ligand or mast cell growth factor), thrombopoietin (TPO) and Flt-3 ligand (Flt-3L).

Additional culture conditions can include expansion in the presence of one more growth factors, such as: angiopoietin-like proteins (Angptls, e.g., Angptl2, Angptl3, Angptl7, Angptl5, and Mfap4); erythropoietin; fibroblast growth factor-1 (FGF-1); granulocyte colony stimulating factor (G-CSF); granulocyte-macrophage colony stimulating factor (GM-CSF); insulin growth factor-2 (IFG-2); interleukin-3 (IL-3); interleukin-6 (IL-6); interleukin-7 (IL-7); interleukin-11 (IL-11); and analogs thereof (wherein the analogs include any structural variants of the growth factors having the biological activity of the naturally occurring growth factor; see, e.g., WO 2007/1145227 and U.S. Patent Publication No. 2010/0183564).

In particular embodiments, the amount or concentration of growth factors suitable for expanding HSC is the amount or concentration effective to promote expansion of HSC, but substantially no differentiation of the HSC.

The amount or concentration of growth factors suitable for expanding HSC depends on the activity of the growth factor preparation, and the species correspondence between the growth factors and HSC, etc. Generally, when the growth factor(s) and HSC are of the same species, the total amount of growth factor in the culture medium ranges from 1 ng/ml to 5 µg/ml, from 5 ng/ml to 1 µg/ml, or from 5 ng/ml to 250 ng/ml. In additional embodiments, the amount of growth factors can be in the range of 5-1000 or 50-100 ng/ml.

In particular embodiments, the foregoing growth factors are present in the culture condition for expanding HSC at the following concentrations: 25-300 ng/ml SCF, 25-300 ng/ml Flt-3L, 25-100 ng/ml TPO, 25-100 ng/ml IL-6 and 10 ng/ml IL-3. In more specific embodiments, 50, 100, or 200 ng/ml SCF; 50, 100, or 200 ng/ml of Flt-3L; 50 or 100 ng/ml TPO; 50 or 100 ng/ml IL-6; and 10 ng/ml IL-3 can be used.

In particular embodiments, HSC expansion disclosed herein does not utilize an extracellular matrix protein such as fibronectin (FN), or a fragment thereof (e.g., CH-296 (Dao et. al., 1998, Blood 92(12):4612-21)) or RetroNectin® (a recombinant human fibronectin fragment; (Clontech Laboratories, Inc., Madison, Wis.). In particular embodiments, the culture system is a stroma-free culture system.

In particular embodiments, expansion results in (or more than) a 50-, 75-, 100- 150-, 200-, 250-, 300-, 350-, 400-, 450-, 500-, 1000-, 2000-, 3000-, 4000-, 5000-fold increase in the number of HSC in the expanded sample, relative to the unexpanded sample. In particular embodiments, cell populations are also preferably expanded until a sufficient number of cells are obtained to provide for at least one infusion into a human subject, typically around $10^4$ cells/kg to $10^9$ cells/kg or $2\times10^6$ cells/kg subject body weight.

For additional general information regarding appropriate culturing and/or expansion conditions, see U.S. Pat. No. 7,399,633; U.S. Patent Publication No. 2010/0183564; Freshney Culture of Animal Cells, Wiley-Liss, Inc., New York, N.Y. (1994)); Varnum-Finney et al., 1993, Blood 101:1784-1789; Ohishi et al., 2002, J. Clin. Invest. 110: 1165-1174; Delaney et al., 2010, Nature Med. 16(2): 232-236; WO 2006/047569A2; WO 2007/095594A2; U.S. Pat. No. 5,004,681; WO 2011/127470 A1; WO 2011/127472A1; and See Chapter 2 of Regenerative Medicine, Department of Health and Human Services, August 2006, and the references cited therein.

III. Targeting LHR-expressing pHSC for Selective Ablation During Conditioning Before a HSC Transplant and/or Infusion of Genetically Modified Cells and/or as a Treatment for Malignancies Associated with Hyperproliferative HSC. As indicated, for many therapeutic uses of HSCs it is beneficial to ablate a patient's existing HSC. Selective ablation of endogenous HSC can open a niche for the engraftment of therapeutic HSC without general ablation of cells in the tissue, such as that caused by radiation or chemotherapy. The more targeted ablation approach reduces the effects of such therapies on non-targeted cells and tissues, such as platelets, white blood cells and red blood cells as well as undesirable side effects upon other tissues (e.g. on cells of the gastrointestinal system, hair growth, and the increased risk of secondary malignancies). In particular embodiments, relative to traditional conditioning regimens, the methods disclosed herein do not induce neutropenia, thrombocytopenia and/or anemia and/or induces less neutropenia, thrombocytopenia and/or anemia than conditioning regimens currently used in the clinical setting. The reduced side effects associated with HSC ablation methods disclosed herein can be especially beneficial for pediatric patients.

In particular embodiments, selective ablation of endogenous HSC can provide a treatment for malignancies associated with hyperproliferative HSC, such as leukemias, lymphomas, and myelomas.

Particular embodiments utilize LHR binding agents that result in ablation of LHR-expressing pHSC. Particular embodiments include ablating pHSC within a niche. In mammals, endogenous HSC reside in the bone marrow, and thus ablative agents will reduce the numbers of pHSC resident in bone marrow.

"Ablate" and "ablation" generally refer to the partial or complete removal of a population of cells (e.g., HSC) from target tissues (e.g., bone marrow tissues of a subject). In particular embodiments, such ablation includes a complete removal or depletion of such cells from the target tissue. Alternatively, in other aspects, such ablation is a partial removal or depletion of such cells (e.g., HSCs) from the target tissue. For example, in particular embodiments, the methods disclosed herein result in at least 5%, 10%, 15%, 20%, 25%, 30%, 35%, 40%, 45%, 50%, 55%, 60%, 65%, 70%, 75%, 80%, 85%, 90%, 95%, 97.5%, 98% or 99% depletion of pHSC. In particular embodiments, ablation results in a pHSC reduction of at least 75%, at least 80% at least 90%, at least 95%, at least 99% or more.

In particular embodiments, LHR binding agents include anti-LHR antibodies conjugated to a toxin such as Saporin. As indicated previously, numerous anti-LHR antibodies are commercially available.

The carboxy-terminal portion of each antibody chain defines a constant region that can be responsible for effector function in vivo. Examples of effector functions include: C1q binding and complement dependent cytotoxicity (CDC); antibody-dependent cell-mediated cytotoxicity (ADCC); phagocytosis; down regulation of cell surface receptors (e.g. B cell receptors); and B cell activation.

Antibodies of interest for ablation may be tested for their ability to induce ADCC. Assays for apoptosis may be performed by the terminal deoxynucleotidyl transferase-mediated digoxigenin-11-dUTP nick end labeling (TUNEL) assay (Lazebnik et al., Nature: 371, 346 (1994)). Cytotoxicity may also be detected directly by detection kits known in the art, such as Cytotoxicity Detection Kit from Roche Applied Science (Indianapolis, Ind.). Preferably, the antibodies utilized within the present disclosure induce at least 10%, 20%, 30%, 40%, 50%, 60%, 80%, 90%, 95%, or 100% cytotoxicity of targeted pHSC.

Antibodies lacking fucose have been correlated with enhanced ADCC activity, especially at low doses of antibody. Methods of preparing fucose-less antibodies include growth in rat myeloma YB2/0 cells (ATCC CRL 1662). YB2/0 cells express low levels of FUT8 mRNA, which encodes an enzyme (α1,6-fucosyltransferase) necessary for fucosylation of polypeptides. Alternative embodiments for promoting cytotoxicity of cells with antibody treatment include antibody-mediated stimulation of signaling cascades resulting in cell death to the antibody bound cell. In addition, antibody-mediated stimulation of the innate immune system (e.g. through NK cells) may also result in the death of targeted LHR-expressing cells.

In particular embodiments of the disclosure, the antibody is of an isotype that can bind Fc receptors on macrophages and drive opsonization (Rashid et al., J. Immunol. 1992, 148:1382-1388). In particular embodiments, the antibody is of an IgG isotype, e.g. IgG1, IgG2, IgG3, IgG4, etc. In particular embodiments, the antibody is a rodent antibody of the IgG2b type. In other embodiments, the isotype is a human or humanized antibody of the IgG3 isotype (for review, see Davies and Metzger, Ann Rev Immunol 1983 1:87-117). Where a candidate antibody is of an isotype that does not bind Fc receptors and/or drive opsonization, the antibody may be modified through various methods known in the art to change the isotype to one that does bind Fc receptors and/or drive opsonization.

In particular embodiments for administration to humans, human antibodies can be used. A human antibody is one which includes an amino acid sequence which corresponds to that of an antibody produced by a human or a human cell or derived from a non-human source that utilizes human antibody repertoires or other human antibody-encoding sequences.

Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008). Human antibodies may be prepared by administering LHR (or a fragment thereof) to a transgenic animal that has been modified to produce intact human antibodies or intact antibodies with human variable regions in response to antigenic challenge. Such animals contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HUMAB technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Traditional strategies for hybridoma development using mice, llamas, chicken, rats, hamsters, rabbits, etc. can also be used.

If produced or utilized antibodies are not human, such antibodies can be humanized. A "humanized" antibody refers to a chimeric antibody including amino acid residues from non-human CDRs and amino acid residues from human FRs. In particular embodiments, a humanized antibody will include substantially all of at least one, and typically two, variable domains, in which all or substantially all of the CDRs correspond to those of a non-human antibody, and all or substantially all of the FRs correspond to those of a human antibody. A humanized antibody optionally may include at least a portion of an antibody constant region derived from a human antibody. A "humanized form" of an antibody, e.g., a non-human antibody, refers to an antibody that has undergone humanization.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include: framework regions selected using the "best-fit" method (see, e.g., Sims et al., J. Immunol. 151:2296 (1993)); framework regions derived from the consensus sequence of human antibodies of a particular subgroup of light or heavy chain variable regions (see, e.g., Carter et al., Proc. Nati. Acad. Sci. USA, 89:4285 (1992); and Presta et al., J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

A human consensus framework is a framework which represents the most commonly occurring amino acid residues in a selection of human immunoglobulin variable light ($V_L$) or variable heavy ($V_H$) framework sequences. Generally, the selection of human immunoglobulin $V_L$ or $V_H$ sequences is from a subgroup of variable domain sequences. The subgroup of sequences can be a subgroup as in Kabat et al., Sequences of Proteins of Immunological Interest, Fifth Edition, NIH Publication 91-3242, Bethesda Md. (1991), vols. 1-3. In particular embodiments, for the $V_L$, the subgroup is subgroup kappa I as in Kabat et al., supra. In particular embodiments, for the $V_H$, the subgroup is subgroup III as in Kabat et al., supra.

In particular embodiments, antibody variants have been modified from a reference sequence to produce an administration benefit. Exemplary administration benefits can include (1) reduced susceptibility to proteolysis, (2) reduced susceptibility to oxidation, (3) altered binding affinity for forming protein complexes, (4) altered binding affinities, (5) reduced immunogenicity; and/or (6) extended half-live. For discussion of Fab and F(ab')$_2$ fragments having increased in vivo half-life, see U.S. Pat. No. 5,869,046.

As indicated particular embodiments can utilize variants of anti-LHR antibodies. Variants of anti-LHR antibodies can include those having one or more conservative amino acid substitutions or one or more non-conservative substitutions that do not adversely affect the binding of the antibody to LHR.

In particular embodiments, a $V_L$ region can include one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared to an antibody produced and characterized according to methods disclosed herein. An insertion, deletion or substitution may be anywhere in the V$_L$ region, including at the amino- or carboxy-terminus or both ends of this region, provided that each CDR includes zero changes or at most one, two, or three changes and provided an antibody including the modified V$_L$ region can still specifically bind LHR with an affinity similar to the reference antibody.

In particular embodiments, a V$_H$ region can be derived from or based on a disclosed V$_H$ and can include one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with when compared to an antibody produced and characterized according to methods disclosed herein. An insertion, deletion or substitution may be anywhere in the V$_H$ region, including at the amino- or carboxy-terminus or both ends of this region, provided that each CDR includes zero changes or at most one, two, or three changes and provided an antibody including the modified V$_H$ region can still specifically bind its target epitope with an affinity similar to the reference antibody.

In particular embodiments, one or more amino acid modifications may be introduced into the Fc region of an antibody, thereby generating an Fc region variant. The Fc region variant may include a human Fc region sequence (e.g., a human IgG1 (EPKSCDKTHTCPPCP (SEQ ID NO: 52)), IgG2 (ERKCCVECPPCP (SEQ ID NO: 53)), IgG3 (ELKTPLGDTHTCPRCP (SEQ ID NO: 54); or IgG4 (ESKYGPPCPSCP (SEQ ID NO: 55)) Fc region) including an amino acid modification (e.g. a substitution) at one or more amino acid positions. Exemplary human IgG4 modifications include ESKYGPPCPPCP (SEQ ID NO: 56); YGPPCPPCP (SEQ ID NO: 57); KYGPPCPPCP (SEQ ID NO: 58); and EVVKYGPPCPPCP (SEQ ID NO: 59).

In particular embodiments for ablation, antibodies can be coupled to a toxin. Toxins can include molecules that inactivate ribosomes, inhibit RNA polymerase II and/or III, and/or inhibits protein synthesis. Toxins include anti-tubulin agents (e.g. maytansines) or tubulin inhibitors, DNA cross-linking agents, DNA alkylating agents and cell cycle or mitotic disrupters. Examples of toxins include abrin A chain, abrin toxin, amatoxin (e.g., α-amanitin, β-amanitin, γ-amanitin, ε-amanitin, amanin, amaninamide, amanullin, amanullinic acid), auristatin-E, crotin, curcin, diphtheria A chain, diphtheria toxin, enomycin, exotoxin A chain, gelonin toxin, luffin toxin, modeccin toxin, momordin toxin, phenomycin, pseudomonas exotoxin A, radiochemicals (e.g., radioisotopes), Ricin A chain, saporin, and trichosanthin toxin. Particular embodiments utilize saporin.

In particular embodiments, the toxic agent is a selective inhibitor of growth factor signaling required for stem cell maintenance or growth. Exemplary of such agents are those that inhibit c-kit mediated signaling, which is required for maintenance of HSC. Such agents include antibodies that bind to and interfere with c-kit signaling; and drugs that selectively inhibit c-kit signaling, e.g. imatinib, nilotinib, certain 5-substituted 1,4-dihydroindeno[1,2-c]pyrazoles, etc., as known in the art and discussed in, for example, WO03028711; WO/2005/115304; Bioorganic & Medicinal Chemistry Letters (2007) 17:3136-3140; and Chow et al., (2007) Leuk Lymphoma. 2007 48(7):1379-88.

In particular embodiments, CAR-modified immune cells can also be used as LHR binding agents to target LHR-expressing pHSC for ablation. In these embodiments, immune cells (e.g., T cells, natural killer cells) can be genetically modified with polynucleotides that express chimeric antigen receptors (CAR) to ablate LHR-expressing pHSC. CAR refer to synthetically designed receptors including at least a binding domain that binds LHR and an effector domain and optionally a spacer domain and/or a transmembrane domain. CAR-modified immune cells can mediate the ablation of cells bound by the CAR-binding domain.

CAR binding domains for LHR can be generated from the CDRs of existing or prepared anti-LHR antibodies and variants thereof as described above. In particular embodiments, CAR binding domains can include the LH alpha subunit and the LH beta subunit.

Effector domains are capable of transmitting functional signals to an immune cell. In particular embodiments, an effector domain will directly or indirectly promote a cellular response by associating with one or more other proteins that directly promote a cellular response. Effector domains can provide for activation of at least one function of a transduced lymphocyte expressing the CAR upon binding to LHR expressed on a targeted HSC. Activation of the lymphocyte can include one or more of proliferation, differentiation, activation or other effector functions.

An effector domain may include one, two, three or more receptor signaling domains, intracellular signaling domains, costimulatory domains, or combinations thereof. Any intracellular effector domain, costimulatory domain or both from any of a variety of signaling molecules (e.g., signal transduction receptors) may be used in the CARs for purposes described herein.

Exemplary effector domains include those from 4-1BB, CD3ε, CD3δ, CD3ζ, CD27, CD28, CD79A, CD79B, CARD11, DAP10, FcRα, FcRβ, FcRγ, Fyn, HVEM, ICOS, Lck, LAG3, LAT, LRP, NOTCH1, Wnt, NKG2D, OX40, ROR2, Ryk, SLAMF1, Slp76, pTα, TCRα, TCRβ, TRIM, Zap70, PTCH2, or any combination thereof.

In particular embodiments, 4-1BB includes KRGRKKL-LYIFKQPFMRPVQTTQEEDGCSCR FPEEEEGGCEL (SEQ ID NO: 26). Uniprot Q07011 provides 4-1BB including residues 1-23 (signal peptide); 24-186 (extracellular domain); 187-213 (transmembrane domain); and 214-255 (intracellular domain).

In particular embodiments, a CD28 signaling region includes MLRLLLALNLFPSIQ VTGNKILVKQSPM LVAYDNAVNLSCKYSYNLFSREFRASLHKGLDSAV EVCVVYGNYSQQLQVYSK TGFNCDGKLGNESV TF YLQNLYVNQTDIYFCKIEVMYPPPYLDNEKSNGTIIH VKGKHLCPSPLFPG PSKPFVVVLWVGGVLACYSLL-VTVAFIIFVVVRSKRSRLLHSDYMNMTPRRPGP-TRKHYQPYAPPRD FAAYRS (SEQ ID NO: 60). For reference, Uniprot P10747 includes CD28 including residues 1-18 (signal peptide); 19-152 (extracellular domain); 153-179 (transmembrane domain); and 180-220 (intracellular domain) wherein residues 186 and 187 can be LL or GG.

In particular embodiments, a CD3 zeta signaling region includes RVKFSRSADA PAYQQGQNQLYNELNLGR-REEYDVLDKRRGRDPEMGGKPRRKNPQEGLYNELQ KDKMAEAYSEI GMKGERRRGKGHDGLYQGLSTAT KDTYDALHMQALPPR (SEQ ID NO: 27).

In particular embodiments, a CD3 zeta signaling region includes AKFSRSAETAANLQ DPNQLYNELNLGR-REEYDVLEKKRARDPEMGGKQQRRRNPQEGVYNAL QKDKMAEAYSEIGTKG ERRRGKGHDGLYQGL-STATKDTYDALHMQTLAPR (SEQ ID NO: 16).

Uniprot P20963 provides human CD3 zeta isoform 3 including residues 1-21 (signal peptide); 22-30 (extracellular domain); 31-51 (transmembrane domain); 52-164 (intracellular domain); 61-89 (ITAM1); 100-128 (ITAM2); and 131-159 (ITAM3).

T cell activation particularly can be said to be mediated by two distinct classes of cytoplasmic signaling sequence: those that initiate antigen-dependent primary activation and provide a T cell receptor like signal (primary cytoplasmic signaling sequences) and those that act in an antigen-independent manner to provide a secondary or co-stimulatory signal (secondary cytoplasmic signaling sequences). Primary cytoplasmic signaling sequences that act in a stimulatory manner may contain signaling motifs which are known as receptor tyrosine-based activation motifs or iTAMs. Examples of iTAM containing primary cytoplasmic signaling sequences include those derived from CD3 zeta, FeR gamma, CD3 gamma, CD3 delta, CD3 epsilon, CD5, CD22, CD79a, CD79b, and CD66d. In particular embodiments, ITAM 1 refers to APAYQQGQNQLYNELNLGR-REEYDVLDKR (SEQ ID NO: 61); ITAM2 refers to PQRRKNPQEGLYNELQKDKMAEAYSEIGM (SEQ ID NO: 62); and ITAM3 refers to ERRRGKGHDGLYQGL-STATKDTYDALHMQ (SEQ ID NO: 63).

In particular embodiments, an effector domain includes a cytoplasmic portion that associates with a cytoplasmic signaling protein, wherein the cytoplasmic signaling protein is a lymphocyte receptor or signaling domain thereof, a protein including a plurality of ITAMs, a costimulatory factor, or any combination thereof.

Examples of intracellular signaling domains include the cytoplasmic sequences of the CD3 zeta chain, and/or co-receptors that act in concert to initiate signal transduction following CAR engagement, as well as any derivative or variant of these sequences and any synthetic sequence that has the same functional capability. In particular embodiments, an intracellular signaling domain of a CAR can be designed to include an intracellular signaling domain combined with any other desired cytoplasmic domain(s). For example, the intracellular signaling domain of a CAR can include an intracellular signaling domain and a costimulatory signaling region. The costimulatory signaling region refers to a portion of the CAR including the intracellular domain of a costimulatory molecule. A costimulatory molecule is a cell surface molecule other than the expressed marker ligand that is required for a response of lymphocytes to a marker. Examples of such molecules include CD27, CD28, 4-1BB (CD 137), OX40, CD30, CD40, lymphocyte function-associated antigen-1 (LFA-1), CD2, CD7, LIGHT, NKG2C, B7-H3, and a ligand that specifically binds with CD83.

In particular embodiments, CAR polynucleotides can include a sequence encoding for a spacer region. The length of the spacer region can be customized to optimize LHR recognition. In particular embodiments, a spacer length can be selected based upon the location of a marker epitope, affinity of an antibody for the epitope, and/or the ability of the lymphocytes expressing the CAR to proliferate in vivo in response to LHR recognition.

Typically, a spacer region is found between the binding domain and a transmembrane domain of the CAR. Spacer regions can provide for flexibility of the binding domain and allows for high expression levels in the modified cells. In particular embodiments, a spacer region can have at least 10 to 250 amino acids, at least 10 to 200 amino acids, at least 10 to 150 amino acids, at least 10 to 100 amino acids, at least 10 to 50 amino acids or at least 10 to 25 amino acids and including any integer between the endpoints of any of the listed ranges. In further embodiments, a spacer region has 250 amino acids or less; 200 amino acids or less, 150 amino acids or less; 100 amino acids or less; 50 amino acids or less; 40 amino acids or less; 30 amino acids or less; 20 amino acids or less; or 10 amino acids or less.

In particular embodiments, spacer regions can be derived from a hinge region of an immunoglobulin like molecule, for example all or a portion of the hinge region from a human IgG1, human IgG2, a human IgG3, or a human IgG4. In particular embodiments, a hinge region includes a CD8 hinge and/or a CD28 hinge.

An exemplary hinge sequence derived from the IgG1 heavy chain is encoded by CTCGAGCCCAAATCT TGTGACAAAACTCACACATGCCCACCGTGCCCG (SEQ ID NO: 64).

Exemplary CD8 hinge domains include AAASTTT KPVLRTPSPVHPTGTSQPQRPEDC RPRGSVKGTGLD-FACDIY (SEQ ID NO: 13); PAKPTTTPAPRPPTPAPTIA-SQPLSLRPEACRPAAG G AVHTRGLDFACDIY (SEQ ID NO: 65); KVNSTTTKPVLRTPSPVHPTG TSQPQRPE DCR PRG SVKGTGLDFACDIY (SEQ ID NO: 66); and PVKPTTTPAPRPPTQAPITTSQRVSLRPGTCQPSAGST VEASGLDLSCDIY (SEQ ID NO: 67).

An exemplary CD28 hinge includes AAAIEVMYPP-PYLDNEKSNGTIIHVKGKHLCPSPLFP GPSKP (SEQ ID NO: 24).

Hinge regions can be modified to avoid undesirable structural interactions such as dimerization. In particular embodiments, all or a portion of a hinge region can be combined with one or more domains of a constant region of an immunoglobulin. For example, a portion of a hinge region can be combined with all or a portion of a CH2 or CH3 domain or variant thereof. An example of an intermediate length spacer including an IgG4 hinge and a CH3 region includes ESKYGPPCPPCPGQPREPQVYTLPP-SQEEMTKNQVSLTCLVKGFYPSDIAVEWESNGQPE NNY KTTPPVLDSDGSFFLYSRLTVDKSRWQEGN VFSCSVMHEALHNHYTQKSLSLSLGK (SEQ ID NO: 68). An example of a longer spacer including an IgG4 hinge and a CH3 region includes ESKYGPPCPPCPAPEFLGG PSVFLFPPKPKDTLMISRTPEVTCVVVDVSQEDPE-VQFNWYVDGV EVHNAKTKPREEQFNSTYRVV SVL TVLHQDWLNGKEYKCKVSNKGLPSSIEKTISKAKG-QPREP QVYTLPPSQEEMTKNQVSLTCLVKGFYPS-DIAVEWESNGQPENNYKTTPPVLDSDGSFFLYSRL TV DKSRWQEGNVFSCSVMHEALHNHYTQKSLSLSLGK (SEQ ID NO: 69). For reference, Uniprot P0861 includes a IgG4-Fc with residues 1-98 (CH1), 99-110 (hinge), 111-220 (CH2), 221-327 (CH3) wherein residue 108 can be S or P.

CARs disclosed herein can also include transmembrane domains. In particular embodiments, the CAR polynucleotide encodes the transmembrane domain. The transmembrane domain provides for anchoring of the CAR in a lymphocyte membrane. The transmembrane domain may be derived either from a natural or a synthetic source. When the source is natural, the domain may be derived from any membrane-bound or transmembrane protein. Transmembrane regions include at least the transmembrane region(s) of) the alpha, beta or zeta chain of the T-cell receptor, CD8, CD28, CD3, CD45, CD4, CD6, CD9, CD16, CD22; CD33, CD37, CD64, CD80, CD86, CD134, CD137 and CD154. In particular embodiments, the CD8 transmembrane domain includes IWAPLAGICVALLLSLIITLI (SEQ ID NO: 14);

IYIWAPL AGTCGVLLLSLVIT (SEQ ID NO: 70); or IWAPLAGICAVLLLSLVITLI (SEQ ID NO: 71). In particular embodiments, the CD28 transmembrane domain includes FWVLVVVGGVLACY SLLVTVAFIIFWV (SEQ ID NO: 25).

In further particular embodiments, synthetic or variant transmembrane domains include predominantly hydrophobic residues such as leucine and valine.

CAR can also include linkers, tags, reporters, and/or expression modulators. A linker can be an amino acid sequence having from one up to 500 amino acids, which can provide flexibility and room for conformational movement between two regions, domains, motifs, cassettes or modules connected by the linker. Exemplary linker sequences include those having from one to ten repeats of $Gly_xSer_y$, wherein x and y are independently an integer from 0 to 10 provided that x and y are not both 0 (e.g., $(Gly_4Ser)_3$ (SEQ ID NO: 10), $(Gly_3Ser)_2$ (SEQ ID NO: 72), $Gly_2Ser$, or a combination thereof such as $(Gly_3Ser)_2Gly_2Ser)$(SEQ ID NO: 73). In certain other embodiments, a linker sequence can include one or more immunoglobulin heavy chain constant regions, such as a CH3 alone or a CH2CH3 sequence. In particular embodiments, a CH2 sequence includes (SEQ ID NO: 74)
APEFLGGPSVFLFPPKPKDTLMISRTPEVTCVVVDVSQEDPEVQFNWY

VDGVEVHNAKTKPREEQFNSTYRVVSVLTVLHQDWLNGKEYKCKVSNK

GLPSSIEKTISKAK and a CH3 sequence includes GQPREPQVYTLPPSQEEMTKNQVSLTCLVKGFYPSDIAVEWESNGQPENNYKTTPPVLDSDGSFF LYSRLTVDKSRWQEGNVFSCSVMHEALHNHYTQKSLSLSLGK (SEQ ID NO: 75).

Exemplary tags include Myc tag (EQKLISEEDL (SEQ ID NO:12)), Strep tag (which refers the original STREP® tag (WRHPQFGG (SEQ ID NO: 76)), STREP TAG® II (WSHPQFEK (SEQ ID NO: 77)), or any variant thereof; see, e.g., U.S. Pat. No. 7,981,632), His tag, Flag tag (DYKDDDDK (SEQ ID NO:78)), Xpress tag (DLYDDDDK (SEQ ID NO:79)), Avi tag (GLNDIFEAQKIEWHE (SEQ ID NO:80)), Calmodulin tag (KRRWKKNFIAVSAANRFKKISSSGAL (SEQ ID NO:81)), Polyglutamate tag, HA tag (YPYDVPDYA (SEQ ID NO:82)), Nus tag, S tag, SBP tag, Softag 1 (SLAELLNAGLGGS (SEQ ID NO:83)), Softag 3 (TQDPSRVG (SEQ ID NO:84)), V5 tag (GKPIPNPLLGLDST (SEQ ID NO:85)).

Particular embodiments can include 2A (GTGQCTNYALLKLAGDVESNPGPGS (SEQ ID NO: 17)); T2A (LEGGGEGRGSLLTCGDVEENPGPR (SEQ ID NO: 86)); T2A (GSG)EGRGSLLTCGD VEENPGP (SEQ ID NO: 87); P2A (GSG)ATNFSLLKQAGDVEENPGP (SEQ ID NO: 88); E2A (GSG) QCTNYALLKLAGDVESNPGPP (SEQ ID NO: 89); and F2A (GSG) VKQTLNFDLLKLAGDVESNPGP (SEQ ID NO: 90).

Particular examples of CAR protein sequences are provided in FIG. 13A (SEQ ID NO: 7) and FIG. 13B (SEQ ID NO: 20).

Methods to genetically modify immune cells to incorporate polynucleotides encoding functional CAR are described further below in relation to genetic modifications for therapeutic purposes. Particular examples of cDNA encoding CAR are provided in FIG. 13A (SEQ ID NO: 6) and FIG. 13B (SEQ ID NO: 19).

Particular embodiments modify pHSC populations enriched or expanded according to a method disclosed herein to express a CAR. In particular embodiments, the pHSC populations differentiate into a more committed cell line before or after the modification. In particular embodiments, the pHSC populations differentiate into a more committed cell line before or after administration to a subject.

In particular embodiments, T cells are genetically modified to express CAR. T cells can refer to all types of immune cells expressing CD3 including T-helper cells (CD4+ cells), cytotoxic T-cells (CD8+ cells), natural killer T-cells, T-regulatory cells (Treg) and gamma-delta T cells. Particular embodiments genetically modify beneficial combinations of T cell types, such as CD4+ T cells and CD8+ T cells.

In particular embodiments, T cells are derived from a pHSC population enriched or expanded according to a method disclosed herein. In particular embodiments, T cells modified to express a CAR are obtained from a subject who will receive the modified T cells as a treatment. In particular embodiments, T cells are autologous T cells. In particular embodiments, T cells include autologous and allogeneic primary patient cells.

Examples of commercially available T-cell lines include lines BCL2 (AAA) Jurkat (ATCC® CRL-2902™), BCL2 (S70A) Jurkat (ATCC® CRL-2900™), BCL2 (S87A) Jurkat (ATCC® CRL-2901™), BCL2 Jurkat (ATCC® CRL-2899™), Neo Jurkat (ATCC® CRL-2898™), TALL-104 cytotoxic human T cell line (ATCC #CRL-11386). Further examples include mature T-cell lines, e.g., such as Deglis, EBT-8, HPB-MLp-W, HUT 78, HUT 102, Karpas 384, Ki 225, My-La, Se-Ax, SKW-3, SMZ-1 and T34; and immature T-cell lines, e.g., ALL-SIL, Be13, CCRF-CEM, CML-T1, DND-41, DU.528, EU-9, HD-Mar, HPB-ALL, H-SB2, HT-1, JK-T1, Jurkat, Karpas 45, KE-37, KOPT-K1, K-T1, L-KAW, Loucy, MAT, MOLT-1, MOLT 3, MOLT-4, MOLT 13, MOLT-16, MT-1, MT-ALL, P12/Ichikawa, Peer, PER0117, PER-255, PF-382, PFI-285, RPMI-8402, ST-4, SUP-T1 to T14, TALL-1, TALL-101, TALL-103/2, TALL-104, TALL-105, TALL-106, TALL-107, TALL-197, TK-6, TLBR-1, -2, -3, and -4, CCRF-HSB-2 (CCL-120.1), J.RT3-T3.5 (ATCC TIB-153), J45.01 (ATCC CRL-1990), J.CaM1.6 (ATCC CRL-2063), RS4;11 (ATCC CRL-1873), CCRF-CEM (ATCC CRM-CCL-119); and cutaneous T-cell lymphoma lines, e.g., HuT78 (ATCC CRM-TIB-161), MJ[G11] (ATCC CRL-8294), HuT102 (ATCC TIB-162).

Particular embodiments modify natural killer cells (also known as NK cells and killer cells) cells to express CAR. NK cells are activated in response to interferons or macrophage-derived cytokines. They serve to contain viral infections while the adaptive immune response is generating antigen-specific cytotoxic T cells that can clear the infection. NK cells express CD8, CD16 and CD56 but do not express CD3. In particular embodiments, NK cells are genetically modified to express CAR. In particular embodiments, NK cells are derived from a pHSC population enriched or expanded according to a method disclosed herein. In particular embodiments, NK cells modified to express a CAR are obtained from a subject who will receive the modified NK cells as a treatment. In particular embodiments, NK cells are autologous NK cells. In particular embodiments, NK cells include autologous and allogeneic primary patient cells.

Examples of commercial NK cell lines include lines NK-92 (ATCC® CRL-2407™), NK-92MI (ATCC® CRL-2408™), HANK1, KHYG-1, NKL, NK-YS, NOI-90, and YT.

Particular embodiments may also utilize mixtures of pHSC, HSC, HSPC, T cells, and/or NK cells. In particular embodiments, some cells within a mixture are genetically modified and some are not. In particular embodiments, some classes of cells within a mixture are genetically modified and other classes are not.

As indicated, particular embodiments include use of an antibody directed against LHR wherein the antibody is conjugated to a toxin to clear HSCs from a niche. Particular embodiments include use of a CAR immune cell directed against LHR. HSC clearance from a niche improves subsequent engraftment of therapeutically-administered HSC. Thus, in particular embodiments, the present disclosure combines the use of selective ablation of endogenous HSC, in combination with the administration to the recipient of exogenous therapeutic HSC, resulting in efficient, long-term engraftment and tolerance.

Following ablation, and after a period of time sufficient to substantially eliminate the HSC ablative agent from the patient circulation, exogenous HSC are introduced to the patient, where the exogenous HSC occupy the same niche as the ablated endogenous HSC. Exogenous HSC may be autologous, allogeneic, or xenogeneic relative to the patient.

The period of time required for clearance of the ablative agent may be empirically determined, or may be based on prior experience of the pharmacokinetics of the agent. Where the agent is an antibody, determination can be conveniently monitored by containing HSC with recipient serum, and determining the presence of antibodies that bind to the HSC. Alternatively, patient serum may be monitored for the presence of HSC selective growth inhibition. The time for clearance is usually the time sufficient for the level of ablative agent to decrease at least 10-fold from peak levels, usually at least 100-fold, 1000-fold, 10,000-fold, or more. It is preferable to introduce the therapeutic HSC within the empty niche "window" following ablation, usually within 3 days, 2 days, 1 day, or at the time of clearance.

In particular embodiments, HSC are administered to the subject after the ablative agent has cleared or dissipated from the subject's target tissues such that the level of ablative agent remaining in the target tissue of the subject does not induce significant cell death in the transplanted HSC population. For example, in particular embodiments, the HSC population is administered to the subject two to eighteen days after the administration of the ablative agent.

As indicated previously, administered HSC can be genetically-modified or non-genetically modified. The following discussion of methods to genetically-modify HSC for a therapeutic purpose can also apply to genetically-modifying immune cells to express CAR.

In particular embodiments, administered HSC may be genetically altered in order to introduce genes useful in the differentiated cell, e.g. repair of a genetic defect in an individual, selectable marker, etc., or genes useful in selection against undifferentiated cells. Cells may also be genetically modified to enhance survival, control proliferation, and the like. Cells may be genetically altered by transfection or transduction with a suitable vector, homologous recombination, or other appropriate technique, so that they express a gene of interest. In particular embodiments, cells are transfected with genes encoding a telomerase catalytic component (TERT), typically under a heterologous promoter that increases telomerase expression beyond what occurs under the endogenous promoter, (see International Patent Application WO 98/14592). In particular embodiments, a selectable marker is introduced, to provide for greater purity of the desired differentiating cell. Cells may be genetically altered using vector containing supernatants over an 8-16 h period, and then exchanged into growth medium for 1-2 days. Genetically altered cells are selected using a drug selection agent such as puromycin, G418, or blasticidin, and then recultured.

Numerous techniques for the introduction of one or more genetic modifications into cells can be used, provided that the necessary developmental and physiological functions of the recipient cells are not disrupted. See e.g., Loeffler and Behr, 1993, *Meth. Enzymol.* 217:599-618; Cohen, et al., 1993, *Meth. Enzymol.* 217:618-644; Cline, 1985, *Pharmac. Ther.* 29:69-92). In particular embodiments, the technique should provide for the stable transfer of nucleic acid to the cell, so that the nucleic acid is expressible by the cell and preferably heritable and expressible by its cell progeny.

Exemplary methods include transfection, electroporation, microinjection, liposomes/lipofection (Tarahovsky and Ivanitsky, 1998, Biochemistry (Mosc) 63:607-618), ribozymes (Branch and Klotman, 1998, Exp. Nephrol. 6:78-83), calcium phosphate mediated transfection, infection with a viral or bacteriophage vector containing the gene sequences, cell fusion, chromosome-mediated gene transfer, microcell-mediated gene transfer, spheroplast fusion, administration of naked DNA, DNA complexes and/or triplex DNA (Chan and Glazer, 1997, J. Mol. Med. 75:267-282), transposons/transposases, etc.

A "vector" is a nucleic acid molecule that is capable of transporting another nucleic acid. Vectors may be, e.g., viruses, phage, a DNA vector, a RNA vector, a viral vector, a bacterial vector, a plasmid vector, a cosmid vector, and an artificial chromosome vector. An "expression vector" is any type of vector that is capable of directing the expression of a protein encoded by one or more genes carried by the vector when it is present in the appropriate environment.

Viral vectors are usually non-replicating or replication-impaired vectors, which means that the viral vector cannot replicate to any significant extent in normal cells (e.g., normal human cells), as measured by conventional means (e.g. via measuring DNA synthesis and/or viral titer). Non-replicating or replication-impaired vectors may have become so naturally (i.e., they have been isolated as such from nature) or artificially (e.g., by breeding in vitro or by genetic manipulation). There will generally be at least one cell-type in which the replication-impaired viral vector can be grown—for example, modified vaccinia Ankara (MVA) can be grown in CEF cells. Typically, viral vectors are incapable of causing a significant infection in a subject, typically in a mammalian subject.

"Retroviruses" are viruses having an RNA genome. In particular embodiments, a retroviral vector contains all of the cis-acting sequences necessary for the packaging and integration of the viral genome, i.e., (a) a long terminal repeat (LTR), or portions thereof, at each end of the vector; (b) primer binding sites for negative and positive strand DNA synthesis; and (c) a packaging signal, necessary for the incorporation of genomic RNA into virions. More detail regarding retroviral vectors can be found in Boesen, et al., 1994, *Biotherapy* 6:291-302; Clowes, et al., 1994, *J. Clin. Invest.* 93:644-651; Kiem, et al., 1994, *Blood* 83:1467-1473; Salmons and Gunzberg, 1993, *Human Gene Therapy* 4:129-141; Miller, et al., 1993, *Meth. Enzymol.* 217:581-599; and Grossman and Wilson, 1993, *Curr. Opin. in Genetics and Devel.* 3:110-114.

"Gammaretroviruses" refers to a genus of the retroviridae family. Exemplary gammaretroviruses include mouse stem cell virus, murine leukemia virus, feline leukemia virus, feline sarcoma virus, and avian reticuloendotheliosis viruses.

Widely used retroviral vectors include those based upon murine leukemia virus (MuLV), gibbon ape leukemia virus (GaLV), simian immunodeficiency virus (SIV), human immunodeficiency virus (HIV), and combinations thereof (see, e.g., Buchscher et al., J. Virol. 66:2731-2739, 1992; Johann et al., J. Virol. 66:1635-1640, 1992; Sommerfelt et al., Virol. 176:58-59, 1990; Wilson et al., J. Virol. 63:2374-2378, 1989; Miller et al., J. Virol. 65:2220-2224, 1991; and PCT/US94/05700).

Particularly suitable are lentiviral vectors. "Lentivirus" refers to a genus of retroviruses that are capable of infecting dividing and non-dividing cells and typically produce high viral titers. Lentiviral vectors have been employed in gene therapy for a number of diseases. For example, hematopoietic gene therapies using lentiviral vectors or gamma retroviral vectors have been used for x-linked adrenoleukodystrophy and beta thalassaemia. See, e.g., Kohn et al., Clin. Immunol. 135:247-54, 2010; Cartier et al., Methods Enzymol. 507:187-198, 2012; and Cavazzana-Calvo et al., Nature 467:318-322, 2010. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

In particular embodiments, other retroviral vectors can be used in the practice of the methods disclosed herein. These include, e.g., vectors based on human foamy virus (HFV) or other viruses in the Spumavirus genera.

Foamy viruses (FVes) are the largest retroviruses known today and are widespread among different mammals, including all non-human primate species, however are absent in humans. This complete apathogenicity qualifies FV vectors as ideal gene transfer vehicles for genetic therapies in humans and clearly distinguishes FV vectors as gene delivery system from HIV-derived and also gammaretrovirus-derived vectors.

FV vectors are suitable for gene therapy applications because they can (1) accommodate large transgenes (>9kb), (2) transduce slowly dividing cells efficiently, and (3) integrate as a provirus into the genome of target cells, thus enabling stable long term expression of the transgene(s). FV vectors do need cell division for the pre-integration complex to enter the nucleus, however the complex is stable for at least 30 days and still infective. The intracellular half-life of the FV pre-integration complex is comparable to the one of lentiviruses and significantly higher than for gammaretroviruses, therefore FV are also—similar to LV vectors—able to transduce rarely dividing cells. FV vectors are natural self-inactivating vectors and characterized by the fact that they seem to have hardly any potential to activate neighboring genes. In addition, FV vectors can enter any cells known (although the receptor is not identified yet) and infectious vector particles can be concentrated 100-fold without loss of infectivity due to a stable envelope protein. FV vectors achieve high transduction efficiency in HSC and have been used in animal models to correct monogenetic diseases such as leukocyte adhesion deficiency (LAD) in dogs and Fanconi anemia in mice. FV vectors are also used in preclinical studies of β-thalassemia.

Additional examples of viral vectors include those derived from adenoviruses (e.g., adenovirus 5 (Ad5), adenovirus 35 (Ad35), adenovirus 11 (Ad11), adenovirus 26 (Ad26), adenovirus 48 (Ad48) or adenovirus 50 (Ad50)), adeno-associated virus (AAV; see, e.g., U.S. Pat. No. 5,604,090; Kay et al., Nat. Genet. 24:257 (2000); Nakai et al., Blood 91:4600 (1998)), alphaviruses, cytomegaloviruses (CMV), flaviviruses, herpes viruses (e.g., herpes simplex), influenza viruses, papilloma viruses (e.g., human and bovine papilloma virus; see, e.g., U.S. Pat. No. 5,719,054), poxviruses, vaccinia viruses, etc. See Kozarsky and Wilson, 1993, Current Opinion in Genetics and Development 3:499-503, Rosenfeld, et al., 1991, Science 252:431-434; Rosenfeld, et al., 1992, Cell 68:143-155; Mastrangeli, et al., 1993, J. Clin. Invest. 91:225-234; Walsh, et al., 1993, Proc. Soc. Exp. Bioi. Med. 204:289-300; and Lundstrom, 1999, J. Recept. Signal Transduct. Res. 19: 673-686. Examples include modified vaccinia Ankara (MVA) and NYVAC, or strains derived therefrom. Other examples include avipox vectors, such as a fowlpox vectors (e.g., FP9) or canarypox vectors (e.g., ALVAC and strains derived therefrom).

Other methods of gene delivery include use of artificial chromosome vectors such as mammalian artificial chromosomes (Vos, 1998, Curr. Op. Genet. Dev. 8:351-359) and yeast artificial chromosomes (YAC). YAC are typically used when the inserted nucleic acids are too large for more conventional vectors (e.g., greater than 12 kb).

Vectors and other methods to deliver nucleic acids can include regulatory sequences to control the expression of the nucleic acid molecules. These regulatory sequences can be eukaryotic or prokaryotic in nature. In particular embodiments, the regulatory sequence can be a tissue specific promoter such that the expression of the one or more therapeutic proteins will be substantially greater in the target tissue type compared to other types of tissue. In particular embodiments, the regulatory sequence can result in the constitutive expression of the one or more therapeutic proteins or CAR upon entry of the vector into the cell. Alternatively, the regulatory sequences can include inducible sequences. Inducible regulatory sequences are well known to those skilled in the art and are those sequences that require the presence of an additional inducing factor to result in expression of the one or more therapeutic proteins or CAR. Examples of suitable regulatory sequences include binding sites corresponding to tissue-specific transcription factors based on endogenous nuclear proteins, sequences that direct expression in a specific cell type, the lac operator, the tetracycline operator and the steroid hormone operator. Any inducible regulatory sequence known to those of skill in the art may be used.

In particular embodiments, the nucleic acid is stably integrated into the genome of a cell. In particular embodiments, the nucleic acid is stably maintained in a cell as a separate, episomal segment.

In particular embodiments, the efficiency of integration, the size of the DNA sequence that can be integrated, and the number of copies of a DNA sequence that can be integrated into a genome can be improved by using transposons. Transposons or transposable elements include a short nucleic acid sequence with terminal repeat sequences upstream and downstream. Active transposons can encode enzymes that facilitate the excision and insertion of nucleic acid into a target DNA sequence.

A number of transposable elements have been described in the art that facilitate insertion of nucleic acids into the genome of vertebrates, including humans. Examples include sleeping beauty (e.g., derived from the genome of salmonid fish); piggyback (e.g., derived from lepidopteran cells and/or the *Myotis lucifugus*); mariner (e.g., derived from *Drosophila*); frog prince (e.g., derived from *Rana pipiens*); Tol2 (e.g., derived from medaka fish); TcBuster (e.g., derived from the red flour beetle *Tribolium castaneum*) and spinON. CRISPR-Cas systems may also be used.

Gene editing technologies such as CRISPR-Cas; CRISPR-Cpf1; megaTALs, TALENs, or zinc finger nucleases may also be used. For addition of gene sequences, approaches that facilitate homology-directed repair (HDR) should be adopted (e.g., homology arms).

Any nucleic acid including a therapeutic gene or CAR can be introduced into cells disclosed herein. The term "gene" refers to a nucleic acid sequence (used interchangeably with polynucleotide or nucleotide sequence) that encodes one or more therapeutic proteins or CAR as described herein. This definition includes various sequence polymorphisms, mutations, and/or sequence variants wherein such alterations do not substantially affect the function of the encoded one or more therapeutic proteins or CAR. The term "gene" may include not only coding sequences but also regulatory regions such as promoters, enhancers, and termination regions. The term further can include all introns and other DNA sequences spliced from the mRNA transcript, along with variants resulting from alternative splice sites. Gene sequences encoding the molecule can be DNA or RNA that directs the expression of the one or more therapeutic proteins or CAR. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific cell type.

A gene sequence encoding one or more therapeutic proteins or CAR can be readily prepared by synthetic or recombinant methods from the relevant amino acid sequence. In particular embodiments, the gene sequence encoding any of these sequences can also have one or more restriction enzyme sites at the 5' and/or 3' ends of the coding sequence in order to provide for easy excision and replacement of the gene sequence encoding the sequence with another gene sequence encoding a different sequence. In particular embodiments, the gene sequence encoding the sequences can be codon optimized for expression in mammalian cells.

As one example, a gene can be selected to provide a therapeutically effective response against a condition that, in particular embodiments, is inherited. In particular embodiments, the condition can be Grave's Disease, rheumatoid arthritis, pernicious anemia, Multiple Sclerosis (MS), inflammatory bowel disease, systemic lupus erythematosus (SLE), adenosine deaminase deficiency (ADA-SCID) or severe combined immunodeficiency disease (SCID), Wiskott-Aldrich syndrome (WAS), chronic granulomatous disease (CGD), Fanconi anemia (FA), Battens disease, adrenoleukodystrophy (ALD) or metachromatic leukodystrophy (MLD), muscular dystrophy, pulmonary alveolar proteinosis (PAP), pyruvate kinase deficiency, Shwachman Diamond-Blackfan anemia, dyskeratosis congenita, cystic fibrosis, Parkinson's disease, Alzheimer's disease, or amyotrophic lateral sclerosis (Lou Gehrig's disease). In particular embodiments, depending on the condition, the therapeutic gene may be a gene that encodes a protein and/or a gene whose function has been interrupted. Exemplary therapeutic gene and gene products include: soluble CD40; CTLA; Fas L; antibodies to CD4, CD5, CD7, CD52, etc.; antibodies to IL4; IL2; IL6; an antibody to TCR specifically present on autoreactive T cells; IL4; IL10; IL12; IL13; IL1Ra, sIL1RI, sIL1RII; sTNFRI; sTNFRII; antibodies to TNF; P53, PTPN22, and DRB1*1501/DQB1*0602; globin family genes; WAS; phox; FANC family genes; dystrophin; pyruvate kinase; CLN3; ABCD1; arylsulfatase A; SFTPB; SFTPC; NLX2.1; ABCA3; GATA1; ribosomal protein genes; TERT; TERC; DKC1; TINF2; CFTR; LRRK2; PARK2; PARK7; PINK1; SNCA; PSEN1; PSEN2; APP; SOD1; TDP43; FUS; ubiquilin 2; and/or C9ORF72. Therapeutically effective amounts may provide function to immune and other blood cells and/or microglial cells or may alternatively—depending on the treated condition—inhibit lymphocyte activation, induce apoptosis in lymphocytes, eliminate various subsets of lymphocytes, inhibit T cell activation, eliminate or inhibit autoreactive T cells, inhibit Th-2 or Th-1 lymphocyte activity, antagonize IL1 or TNF, reduce inflammation, induce selective tolerance to an inciting agent, reduce or eliminate an immune-mediated condition; and/or reduce or eliminate a symptom of the immune-mediated condition. Therapeutic effective amounts may also provide functional DNA repair mechanisms; surfactant protein expression; telomere maintenance; lysosomal function; breakdown of lipids or other proteins such as amyloids; permit ribosomal function; and/or permit development of mature blood cell lineages which would otherwise not develop such as macrophages other white blood cell types.

As another example, a gene can be selected to provide a therapeutically effective response against diseases related to red blood cells and clotting. In particular embodiments, the disease is a hemoglobinopathy like thalassemia, or a sickle cell disease/trait. The therapeutic gene may be, for example, a gene that induces or increases production of hemoglobin; induces or increases production of beta-globin, or alpha-globin; or increases the availability of oxygen to cells in the body. The therapeutic gene may be, for example, HBB or CYB5R3. Exemplary effective treatments may, for example, increase blood cell counts, improve blood cell function, or increase oxygenation of cells in patients. In another particular embodiment, the disease is hemophilia. The therapeutic gene may be, for example, a gene that increases the production of coagulation/clotting factor VIII or coagulation/clotting factor IX, causes the production of normal versions of coagulation factor VIII or coagulation factor IX, a gene that reduces the production of antibodies to coagulation/clotting factor VIII or coagulation/clotting factor IX, or a gene that causes the proper formation of blood clots. Exemplary therapeutic genes include F8 and F9. Exemplary effective treatments may, for example, increase or induce the production of coagulation/clotting factors VIII and IX; improve the functioning of coagulation/clotting factors VIII and IX, or reduce clotting time in subjects.

As another example, a gene can be selected to provide a therapeutically effective response against a lysosomal storage disorder. In particular embodiments, the lysosomal storage disorder is mucopolysaccharidosis (MPS), type I; MPS II or Hunter Syndrome; MPS III or Sanfilippo syndrome; MPS IV or Morquio syndrome; MPS V; MPS VI or Maroteaux-Lamy syndrome; MPS VII or sly syndrome; alpha-mannsidosis; beta-mannosidosis; glycogen storage disease type I, also known as GSDI, von Gierke disease, or Tay Sachs; Pompe disease; Gaucher disease; or Fabry disease. The therapeutic gene may be, for example a gene encoding or inducing production of an enzyme, or that otherwise causes the degradation of mucopolysaccharides in lysosomes. Exemplary therapeutic genes include IDUA or iduronidase, IDS, GNS, HGSNAT, SGSH, NAGLU, GUSB, GALNS, GLB1, ARSB, and HYAL1. Exemplary effective genetic therapies for lysosomal storage disorders may, for example, encode or induce the production of enzymes responsible for the degradation of various substances in lysosomes; reduce, eliminate, prevent, or delay the swelling in various organs, including the head (exp. Macrosephaly), the liver, spleen, tongue, or vocal cords; reduce fluid in the brain; reduce heart valve abnormalities; prevent or dilate narrowing airways and prevent related upper respiratory conditions like infections and sleep apnea; reduce, eliminate, prevent, or delay the destruction of neurons, and/or the associated symptoms.

As another example, a gene can be selected to provide a therapeutically effective response against a hyperproliferative disease. In particular embodiments, the hyperproliferative disease is cancer. The therapeutic gene may be, for example, a tumor suppressor gene, a gene that induces apoptosis, a gene encoding an enzyme, a gene encoding an antibody, or a gene encoding a hormone. Exemplary therapeutic genes and gene products include 101F6, 123F2 (RASSF1), 53BP2, abl, ABLI, ADP, aFGF, APC, ApoAI, ApoAIV, ApoE, ATM, BAI-1, BDNF, Beta*(BLU), bFGF, BLC1, BLC6, BRCA1, BRCA2, CBFA1, CBL, C-CAM, CFTR, CNTF, COX-1, CSFIR, CTS-1, cytosine deaminase, DBCCR-1, DCC, Dp, DPC-4, E1A, E2F, EBRB2, erb, ERBA, ERBB, ETS1, ETS2, ETV6, Fab, FCC, FGF, FGR, FHIT, fms, FOX, FUS 1, FUS1, FYN, G-CSF, GDAIF, Gene 21 (NPRL2), Gene 26 (CACNA2D2), GM-CSF, GMF, gsp, HCR, HIC-1, HRAS, hst, IGF, IL-1, IL-2, IL-3, IL-4, IL-5, IL-6, IL-7, IL-8, IL-9, IL-10, IL-11 IL-12, ING1, interferon α, interferon β, interferon γ, IRF-1, JUN, KRAS, LCK, LUCA-1 (HYAL1), LUCA-2 (HYAL2), LYN, MADH4, MADR2, MCC, mda7, MDM2, MEN-I, MEN-II, MLL, MMAC1, MYB, MYC, MYCL1, MYCN, neu, NF-1, NF-2, NGF, NOEY1, NOEY2, NRAS, NT3, NT5, OVCA1, p16, p21, p27, p53, p57, p73, p300, PGS, PIM1, PL6, PML, PTEN, raf, Rap1A, ras, Rb, RB1, RET, rks-3, ScFv, scFV ras, SEM A3, SRC, TAL1, TCL3, TFPI, thrombospondin, thymidine kinase, TNF, TP53, trk, T-VEC, VEGF, VHL, WT1, WT-1, YES, and zac1. Exemplary effective genetic therapies may suppress or eliminate tumors, result in a decreased number of cancer cells, reduced tumor size, slow or eliminate tumor growth, or alleviate symptoms caused by tumors.

As another example, a gene can be selected to provide a therapeutically effective response against an infectious disease. In particular embodiments, the infectious disease is human immunodeficiency virus (HIV). The therapeutic gene may be, for example, a gene rendering immune cells resistant to HIV infection, or which enables immune cells to effectively neutralize the virus via immune reconstruction, polymorphisms of genes encoding proteins expressed by immune cells, genes advantageous for fighting infection that are not expressed in the patient, genes encoding an infectious agent, receptor or coreceptor; a gene encoding ligands for receptors or coreceptors; viral and cellular genes essential for viral replication including; a gene encoding ribozymes, antisense RNA, small interfering RNA (siRNA) or decoy RNA to block the actions of certain transcription factors; a gene encoding dominant negative viral proteins, intracellular antibodies, intrakines and suicide genes. Exemplary therapeutic genes and gene products include α2β1; αvβ3; αvβ5; αvβ63; BOB/GPR15; Bonzo/STRL-33/TYM-STR; CCR2; CCR3; CCR5; CCR8; CD4; CD46; CD55; CXCR4; aminopeptidase-N; HHV-7; ICAM; ICAM-1; PRR2/HveB; HveA; α-dystroglycan; LDLR/α2MR/LRP; PVR; PRR1/HveC; and laminin receptor. A therapeutically effective amount for the treatment of HIV, for example, may increase the immunity of a subject against HIV, ameliorate a symptom associated with AIDS or HIV, or induce an innate or adaptive immune response in a subject against HIV. An immune response against HIV may include antibody production and result in the prevention of AIDS and/or ameliorate a symptom of AIDS or HIV infection of the subject, or decrease or eliminate HIV infectivity and/or virulence.

As indicated, methods disclosed herein include enriching for/isolating, expanding, ablating and/or modifying cells for treating subjects (humans, veterinary animals (dogs, cats, reptiles, birds, etc.), livestock (horses, cattle, goats, pigs, chickens, etc.). In particular embodiments, human subjects are pediatric. Treating subjects includes delivering therapeutically effective amounts. Therapeutically effective amounts include those that provide effective amounts, prophylactic treatments, and/or therapeutic treatments.

An "effective amount" is the number of cells necessary to result in a desired physiological change in a subject. Effective amounts are often administered for research purposes.

A "prophylactic treatment" includes a treatment administered to a subject who does not display signs or symptoms of a condition to be treated or displays only early signs or symptoms of the condition to be treated such that treatment is administered for the purpose of diminishing, preventing, or decreasing the risk of developing the condition. Thus, a prophylactic treatment functions as a preventative treatment against a condition.

A "therapeutic treatment" includes a treatment administered to a subject who displays symptoms or signs of a condition and is administered to the subject for the purpose of reducing the severity or progression of the condition.

The actual dose amount administered to a particular subject can be determined by a physician, veterinarian, or researcher taking into account parameters such as physical and physiological factors including target; body weight; type of condition; severity of condition; upcoming relevant events, when known; previous or concurrent therapeutic interventions; idiopathy of the subject; and route of administration, for example. In addition, in vitro and in vivo assays can optionally be employed to help identify optimal dosage ranges.

Therapeutically effective amounts to administer can include greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$. In particular embodiments, a minimum dose is $2\times10^6$ cells/kg subject body weight.

In particular embodiments, the methods and compositions disclosed herein ablate pHSC within a subject. In particular embodiments, the methods and compositions disclosed herein ablate pHSC within a subject as part of a non-genotoxic conditioning regimen. In particular embodiments, the non-genotoxic conditioning regimen precedes an HSC transplant in the subject and/or the infusion of genetically-modified cells into the subject. In particular embodiments, the subject is a human pediatric subject receiving the HSC transplant and/or the infusion of genetically-modified cells. In particular embodiments, for engraftment purposes, a composition including HSC is administered to a patient following selective ablation as described elsewhere herein.

In particular embodiments, administration of HSC cause an increase in granulocyte colony stimulating factor (GCSF). In certain aspects, the methods and compositions disclosed herein cause an increase in macrophage colony stimulating factor (MCSF). In particular embodiments, the methods and compositions disclosed herein cause an increase in endogenous myeloid cells.

In particular embodiments, hematopoietic recovery includes recovery of white blood cells. In particular embodiments, hematopoietic recovery includes recovery of lymphocytes. In particular embodiments, hematopoietic recovery includes recovery of myeloid cells.

In particular embodiments, hematopoietic recovery includes improvement in one or more complete blood count measures. In particular embodiments, improvement in blood count measure includes an increase in hemoglobin level, an increase in hematocrit level, an increase in red blood cell number, and combinations thereof. In particular embodiments, hematopoietic recovery includes an increase in bone marrow cellularity.

"Complete blood count (CBC)," also known as full blood count (FBC), full blood exam, or blood panel, is a test panel typically ordered by medical professionals that provides information about the cell types and numbers in a patient's blood. In particular embodiments, a "complete blood count measure" includes measurement of total white cells, total red cells, hemoglobin, hematocrit, mean corpuscular volume, mean corpuscular hemoglobin, mean corpuscular hemoglobin concentration, red blood cell distribution width, neutrophil granulocytes, lymphocytes, monocytes, eosinophil granulocytes, basophil granulocytes, platelet numbers, and/or mean platelet volume.

The methods of the disclosure are also useful in the induction of tolerance in a patient, for example tolerance to donor tissue, e.g. in organ transplants; tolerance to autoantigens, e.g. in the context of treatment of autoimmune disease; and the like. In particular embodiments, a method is provided for inducing tolerance in a patient, including administering to a patient a therapeutically effective amount of an agent, for example an antibody coupled to a toxin (or CAR-modified immune cell), that selectively ablates endogenous HSC; and administering to the patient a therapeutically effective amount of HSC from a donor, which administering may be performed in conjunction with introducing an allograft into said patient, treating autoimmune disease, etc.

In particular embodiments, methods and compositions disclosed herein are used to ablate pHSC within a subject to treat a malignancy associated with hyperproliferative HSC, such as a hematopoietic cancer.

Examples of hematopoietic cancers include acute lymphocytic leukemia, B-cell prolymphocytic leukemia, Burkitt lymphoma/leukemia, chronic lymphocytic leukemia (CLL), diffuse large B-cell lymphoma, follicular lymphoma (grades I, II, III, or IV), Hodgkin's lymphoma, intravascular large B-cell lymphoma, lymphoma, lymphoplasmocytic lymphoma, mantle cell lymphoma, marginal zone lymphoma (extra-nodal and nodal), mediastinal (thymic) large B-cell lymphoma, multiple myeloma, non-Hodgkin's lymphoma, POEMS syndrome/osteosclerotic myeloma, primary effusion lymphoma, splenic marginal zone lymphoma, small lymphocytic lymphoma, smoldering multiple myeloma (SMM), and Waldenstrom's macroglobulinemia.

Effective treatments against a malignancy associated with hyperproliferative HSC can be evidenced by an anti-cancer effect. An anti-cancer effect can include one or more of a decrease in the number of cancer cells, an increase in life expectancy, induction of apoptosis of cancer cells, induction of cancer cell death, inhibition of cancer cell proliferation, prolongation of a subject's life, and/or reduction of relapse or re-occurrence of the cancer following treatment.

As indicated, the compositions and formulations disclosed herein can be administered by, for example, injection, infusion, perfusion, or lavage and can more particularly include administration through one or more bone marrow, intravenous, intradermal, intraarterial, intranodal, intralymphatic, intraperitoneal, intralesional, intraprostatic, intravaginal, intrarectal, topical, intrathecal, intratumoral, intramuscular, intravesicular, and/or subcutaneous infusions and/or bolus injections.

In particular embodiments, purification and final formulation of cells includes pelleting the cell product and removing the resulting supernatant. Exemplary cellular carriers include saline, buffered saline, physiological saline, water, Hanks' solution, Ringer's solution, Nonnosol-R (Abbott Labs), Plasma-Lyte A® (Baxter Laboratories, Inc., Morton Grove, Ill.), glycerol, ethanol, and combinations thereof.

In particular embodiments, carriers can be supplemented with human serum albumin (HSA) or other human serum components or fetal bovine serum. In particular embodiments, a carrier for infusion includes buffered saline with 5% HAS or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, formulations can include a local anesthetic such as lidocaine to ease pain at a site of injection.

Therapeutically effective amounts of cells within formulations can be greater than $10^2$ cells, greater than $10^3$ cells, greater than $10^4$ cells, greater than $10^6$ cells, greater than $10^6$ cells, greater than $10^7$ cells, greater than $10^8$ cells, greater than $10^9$ cells, greater than $10^{10}$ cells, or greater than $10^{11}$.

In formulations disclosed herein, cells are generally in a volume of a liter or less, 500 mls or less, 250 mls or less or 100 mls or less. Hence the density of administered cells is typically greater than $10^4$ cells/ml, $10^7$ cells/ml or $10^8$ cells/ml.

The formulations disclosed herein can be prepared for administration by, for example, injection, infusion, perfusion, or lavage.

EXEMPLARY EMBODIMENTS

1. A method of preparing an enriched primitive hematopoietic stem cell (pHSC) population including: obtaining a stem cell source;
enriching the stem cell source for LH R+/CD34+ cells; LH R+/CD34+/CD38− cells; LHR+/CD34+/CD45RA− cells; LHR+/CD34+/CD90+ cells; LHR+/CD34+/CD90− cells; LHR+/CD34+/CD38−/CD45RA−/CD90+ cells or LHR+/CD34+/CD38−/CD45RA−/CD90− cells thereby preparing the enriched pHSC population.
2. A method of embodiment 2, wherein the enriching does not utilize CD49f.
3. A method of embodiment 1 or 2, wherein the stem cell source includes umbilical cord blood, placental blood, bone marrow, or peripheral blood.
4. A method of any of embodiments 1-3, wherein the enriching includes magnetic-assisted cell sorting (MACS), fluorescence-activated cell sorting (FACS) or antibody-panning.
5. A method of any of embodiments 1-4, wherein the enriching utilizes a luteinizing hormone receptor (LHR) binding agent.
6. A method of embodiment 5, wherein the LHR binding agent includes a luteinizing hormone (LH) alpha subunit and a LH beta subunit.
7. A method of embodiment 6, wherein the LH alpha subunit and LH beta subunit include SEQ ID NO: 23 and SEQ ID NO: 22 or SEQ ID NO: 11 and SEQ ID NO: 9.
8. A method of any of embodiments 5-7, wherein the LHR binding agent includes SEQ ID NO: 51.
9. A method of any of embodiments 5-8, wherein the LHR binding agent includes:
a CDRH1 of SEQ ID NO: 28, a CDRH2 of SEQ ID NO: 29, a CDRH3 of SEQ ID NO: 30, a CDRL1 of SEQ ID NO: 31, a CDRL2 of DTS, and a CDRL3 of SEQ ID NO: 32;
a CDRH1 of SEQ ID NO: 33, a CDRH2 of SEQ ID NO: 34, a CDRH3 of SEQ ID NO: 35, a CDRL1 of SEQ ID NO: 36, a CDRL2 of WAS, and a CDRL3 of SEQ ID NO: 37;
a CDRH1 of SEQ ID NO: 38, a CDRH2 of SEQ ID NO: 39, a CDRH3 of SEQ ID NO: 40, a CDRL1 of SEQ ID NO: 41, a CDRL2 of NAS, and a CDRL3 of SEQ ID NO: 42;
a heavy chain of SEQ ID NO: 43 and a light chain of SEQ ID NO: 44;
a heavy chain of SEQ ID NO: 45 and a light chain of SEQ ID NO: 46;
a heavy chain of SEQ ID NO: 47 and a light chain of SEQ ID NO: 48; or
a heavy chain of SEQ ID NO: 49 and a light chain of SEQ ID NO: 50.
10. A method of any of embodiments 1-9, further including culturing the enriched pHSC population in culture media supplemented with an LH agonist. Exemplary embodiment 10 also includes a method of expanding pHSC populations in culture media supplemented with an LH agonist that is practiced independently of embodiments 1-9.
11. A method of embodiment 10, wherein the LH agonist includes an LH alpha subunit and an LH beta subunit.
12. A method of embodiment 11, wherein the LH alpha subunit and LH beta subunit include SEQ ID NO: 23 and SEQ ID NO: 22 or SEQ ID NO: 11 and SEQ ID NO: 9.
13. A method of any of embodiments 10-12, wherein the LH agonist includes SEQ ID NO: 51.
14. A method of any of embodiments 10-13, wherein the culture media is further supplemented with either human stem cell factor (SCF), human thrombopoietin (TPO), and human Fms-related tyrosine kinase 3 ligand (FLT-3L) or SCF and human interleukin-3 (IL-3).
15. A method of embodiment 15, wherein the SCF, TPO and FLT-3L or the SCF and IL-3 are recombinant SCF, TPO and FLT-3L or recombinant SCF and IL-3.
16. A method of any of embodiments 1-15, further including genetically modifying the enriched pHSC population.
17. A method of embodiment 16, wherein the genetic modification results in expression of a therapeutic gene.
18. A method of embodiment 17, wherein the therapeutic gene is selected from ABCD1, ABCA3, ABLI, ADA, AKT1, APC, APP, ARSA, ARSB, BCL11A, BLC1, BLC6, BRCA1, BRCA2, BRIP1, C9ORF72, C46 or other C peptide, CAR, CAS9, C-CAM, CBFAI, CBL, CCR5, CD4, CD19, CD40, CDA, CFTR, CLN3, C-MYC, CRE, CSCR4, CSFIR, CTLA, CTS-I, CYB5R3, DCC, DHFR, DKC1, DLL1, DMD, EGFR, ERBA, ERBB, EBRB2, ETSI, ETS2, ETV6, F8, F9, FANCA, FANCB, FANCC, FANCD2, FANCE, FANCF, FANCG, FANCI, FANCL, FANCM, FasL, FCC, FGR, FOX, FUS, FUSI, FYN, GALNS, GATA1, GLB1, GNS, GUSB, HBB, HBD, HBE1, HBG1, HBG2, HCR, HGSNAT, HOXB4, HRAS, HYAL1, ICAM-1, iCaspase, IDUA, IDS, JUN, KLF4, KRAS, LCK, LRRK2, LYN, MCC, MDM2, MGMT, MLL, MMACI, MYB, MEN-I, MEN-II, MYC, NAGLU, NANOG, NF-1, NF-2, NKX2.1, NOTCH, OCT4, p16, p21, p27, p53, p57, p73, PALB2, PARK2, PARK7, phox, PINK1, PK, PSEN1, PSEN2, PTPN22, RAD51C, ras, RPL3 through RPL40, RPLP0, RPLP1, RPLP2, RPS2 through RPS30, RPSA, SFTPB, SFTPC, SGSH, SLX4, SNCA, SOD1, SOX2, TERC, TERT, TDP43, TINF2, TK, ubiquilin 2, VHL, WAS or WT-1.
19. A method of any of embodiments 16-18, wherein the genetic modification includes a non-integrating vector.
20. A method of any of embodiments 16-19, wherein the genetic modification includes a viral vector.
21. A method of embodiment 20, wherein the viral vector is a lentiviral vector or a foamy viral vector.
22. A method of any of embodiments 1-21, further including formulating the enriched pHSC population for administration to a subject.
23. A method of ablating primitive hematopoietic stem cells (pHSC) in a subject in need thereof including administering to the subject a therapeutically effective amount of a pHSC-ablating agent including a luteinizing hormone receptor (LHR) binding agent.
24. A method of embodiment 23, wherein the LHR binding agent includes a luteinizing hormone (LH) alpha subunit and a LH beta subunit.
25. A method of embodiment 24, wherein the LH alpha subunit and LH beta subunit include SEQ ID NO: 23 and SEQ ID NO: 22 or SEQ ID NO: 11 and SEQ ID NO: 9.
26. A method of any of embodiments 23-25, wherein the LHR binding agent includes SEQ ID NO: 51.
27. A method of any of embodiments 23-26, wherein the LHR binding agent includes:
a CDRH1 of SEQ ID NO: 28, a CDRH2 of SEQ ID NO: 29, a CDRH3 of SEQ ID NO: 30, a CDRL1 of SEQ ID NO: 31, a CDRL2 of DTS, and a CDRL3 of SEQ ID NO: 32;
a CDRH1 of SEQ ID NO: 33, a CDRH2 of SEQ ID NO: 34, a CDRH3 of SEQ ID NO: 35, a CDRL1 of SEQ ID NO: 36, a CDRL2 of WAS, and a CDRL3 of SEQ ID NO: 37;
a CDRH1 of SEQ ID NO: 38, a CDRH2 of SEQ ID NO: 39, a CDRH3 of SEQ ID NO: 40, a CDRL1 of SEQ ID NO: 41, a CDRL2 of NAS, and a CDRL3 of SEQ ID NO: 42;
a heavy chain of SEQ ID NO: 43 and a light chain of SEQ ID NO: 44;

a heavy chain of SEQ ID NO: 45 and a light chain of SEQ ID NO: 46;
a heavy chain of SEQ ID NO: 47 and a light chain of SEQ ID NO: 48; or
a heavy chain of SEQ ID NO: 49 and a light chain of SEQ ID NO: 50.

28. A method of any of embodiments 23-27, wherein the pHSC-ablating agent includes a lymphocyte genetically-modified to express the LHR binding agent as part of a chimeric antigen receptor (CAR).

29. A method of embodiment 28, wherein the CAR includes 4-1BB and CD3 zeta.

30. A method of embodiment 28 or 29, wherein the CAR includes a CD28 hinge and a CD28 transmembrane domain.

31. A method of any of embodiments 28-30, wherein the CAR includes CD3 zeta and Thy1.1.

32. A method of any of embodiments 28-31, wherein the CAR includes a CD8 hinge and a CD8 transmembrane domain.

33. A method of embodiment 28, wherein the CAR includes SEQ ID NO: 20 or SEQ ID NO: 7.

34. A method of any of embodiments 28-33, wherein the lymphocyte is a T cell or a natural killer (NK) cell.

35. A method of any of embodiments 23-34, wherein the pHSC-ablating agent includes a toxin.

36. A method of embodiment 35, wherein the toxin is selected from abrin A chain, α-amanitin, β-amanitin, γ-amanitin, £-amanitin, amanin, amaninamide, amanullin, amanullinic acid, auristatin-E, crotin, curcin, diphtheria A chain, diphtheria toxin, enomycin, exotoxin A chain, gelonin toxin, luffin toxin, modeccin toxin, momordin toxin, phenomycin, pseudomonas exotoxin A, Ricin A chain, saporin, or trichosanthin toxin.

37. A method of ablating malignant cells in a subject in need thereof including administering to the subject a therapeutically effective amount of genetically-modified lymphocytes expressing a chimeric antigen receptor (CAR) including an extracellular domain including a luteinizing hormone (LH) alpha subunit and a LH beta subunit.

38. A method of embodiment 37, wherein the malignant cells are hematopoietic stem cells.

39. A method of embodiment 37 or 38, wherein the malignant cells are leukemia cells and/or lymphoma cells.

40. A method of any of embodiments 37-39, wherein the LH alpha subunit and LH beta subunit include SEQ ID NO: 23 and SEQ ID NO: 22 or SEQ ID NO: 11 and SEQ ID NO: 9.

41. A method of any of embodiments 37-40, wherein the CAR includes 4-1BB and CD3 zeta.

42. A method of any of embodiments 37-41, wherein the CAR includes a CD28 hinge and a CD28 transmembrane domain.

43. A method of any of embodiments 37-42, wherein the CAR includes CD3 zeta and Thy1.1.

44. A method of any of embodiments 37-43, wherein the CAR includes a CD8 hinge and a CD8 transmembrane domain.

45. A method of embodiment 37, wherein the CAR includes SEQ ID NO: 20 or SEQ ID NO: 7.

46. A method of any of embodiments 37-45, wherein the lymphocyte is a T cell or a natural killer (NK) cell.

47. A chimeric antigen receptor (CAR) including an extracellular domain including a luteinizing hormone (LH) alpha subunit and a LH beta subunit.

48. A CAR of embodiment 47, wherein the LH alpha subunit and LH beta subunit include SEQ ID NO: 23 and SEQ ID NO: 22 or SEQ ID NO: 11 and SEQ ID NO: 9.

49. A CAR of embodiment 48, wherein SEQ ID NO: 23 and SEQ ID NO: 22 are linked by SEQ ID NO: 10 or SEQ ID NO: 11 and SEQ ID NO: 9 are linked by SEQ ID NO: 10.

50. A CAR of any of embodiments 47-49, further including SEQ ID NO: 24 and SEQ ID NO: 25.

51. A CAR of any of embodiments 47-50, further including SEQ ID NO: 26 and SEQ ID NO: 27.

52. A CAR of any of embodiments 47-51, further including SEQ ID NO: 15 and SEQ ID NO: 16.

53. A CAR of any of embodiments 47-52, further including SEQ ID NO: 15, SEQ ID NO: 16 and SEQ ID NO: 17.

54. A CAR of any of embodiments 47, 48, or 50-53, further including a linker that is 16 amino acids or less.

55. A CAR of any of embodiments 47-54, wherein the linker is a Gly-Ser linker.

56. A CAR of embodiment 55, wherein the Gly-Ser linker includes SEQ ID NO: 10.

57. A CAR of any of embodiments 47-56, further including a tag sequence.

58. A CAR of embodiment 57, wherein the tag sequence is selected from Myc tag, Strep tag, His tag, Flag tag, Xpress tag, Avi tag, Calmodulin tag, Polyglutamate tag, HA tag, or V5 tag.

59. A CAR including SEQ ID NO: 20 or SEQ ID NO: 7.

60. cDNA including SEQ ID NO: 19 or SEQ ID NO: 6.

61. A lymphocyte expressing SEQ ID NO: 20 or SEQ ID NO: 7.

62. A lymphocyte including SEQ ID NO: 19 or SEQ ID NO: 6.

63. A lymphocyte of embodiment 61 or 62 wherein the lymphocyte is a T cell or NK cell.

64. A formulation for administration to a subject including an enriched pHSC population formed according to a method of embodiments 1-22, a CAR of embodiments 47-59, cDNA of embodiment 60, and/or a lymphocyte of embodiment 63.

As indicated previously, particular embodiments disclosed herein include variants of protein and/or nucleic acid sequences disclosed herein. Variants of proteins can include those having one or more conservative amino acid substitutions. As used herein, a "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W. H. Freeman and Company.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including (but not limited to) those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

EXAMPLE 1

Suppression of luteinizing hormone enhances HSC recovery after hematopoietic injuries, introduction, There is a significant unmet clinical need for novel strategies to protect the hematopoietic stem cell (HSC) pool and regenerate hematopoiesis after radiation injury caused by common cancer therapies or by accidental exposure[1,2]. In addition to their role in promoting sexual dimorphisms, there is increasing evidence that sex hormones regulate HSC self-renewal, differentiation, and proliferation[3-5]. It has been previously reported that sex steroid ablation (SSA) promoted bone marrow (BM) lymphopoiesis and HSC recovery in aged and immunodepleted mice[5-8]. Here it is shown that the use of a novel luteinizing hormone-releasing hormone-antagonist (LHRH-Ant), currently used widely in the clinic for androgen ablative therapies, promoted hematopoietic recovery and mouse survival when administered 24 h after an otherwise lethal dose of total body irradiation (L-TBI). Unexpectedly, this protective effect was independent of sex steroid inhibition, but relied on the suppression of luteinizing hormone (LH). Long-term self-renewing HSCs (LT-HSCs) derived from both human and mouse expressed high levels of the luteinizing hormone/choriogonadotropin receptor (LHR) and while LH stimulation promoted HSC expansion, its suppression after L-TBI inhibited entry of HSCs into cell cycle, thus promoting HSC quiescence and protection against exhaustion. Taken together these data not only reveal a novel mechanism that regulates HSC function, but also offer a therapeutic approach to promote hematopoietic regeneration after injury.

Background. Radiation-induced BM toxicity is a common dose-limiting side-effect for most cancer therapy and is the primary cause of death for victims of accidental exposure. Despite intensive research to identify effective treatments for hematopoietic recovery and mitigation of radiation injury, available non-cellular approaches are still limited[9]. Although several cytokines and growth factors have shown radio-protective properties when administered before radiation exposure, few are effective in mitigating radiation toxicity in a post-injury setting, restricting their application in the worst-case scenario of a nuclear accident or terrorist attack[19-13].

Figure 1B:
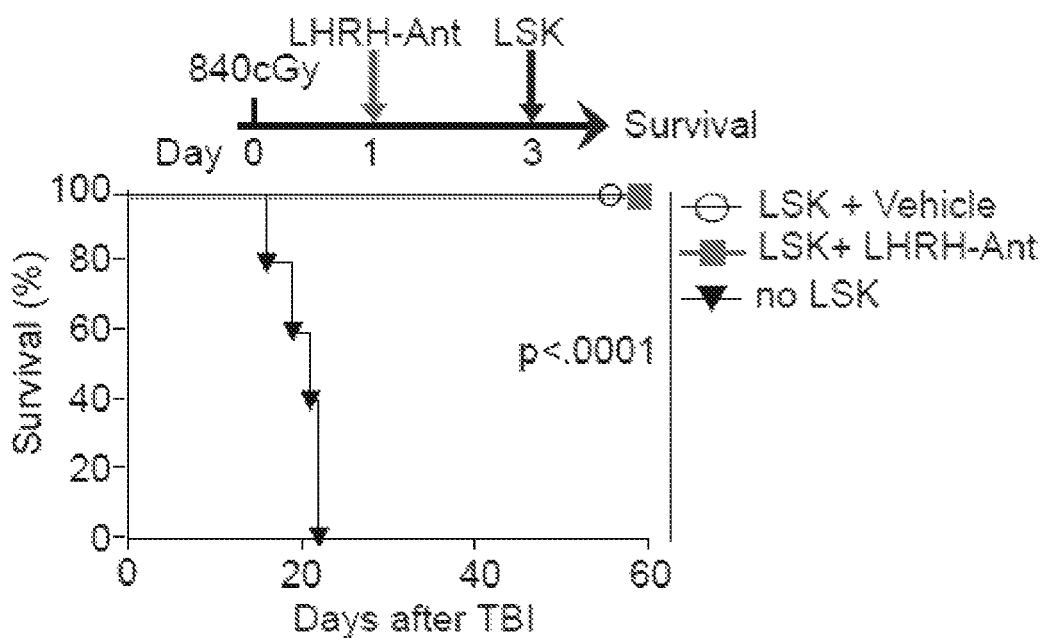
Figure 1C:
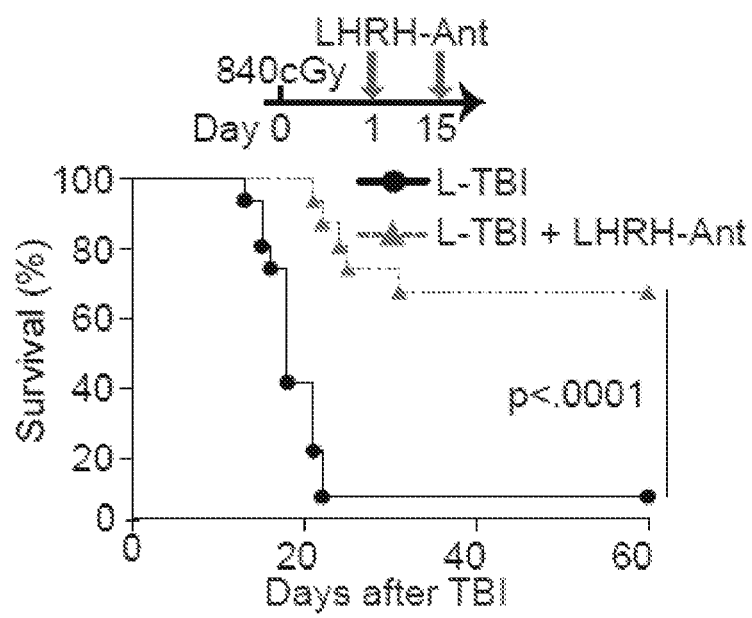
Figure 1D:
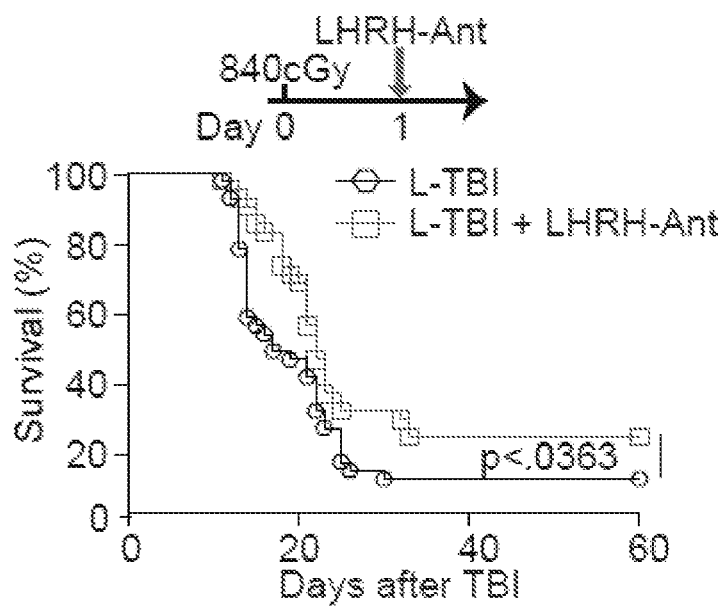
Figure 2A:
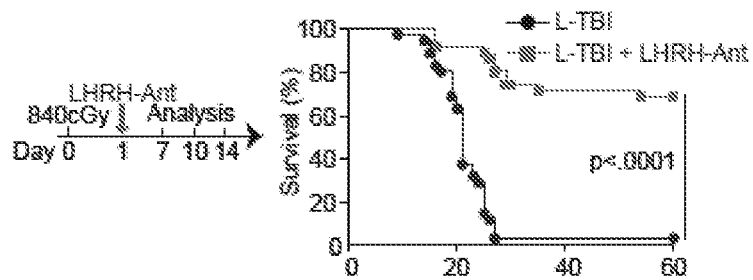
FIGS. 2A-2I. (2A) Mice receiving LHRH-Ant 24 h after L-TBI exposure showed a significant increase in survival compared to control animals treated with vehicle alone. (2B) Complete blood counts analysis revealed that only mice treated with LHRH-Ant recovered after L-TBI. (2C) Treatment with LHRH-Ant significantly enhanced mouse survival even when administered 48 h after L-TBI. (2D) In keeping with the peripheral blood (PB) recovery shown in FIG. 2B), BM cellularity of mice treated with the LHRH-Ant started to separate significantly from the vehicle group by day 14 after radiation. (2E) While there was no difference in total BM cellularity at day 7, there was a significant increase in CFU-GM and BFU-E colonies in L-TBI mice also treated with LHRH-Ant. (2F, 2G) On day 14 after L-TBI, expansion of LSKs as well as their downstream progenitors in mice given LHRH-Ant were found. Moreover, crucially for sustained hematopoiesis, significantly more LT-HSCs were also found. (2H, 2I) Host mice receiving cells from LHRH-Ant-treated L-TBI mice had significantly better hematopoietic reconstitution than recipients of cells from vehicle-treated control L-TBI mice.
Figure 2B:
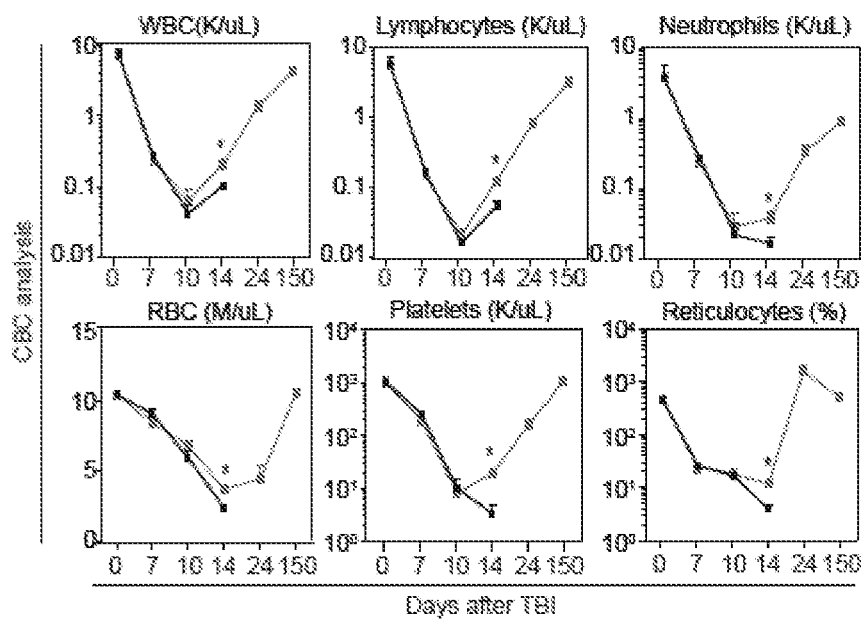
Figure 2C:
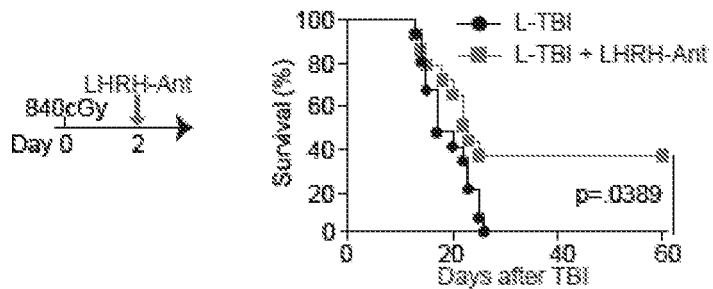
Figure 10A:
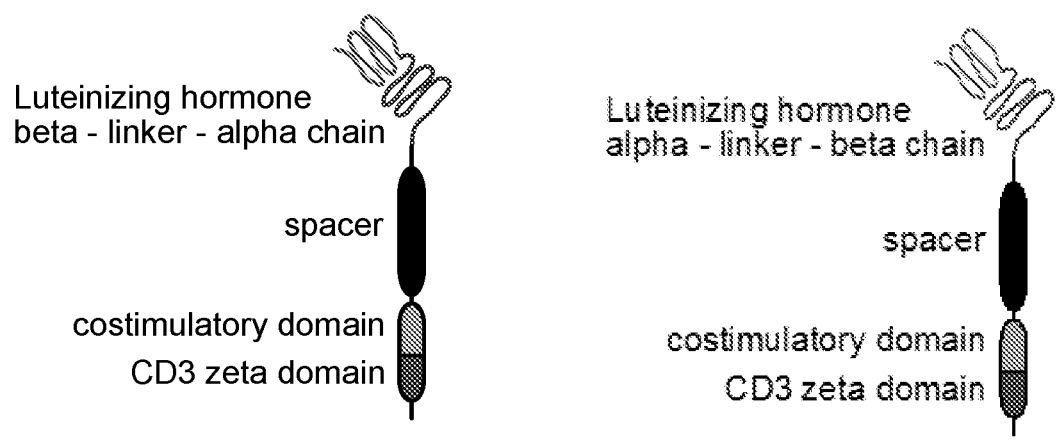
Figure 10B:
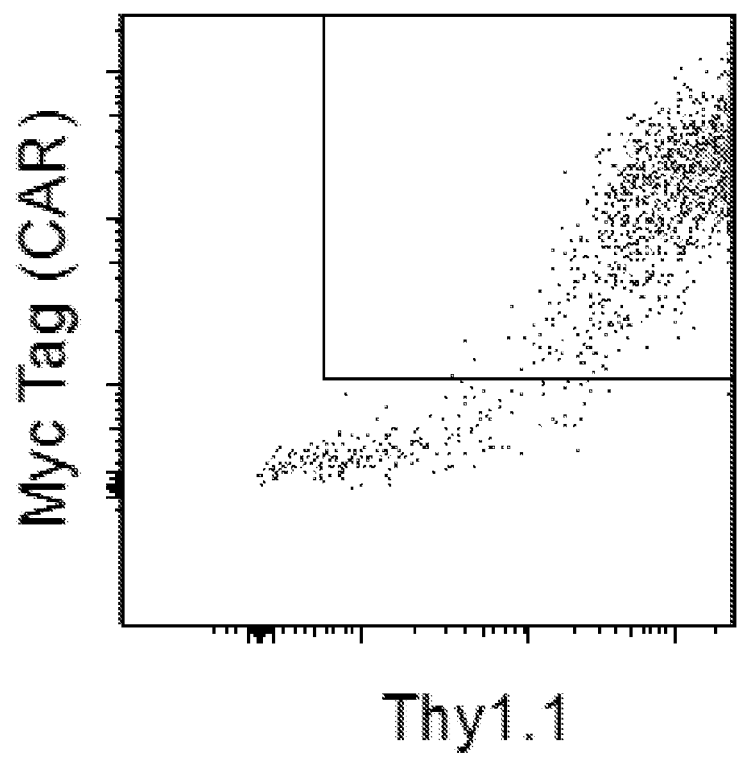
Figure 10D:
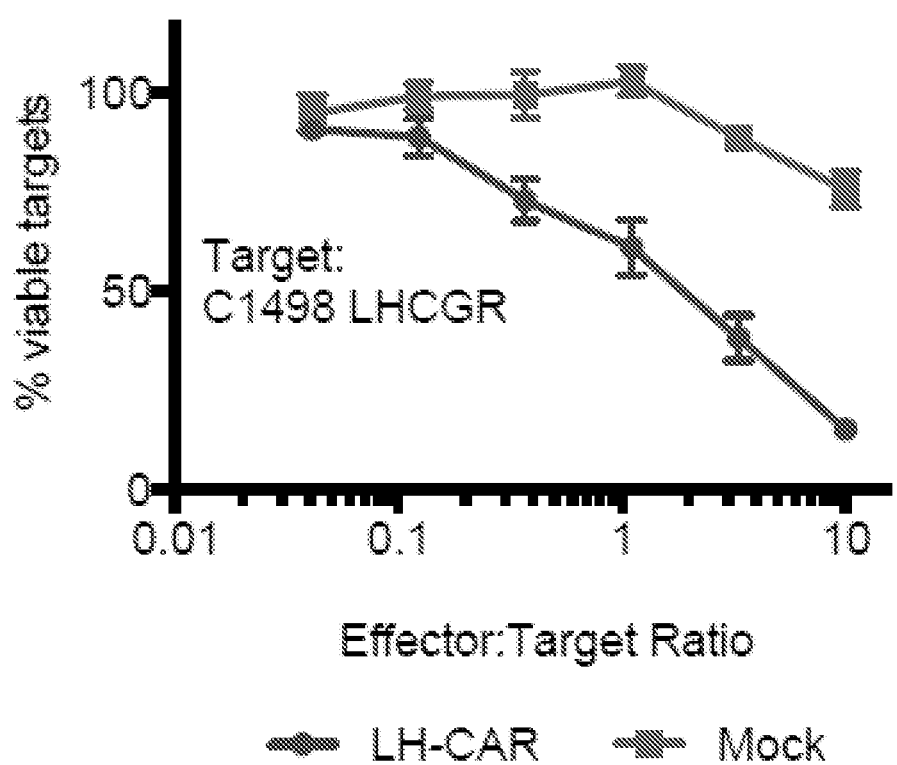

Description. Inhibition of sex steroids, which can be achieved in a reversible fashion pharmacologically, is a well-described strategy to promote lymphopoiesis in the BM and thymus[6,7,14,15]. Although the most common method of sex steroid ablation clinically has been to use LHRH-agonists, it was described that an LHRH-Antagonist represents a more rational approach to promote immediate ablation of sex steroids for immune regeneration as it is far more rapid and abrogates the initial surge in sex steroids that LHRH-Agonist cause[16]. Taken together with the impact of sex steroid inhibition on HSC function and the rapid regenerative effects of LHRH-Ant, it was hypothesized that LHRH-Ant could represent a rational non-cellular medical countermeasure for mitigating radiation injury and promoting hematopoietic regeneration when administered after hematopoietic insult. To test this hypothesis, a lethal TBI (L-TBI) dose of 840 cGy that mediated lethality in more than 90% of mice (FIG. 1A) was used. It was found that mice receiving LHRH-Ant 24 h after L-TBI exposure showed a significant increase in survival compared to control animals treated with vehicle alone (FIG. 2A). Mouse lethality was a result of bone marrow failure, since transplant of BM Lin$^-$Sca1$^+$ckit$^+$ (LSK) cells 3 days after L-TBI completely rescued all mice (FIG. 1B). Despite similar drops in cellularity across both groups for the first 10 days, consistent with the survival data, complete blood counts analysis revealed that only mice treated with LHRH-Ant recovered after L-TBI (FIG. 2B). It was then tested if LHRH-Ant could mediate even greater mouse survival when administered multiple times. However, treatment of the mice 24 h and 15 days after LTBI did not significantly enhance the survival benefit (FIG. 10). Although reduced in its effectiveness, intriguingly, treatment with LHRH-Ant significantly enhanced mouse survival even when administered 48 h after L-TBI, further validating this treatment as a potential countermeasure for radiation exposure (FIG. 2B). Importantly, although modest in comparison to the survival benefit observed in male mice, a statistically significant benefit in survival in female mice given LHRH-Ant was also found (FIG. 1D). This data are in agreement with a previous report, showing that LHRH-Ant has reduced regenerative properties in female mice[16].

Figure 2D:
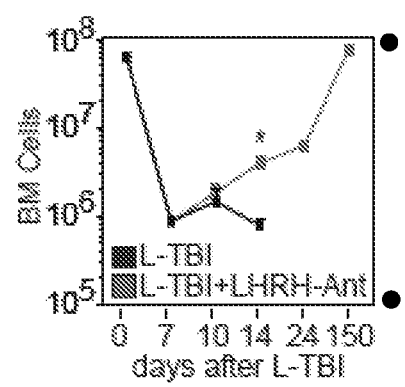
Figure 2E:
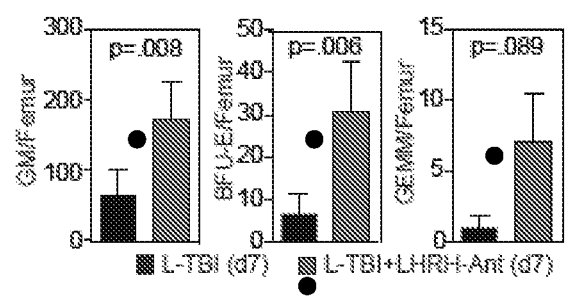
Figure 2F:
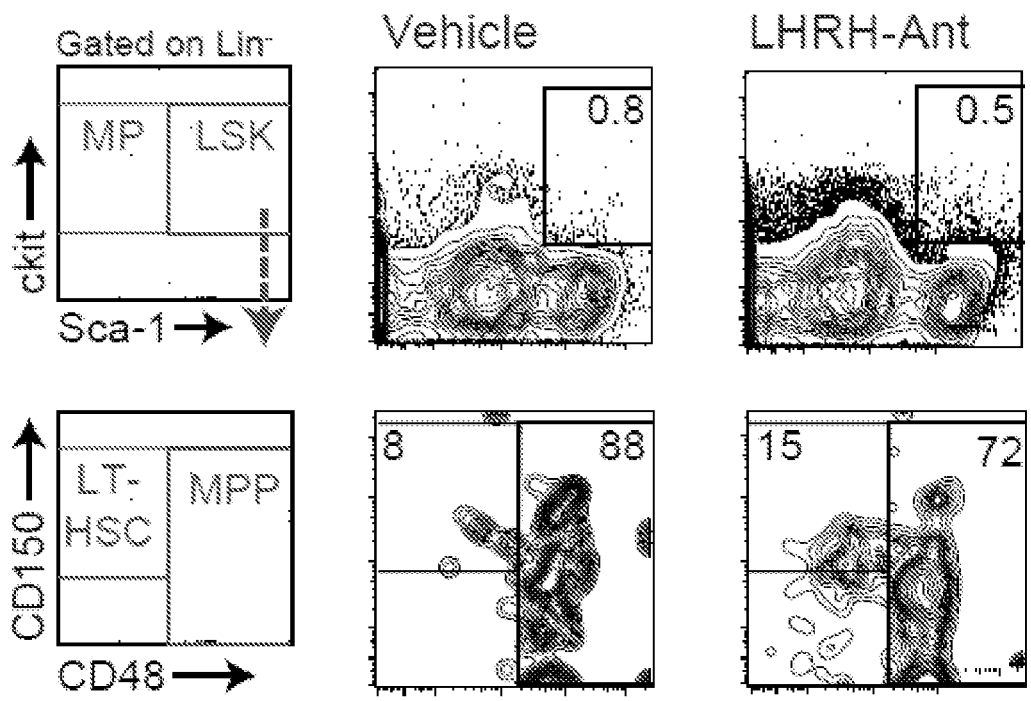
Figure 2G:
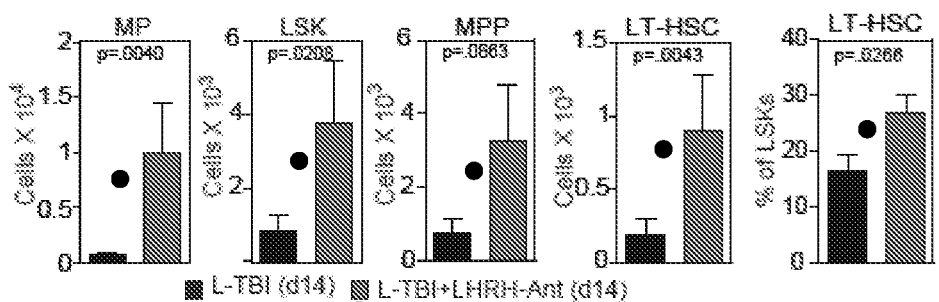
Figure 2H:
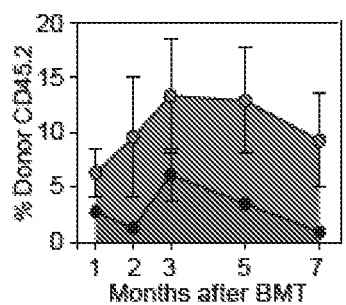
Figure 2I:
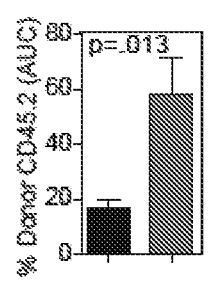
Figure 3:
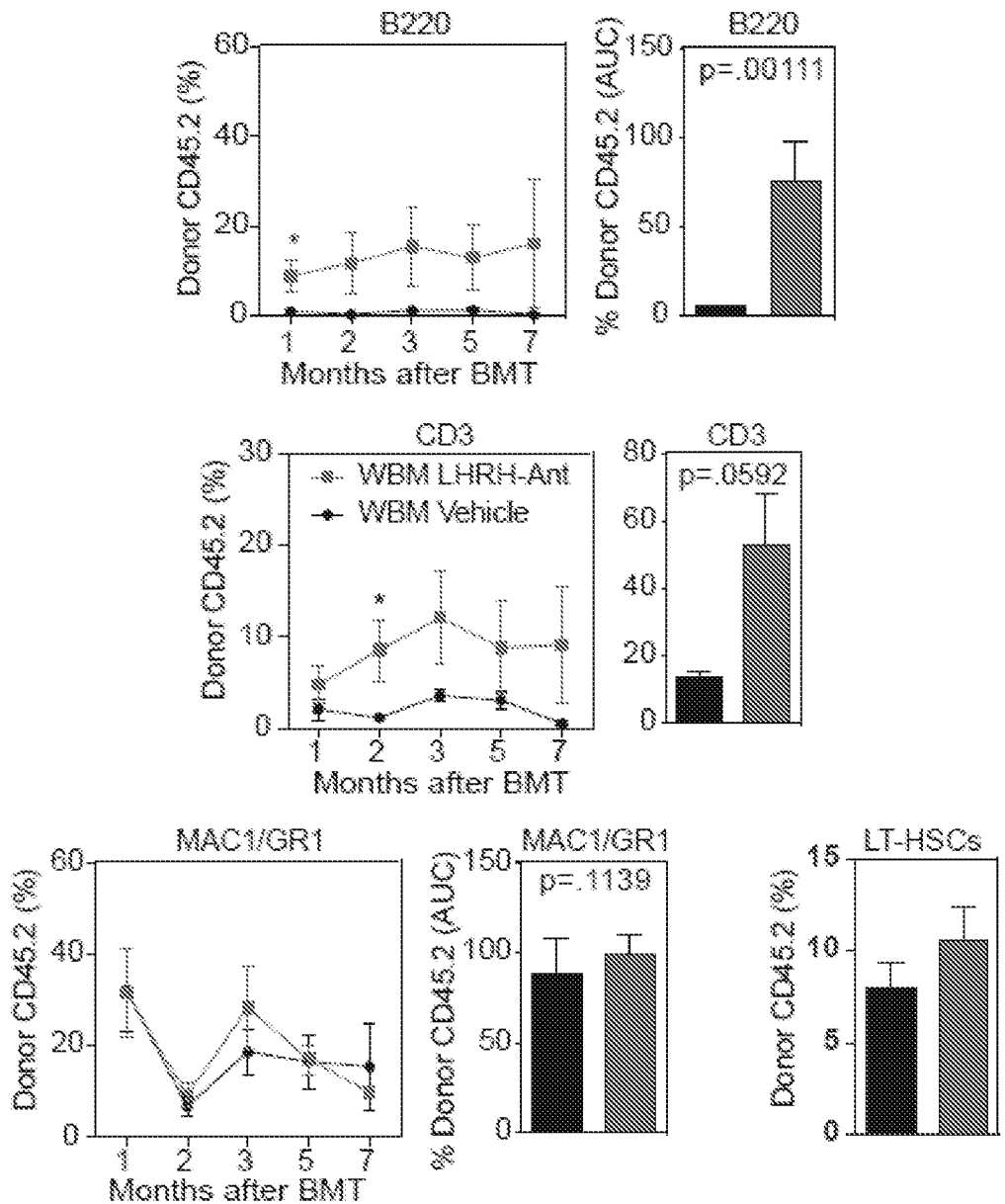
FIG. 3. Host mice receiving cells from LHRH-Ant-treated L-TBI mice had significantly better hematopoietic reconstitution than recipients of cells from vehicle-treated control L-TBI mice.

To investigate the specific regenerative effects mediated by LHRH-Ant treatment on the hematopoietic stem and progenitor cell (HSPC) compartment, BM were analyzed at several time points after L-TBI. In keeping with the peripheral blood (PB) recovery shown in FIG. 2B, BM cellularity of mice treated with the LHRH-Ant started to separate significantly from the vehicle group by day 14 after radiation (FIG. 2D). To determine hematopoietic functional potential, colony-forming unit activity was next quantified to determine the effects of LHRH-Ant on the recovery of committed hematopoietic progenitor cells. While there was no difference in total BM cellularity at day 7, there was a significant increase in CFU-GM and BFU-E colonies in L-TBI mice also treated with LHRH-Ant (FIG. 2E). Consistent with these functional findings, on day 14 after L-TBI, expansion of LSKs as well as their downstream progenitors in mice given LHRH-Ant were found (FIGS. 2F, 2G). Moreover, crucially for sustained hematopoiesis, significantly more LT-HSCs were also found (FIGS. 2F, 2G). However, given the changes in HSC phenotype after radiation, the standard competitive repopulation functional assay was adapted to evaluate the presence and relative quantity of functional HSCs after L-TBI. Specifically, all cells from the BM and spleen (to account for potential changes to circulating HSCs) were collected and transplanted from vehicle or LHRH-Ant treated mice at day 14 after L-TBI into irradiated hosts (along with a rescue dose of congenic WBM cells to ensure survival). This approach allowed detection of differences in the total number of residual HSCs which would be reflected by a functional difference in hematopoietic reconstitution. Host mice receiving cells from LHRH-Ant-treated L-TBI mice had significantly better hematopoietic reconstitution than recipients of cells from vehicle-treated control L-TBI mice (FIGS. 2H, 2I, and 3), showing that there greater number of functional HSCs persist in mice treated with LHRH-Ant. Taken together, these data show that pharmacological inhibition of the LHRH-receptor mitigated TBI-induced mortality and myelosuppression through protection and recovery of the HSC compartment.

Figure 4A:
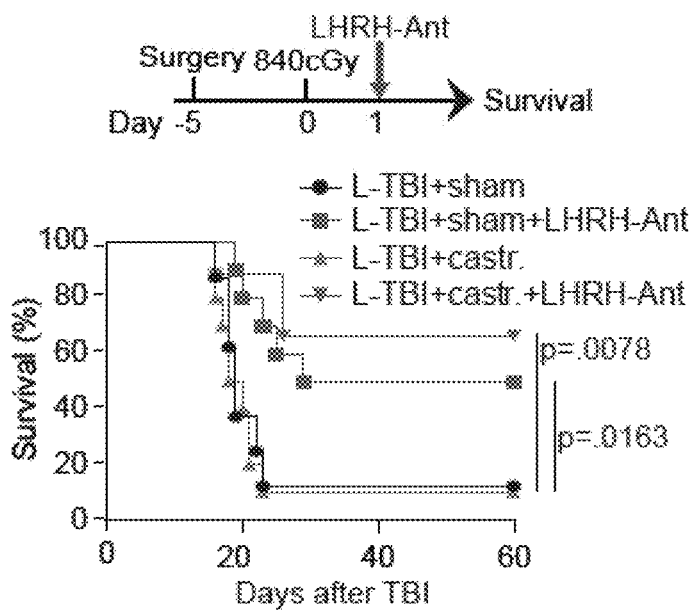
FIGS. 4A-4H. (4A) Surgical castration did not protect mice from radiation injury, but only the simultaneous treatment of the castrated mice with the LHRH-Ant restored the benefits in mouse survival. (4B) Consistent with the data in surgically castrated mice, MDV3100 alone did not mediate any survival benefit but in groups treated with both MDV3100 and LHRH-Ant there was a significant increase in mouse survival. (4C) Radiation by itself drastically reduced the levels of testosterone in both groups, and treatment with LHRH-Ant did not significantly lower the level of testosterone after radiation showing that the beneficial effects of LHRH-Ant on hematopoiesis and survival post irradiation were sex steroid independent. While levels of FSH did not change after L-TBI, levels of LH did decrease gradually over time and, as expected, LH and FSH were dramatically decreased in irradiated mice after LHRH-Ant treatment. (4D) Almost no detectable expression of the androgen receptor (AR) or follicle-stimulating hormone receptor (FSHR) was found on any of the HSPC subsets examined. In contrast, expression of luteinizing hormone/choriogonadotropin receptor (LHCGR) was highly enriched on long-term HSCs (LT-HSCs), and at comparable levels to those observed in the testes. (4E, 4F) Using recently identified surface markers enabling granular characterization of the human HSC compartment, LHCGR expression was significantly enriched in the most primitive HSC1 (Lin–CD34+CD38–CD45RA–CD90+CD49f+) and HSC2 (CD34+CD38–CD45RA–CD90–CD49f+); with expression nearly absent in downstream multi-potent progenitors (MPPs) and multi-lymphoid progenitors (MLPs). (4G) Administration of hCG abrogated the beneficial effects of LHRH-Ant on survival after radiation injury. (4H) LHCGR-KO mice had a modest but statistically significant increase in survival when exposed to L-TBI compared to littermate control mice.
Figure 4B:
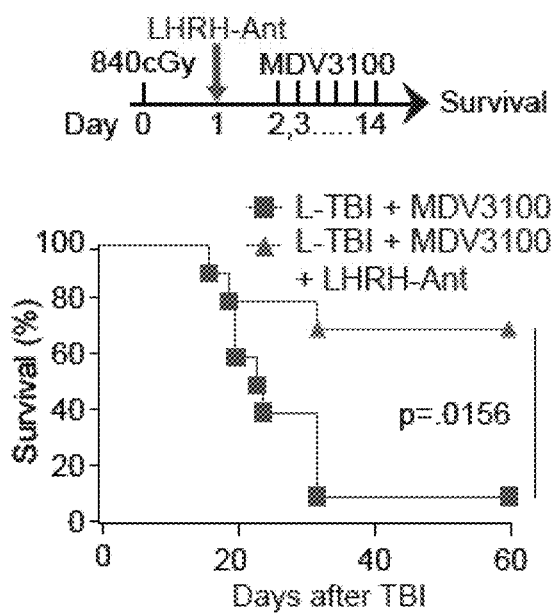

Given the previous report linking sex steroids to HSC function[5,7], the initial hypothesis was that LHRH-Ant facilitates hematopoietic recovery after radiation exposure through androgen ablation. To test this hypothesis and gain insight into the mechanisms driving the regenerative effects of LHRH-Ant, surgical castration was performed in male mice and their survival after L-TBI was followed. Surprisingly, surgical castration did not protect mice from radiation injury, but only the simultaneous treatment of the castrated mice with the LHRH-Ant restored the benefits in mouse survival (FIG. 4A). However, as surgery needed to be performed 5 days prior to TBI to ensure recovery by the time of irradiation, it could not be discounted that cessation of sex steroids before radiation mediates a separate effect. To account for this, mice were treated with the androgen receptor (AR) inhibitor enzalutamide (MDV3100) 24 h after L-TBI. Consistent with the data in surgically castrated mice, MDV3100 alone did not mediate any survival benefit but in groups treated with both MDV3100 and LHRH-Ant there was significant increase in mouse survival (FIG. 4B). These data strongly show that the inhibition of sex steroid activity, through surgical castration or pharmacological inhibition of AR signaling, did not represent the primary mechanism driving the regenerative effects mediated by LHRH-Ant treatment after radiation exposure. In line with the well-characterized toxic effects of radio-/chemo-therapy on gonads and fertility[17-20], radiation by itself drastically reduced the levels of testosterone in both groups (FIG. 4C), and treatment with LHRH-Ant did not significantly lower the level of testosterone after radiation (FIG. 4C); showing that the beneficial effects of LHRH-Ant on hematopoiesis and survival post irradiation were sex steroid independent.

Figure 4C:
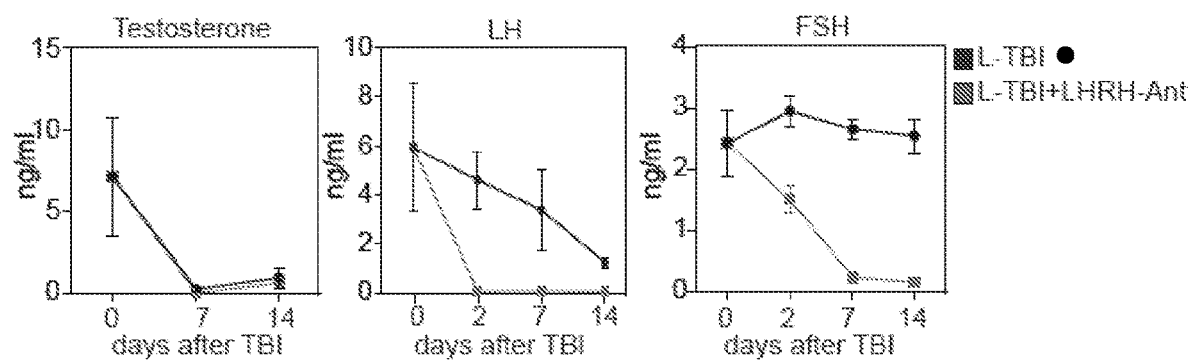

As LHRH exerts its effects in the pituitary, luteinizing hormone (LH) and follicle stimulating hormone (FSH), which are downstream of LHRH and upstream of sex steroids were then examined. While levels of FSH did not change after L-TBI, levels of LH did decrease gradually over time (FIG. 4C) and, as expected, LH and FSH were dramatically decreased in irradiated mice after LHRH-Ant treatment (FIG. 4C).

Figure 4D:
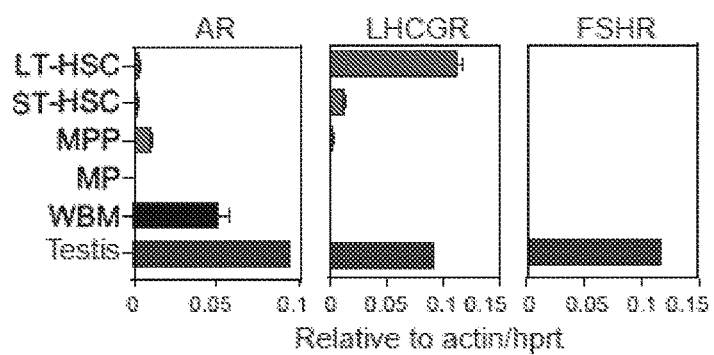
Figure 4E:
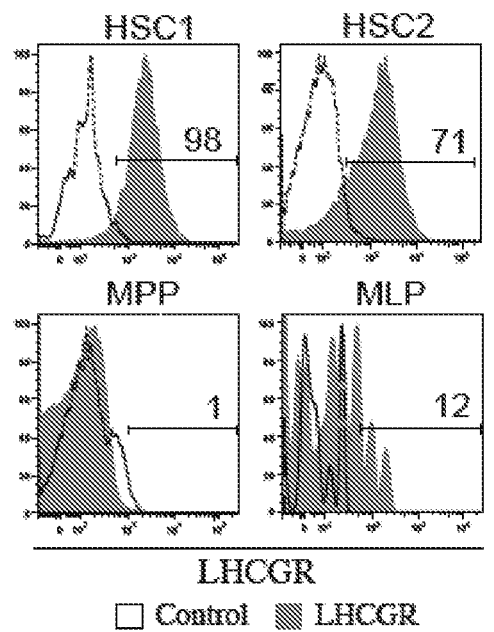
Figure 4F:
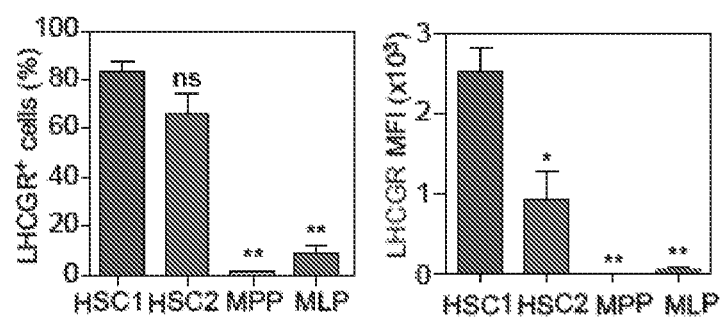
Figure 5C:
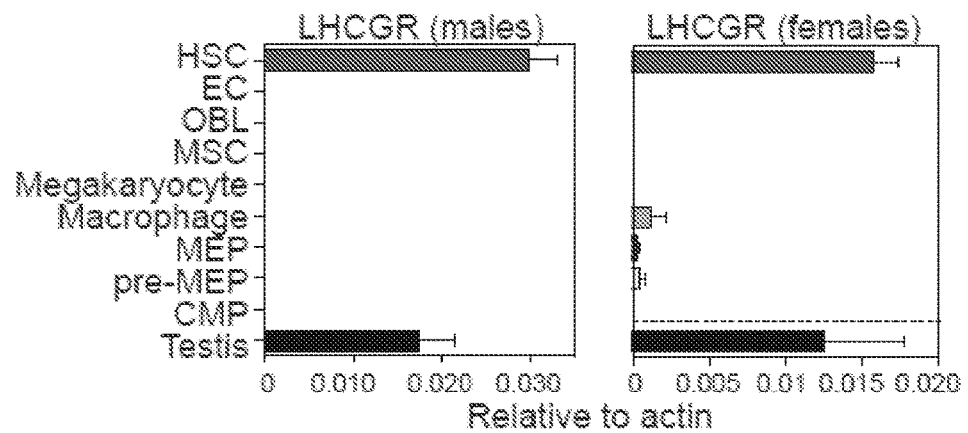
Figure 5D:
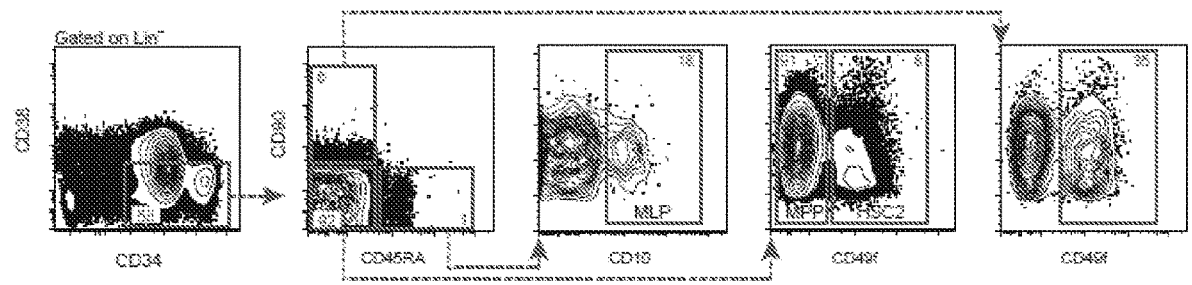

To gain some insights into the potential contribution of hormone signaling in hematopoiesis, the expression of AR as well as the LH and FSH receptors were analyzed on purified populations of HSPCs. Almost no detectable expression of the androgen receptor (AR) or follicle-stimulating hormone receptor (FSHR) was found on any of the HSPC subsets examined (FIG. 4D). In contrast, expression of luteinizing hormone/choriogonadotropin receptor (LHCGR) was highly enriched on long-term HSCs (LT-HSCs), and at comparable levels to those observed in the testes (FIG. 4D). Similar LHCGR expression pattern was also observed in HSCPs derived from female mice (FIG. 5B). Further analysis revealed that LHCGR expression was a peculiarity of LT-HSCs with little or no expression found on purified BM stromal cells (FIG. 5C). These findings were consistent with publically accessible gene expression databases[21,22]. Using recently identified surface markers enabling granular characterization of the human HSC compartment (FIG. 5D)[23,24], LHCGR expression was significantly enriched in the most primitive HSC1 (Lin−CD34+ CD38−CD45RA−CD90+CD49f+) and HSC2 (CD34+ CD38−CD45RA−CD90−CD49f+); with expression nearly absent in downstream multi-potent progenitors (MPPs) and multi-lymphoid progenitors (MLPs) (FIGS. 4E, 4F). Although LHCGR expression has previously been shown in a crude fraction of Lin−CD45+ Sca1+ cells[3], this is the first evidence of its enriched expression on the most primitive HSCs.

Figure 4G:
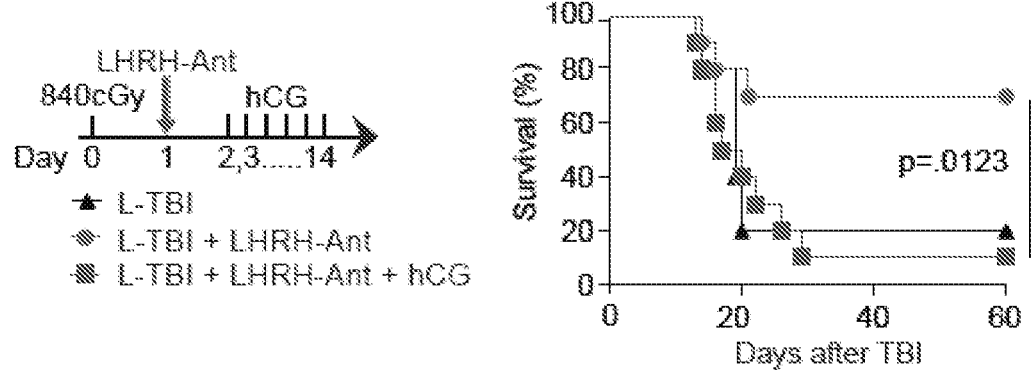

Given restricted expression of LHCGR to the primitive HSC compartment, it was sought to definitively determine whether the regenerative effects of LHRH-Ant treatment depended specifically on LH suppression. For this LHCGR was re-stimulated in LHRH-Ant treated mice that had been given L-TBI 1 day prior. For these studies the alternative LHCGR ligand human chorionic gonadotropin (hCG) was employed due to its longer half-life compared to LH (60-120 minutes for LH, several hours for hCG) and its wide use in routine laboratory procedure to stimulate the LHCGR[25,26]. Consistent with the hypothesis, administration of hCG abrogated the beneficial effects of LHRH-Ant on survival after radiation injury (FIG. 4G).

Figure 4H:
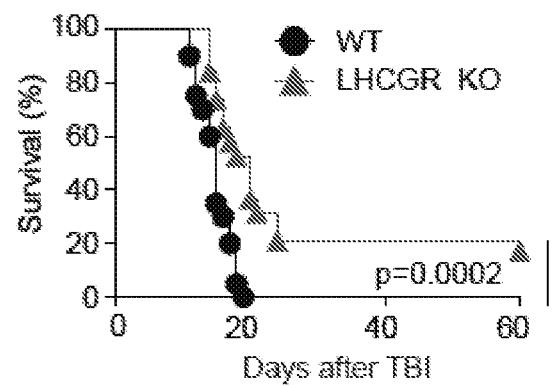

Given the negative impact of LH signaling on HSC during hematopoietic recovery after radiation, it was hypothesized that mice deficient for LHCGR could be radio protected when exposed irradiation. The results showed that LHCGR-KO mice had a modest but statistically significant increase in survival when exposed to L-TBI compared to littermate control mice (FIG. 4H).

Figure 6A:
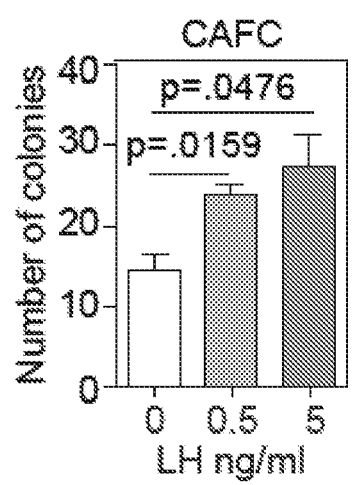
FIGS. 6A-6G. (6A, 6B) LH significantly enhanced colony formation in cobblestone area-forming cell (6A; CAFC) and colony-forming cell (6B; CFC) assays. (6C) LH was also able to significantly expand human HSC1 in vitro (CD34+CD38–CD45RA–CD90+) in a stroma-free culture system. (6D) When cell cycle status of HSCs in LHRH-Ant treated mice after L-TBI was analyzed, a significantly higher proportion of Ki-67$^-$ quiescent LT-HSCs in the LHRH-Ant-treated group with fewer proliferative HSCs compared to the vehicle group was found. (6E, 6F) Aablation of LH production in mice using a luteinizing hormone-releasing hormone-antagonist (LHRH-Ant) retained significantly more LT-HSCs in G0 in both models. (6G) Using the same administration scheme as described in FIG. 3F it was revealed that LHRH-Ant treatment significantly increased the proportion of live LT-HSCs compared to vehicle treated mice FIG. 7. When cell cycle status of HSCs in LHRH-Ant treated mice after L-TBI was analyzed, a significantly higher proportion of Ki-67$^-$ quiescent LT-HSCs in the LHRH-Ant-treated group with fewer proliferative HSCs compared to the vehicle group was found.
Figure 6B:
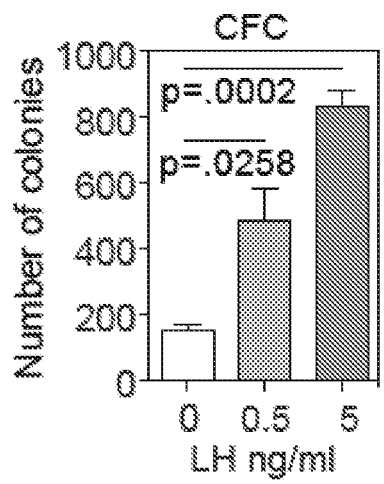
Figure 6C:
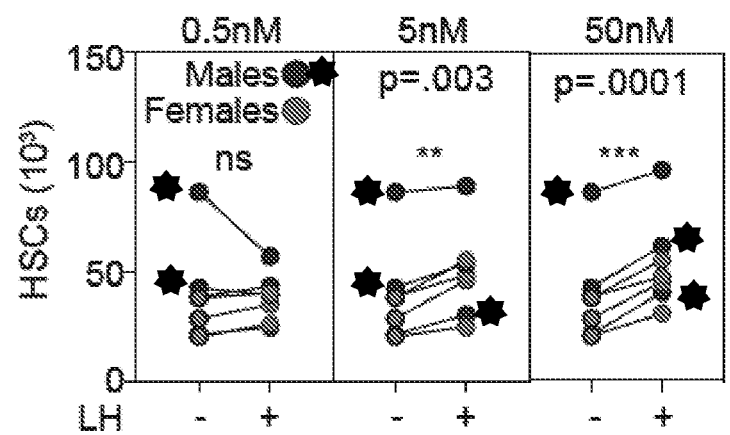
Figure 6D:
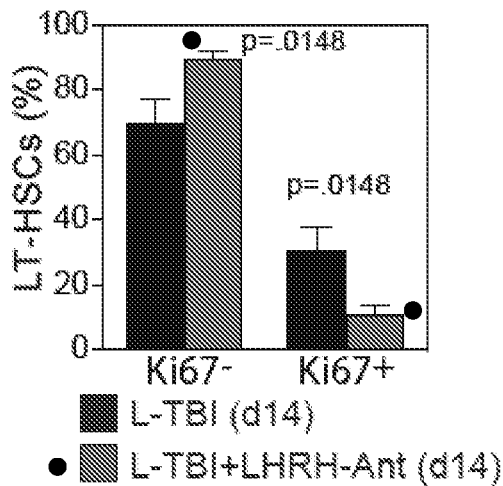
Figure 7:
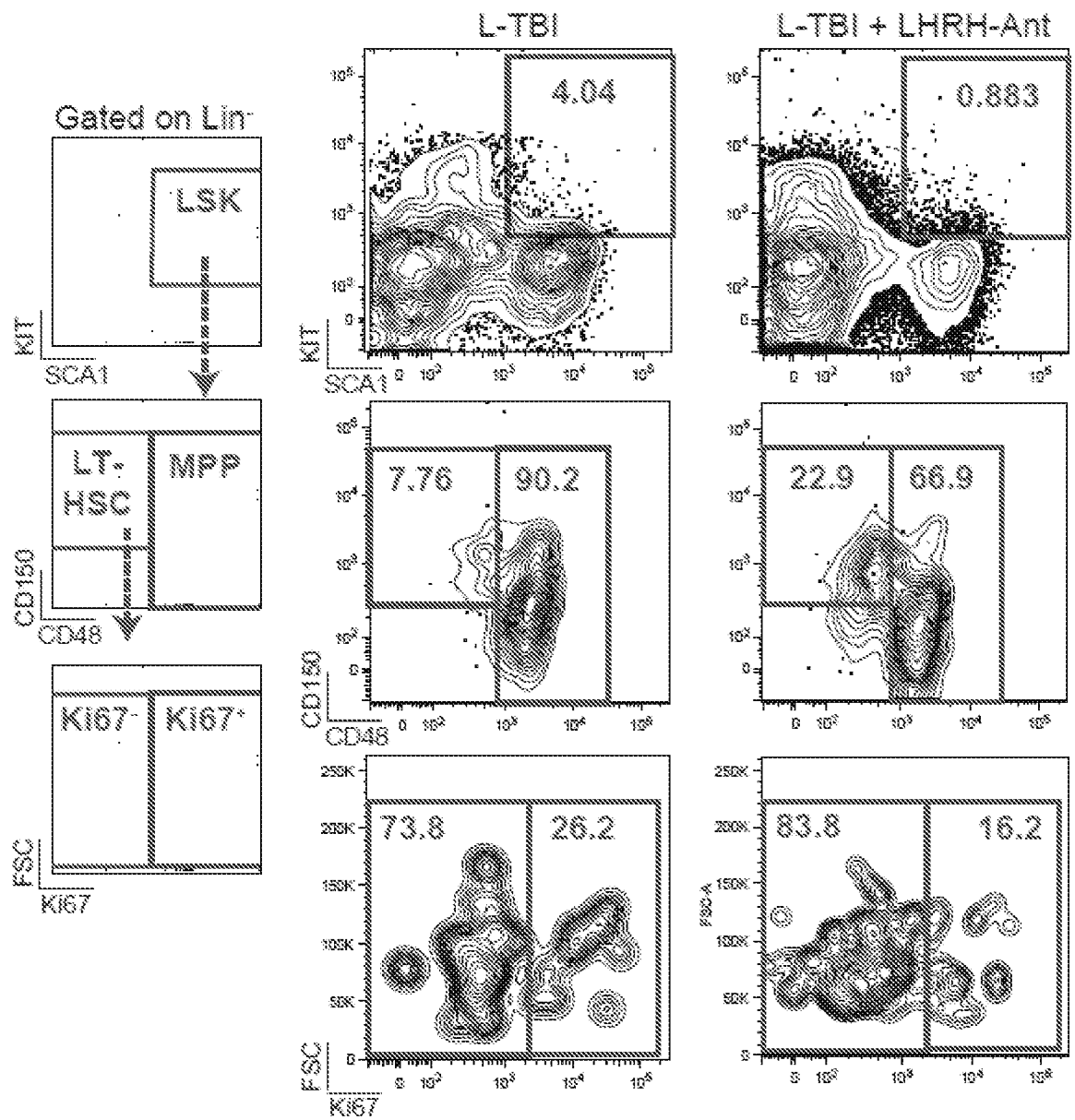

The control of HSC self-renewal, differentiation, and proliferation is a tightly regulated process crucial for maintaining the HSC pool[29-34]. This is particularly relevant during hematopoietic injuries (such as high dose or repeated rounds of chemotherapy or irradiation) when dormant HSCs transiently start to proliferate to replenish blood cells as unbalanced HSC proliferation can lead to stem cell exhaustion and long-term myelosuppression[35-37]. Consistent with its previously described role in promoting proliferation of primary cells, including gonadal and neuronal cells[38-40], LH significantly enhanced colony formation in cobblestone area-forming cell (CAFC) and colony-forming cell (CFC) assays (FIGS. 6A, 6B). Importantly, LH was also able to significantly expand human HSC1 in vitro (CD34+CD38−CD45RA−CD90+) in a stroma-free culture system (FIG. 6C). Although there is a clear need for HSC proliferation to ensure regenerative hematopoiesis, previous reports have also shown that induction of HSC quiescence after high-dose irradiation correlates with increased hematopoietic recovery and enhanced mouse survival[35,37,41]. Taken together these findings show that abrogation of LHCGR signaling after TBI promotes HSC quiescence and thus survival. Consistent with this hypothesis, when cell cycle status of HSCs in LHRH-Ant treated mice after L-TBI was analyzed, a significantly higher proportion of Ki-67− quiescent LT-HSCs in the LHRH-Ant-treated group with fewer proliferative HSCs compared to the vehicle group was found (FIG. 6D and FIG. 7). This showed that the inhibition of LH signaling retains HSCs in a quiescent phase and protected them from LH-induced entry into the cell cycle after high-dose irradiation.

Figure 6E:
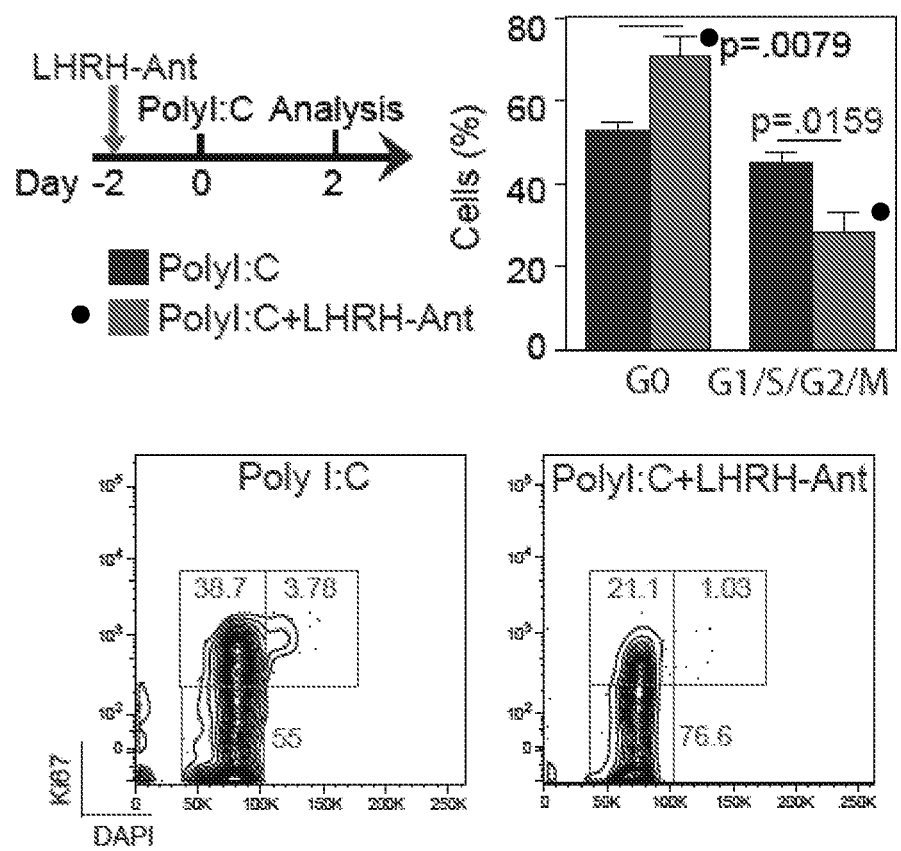
Figure 6F:
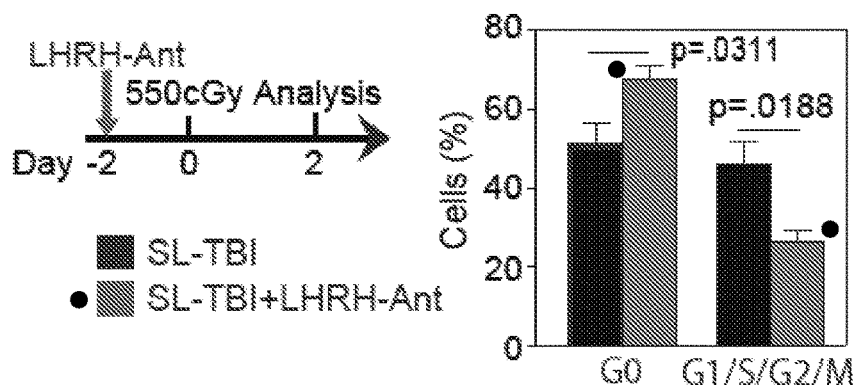
Figure 6F:
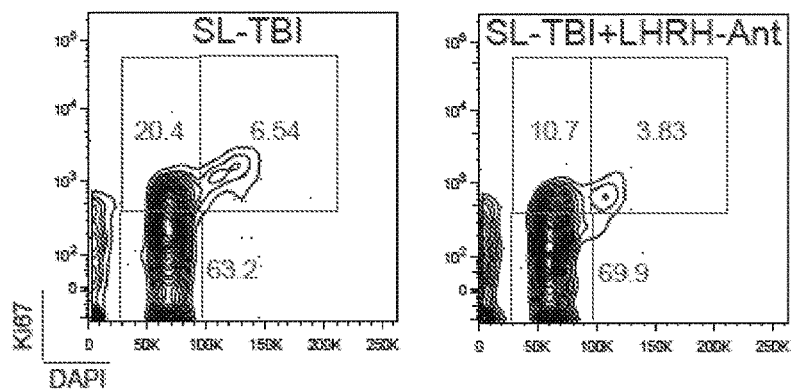
Figure 6G:
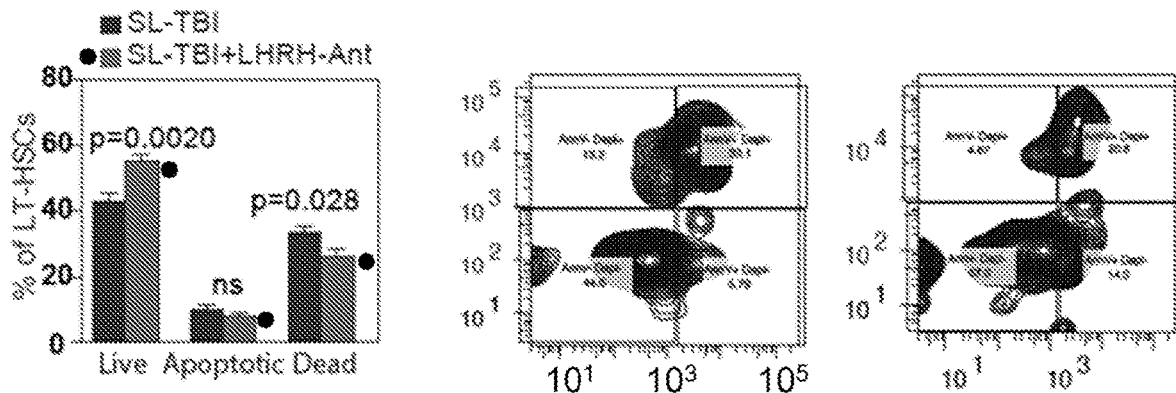

To further validate this hypothesis, two additional models were used to force HSCs out of their quiescence phase, Poly I:C and sub-lethal dose of total body irradiation (SL-TBI)[35,42,43]. To eliminate any potential effects of downstream sex steroids on HSCs, all cohorts of mice in these studies had been surgically castrated. Consistent with the hypothesis, ablation of LH production in mice using a luteinizing hormone-releasing hormone-antagonist (LHRH-Ant) retained significantly more LT-HSCs in G0 in both models (FIGS. 6E, 6F). To evaluate if promoting HSC quiescence resulted in increased cell viability after radiation exposure cell apoptosis was analyzed using AnnexinV/DAPI staining. Using the same administration scheme as described in FIG. 3F it was revealed that LHRH-Ant treatment significantly increased the proportion of live LT-HSCs compared to vehicle treated mice (FIG. 6G).

Figure 8A:
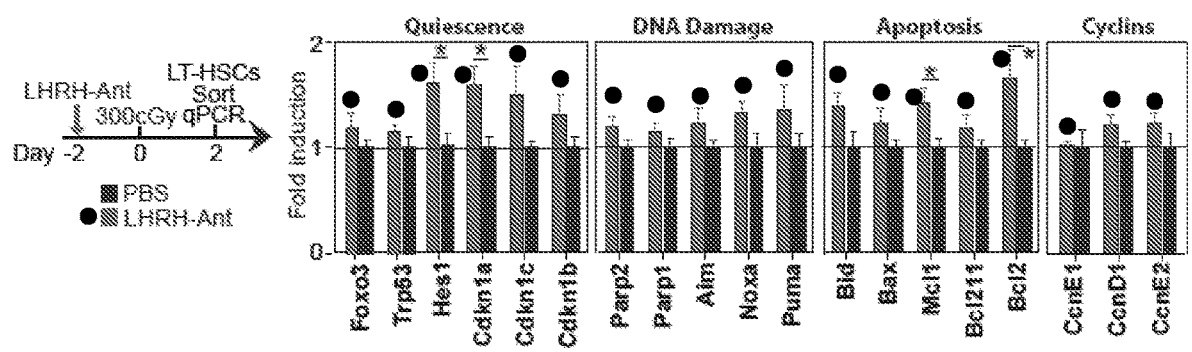
FIGS. 8A-8E. (8A) LT-HSC derived from LHRH-Ant-treated mice showed significant overexpression of genes related to quiescence and apoptosis (p=0.02 and p=0.004, respectively). (8B) Abrogation of LH production significantly improved survival after serial 5-FU challenge. (8C) Ablation of LH can limit HSC entry into cell cycle thus promoting their quiescence and survival during hematopoietic insult. (8D) Constitutive LHCGR signaling in kiLHR HSCs significantly promoted reduction in LT-HSC survival after radiation exposure, as measured by higher proportion of apoptotic cells. (8E) Pharmacological inhibition of LH signaling using a single dose of an LHRH-Ant represents a rational and feasible approach to preserve the HSC pool after high dose radiation, thereby mitigating acute hematopoietic radiation syndrome.

To gain some insights in to the molecular changes mediated by LHRH-Ant treatment on HSCs LT-HSCs were purified after 300 cGy irradiation and expression of key genes associated with quiescence, proliferation, DNA damage response and apoptosis of HSCs was assessed. Broadly, it was observed that LT-HSC derived from LHRH-Ant-treated mice showed significant overexpression of genes related to quiescence and apoptosis (p=0.02 and p=0.004, respectively) (FIG. 8A). Specifically, within these categories, significantly higher levels of Hes1 and Cdkn1a (p21), two genes previously identified to be critical in promoting HSC quiescence[34,44]; as well as the anti-apoptotic genes Bcl2 and Mcl1, which were both significantly increased in the LHRH-Ant treated samples were found. Importantly, both Bcl-2 and Mcl-1 have been implicated in regulating HSC quiescence and survival respective[45,46].

Figure 8B:
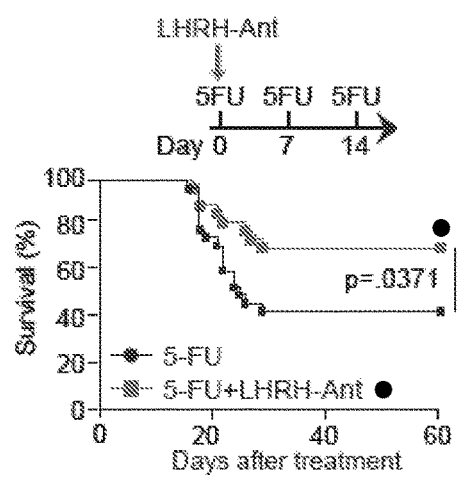

To test whether this LHRH-Ant-mediated preservation of HSC quiescence and enhancement of HSC survival after hematopoietic stress could confer protection against chemotherapy-induced myeloablation, mice were challenged with successive doses of 5-fluorouracil (5-FU); a well-established method to functionally test HSC proliferation and self-renewal that leads to ablation of proliferating HSCs and ultimately death[29,34,47]. Abrogation of LH production significantly improved survival after serial 5-FU challenge (FIG. 8B), supporting a role in promoting HSC quiescence. Together, these results show that ablation of LH can limit HSC entry into cell cycle thus promoting their quiescence and survival during hematopoietic insult.

Figure 8C:
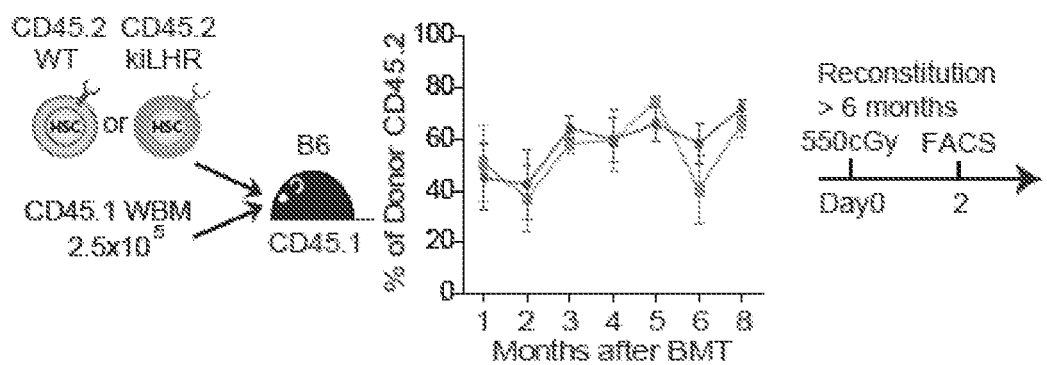
Figure 8D:
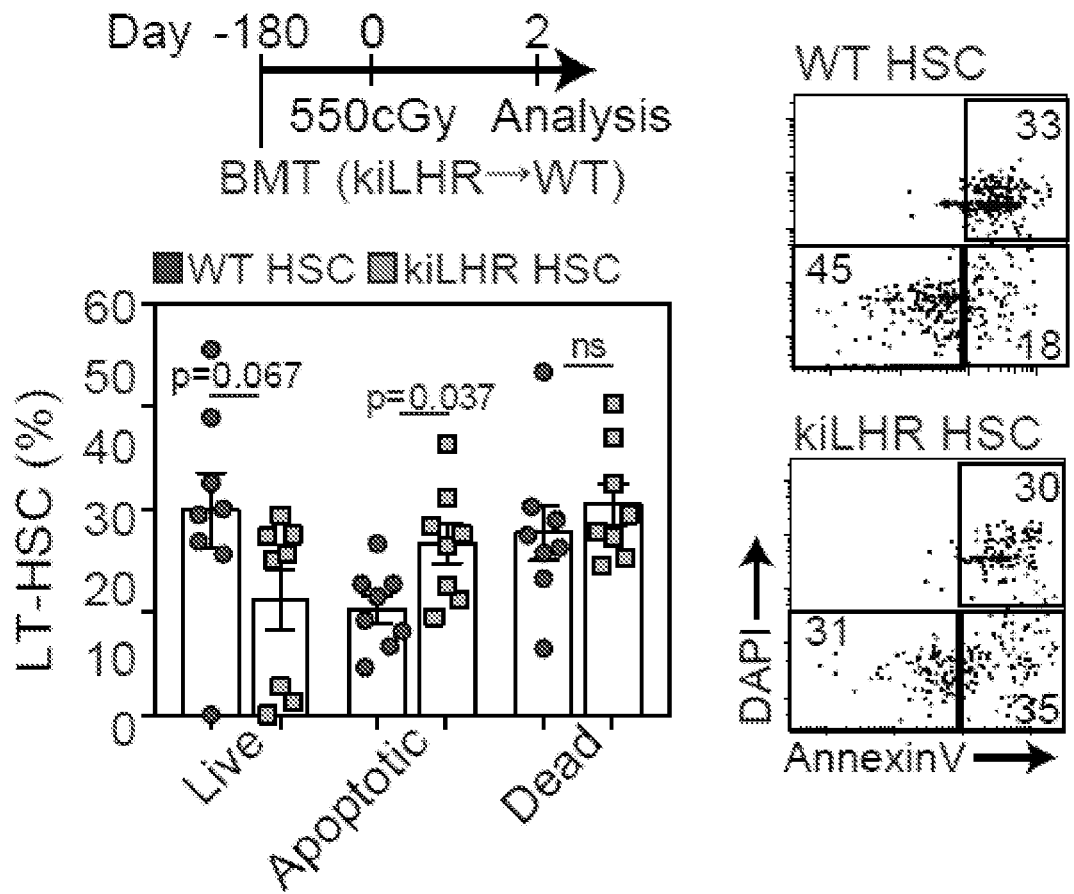

To evaluate the cell intrinsic effects of LHCGR stimulation in HSCs, repopulating experiments were performed with LT-HSCs purified from WT or kiLHR mice, which have a gain of function mutation (D582G) that makes the LHCGR constitutively active[40,48]. Peripheral blood analysis of donor reconstitution did not reveal any difference over the time course analyzed, showing that signaling of LHCGR is redundant for HSC repopulating potential and survival (FIG. 8C). Rather, it was hypothesized that stimulation of the LH receptor could be detrimental to cells that have undergone hematopoietic stress themselves and then need to proliferate in response to hematopoietic injury. Therefore, mice that had been reconstituted for 6 months with WT or kiLHR were exposed to SL-TBI and cell apoptosis was evaluated two days later. Consistent with previous findings, constitutive LHCGR signaling in kiLHR HSCs significantly promoted reduction in LT-HSC survival after radiation exposure, as measured by higher proportion of apoptotic cells (FIG. 8D).

Figure 8E:
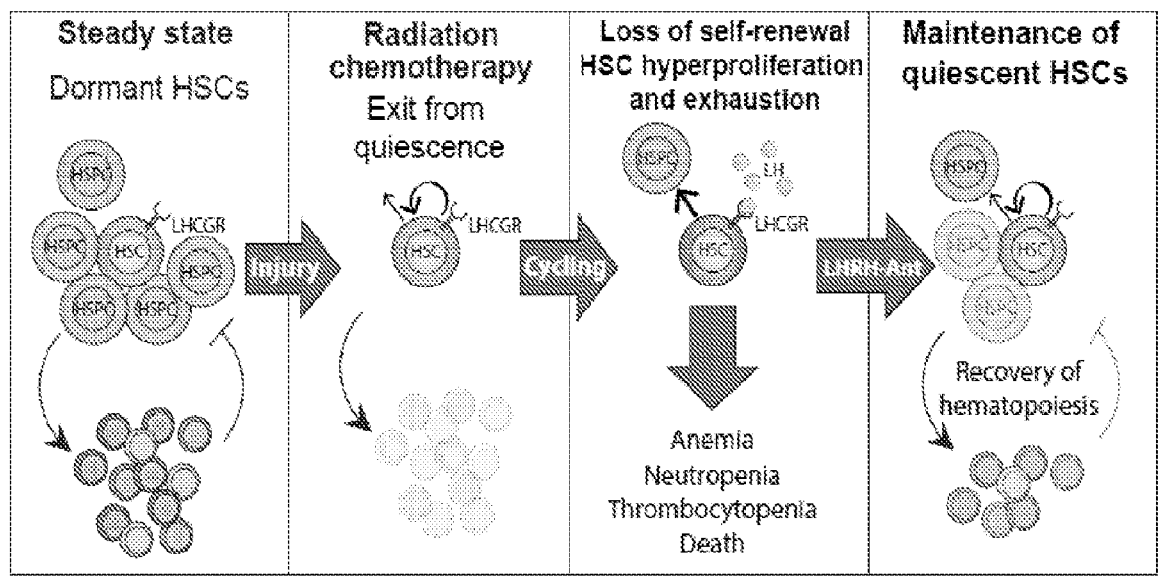
Figure 9A:
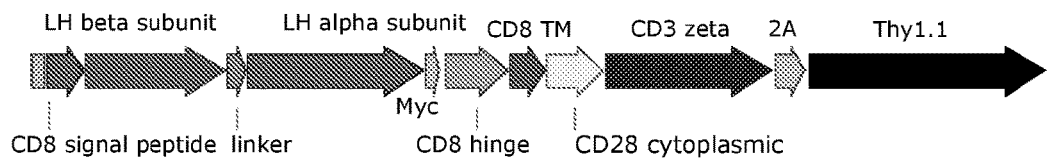
FIGS. 9A, 9B. Schematics of mouse and human LH-CAR designs.
Figure 9A:
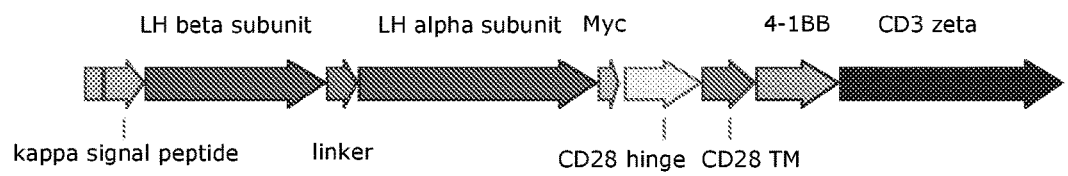
Figure 9B:
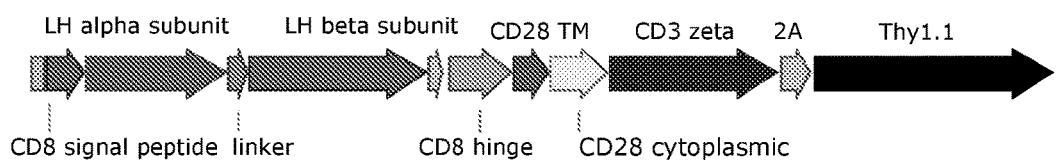
Figure 9B:
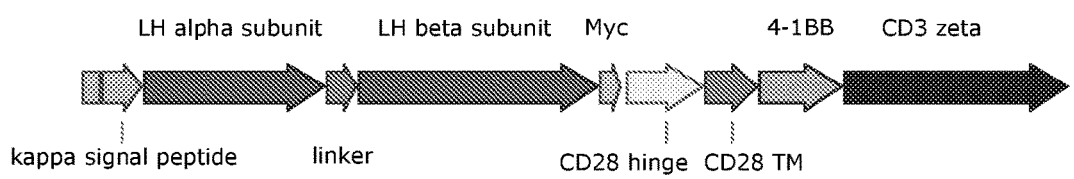

Taken together the disclosure demonstrates that pharmacological inhibition of LH signaling using a single dose of an LHRH-Ant represents a rational and feasible approach to preserve the HSC pool after high dose radiation, thereby mitigating acute hematopoietic radiation syndrome (FIG. 8E). Contrary to the initial hypothesis, this was not mediated by sex steroids, but rather due to LH signaling through the most primitive HSCs, promoting their proliferation and leading to increased cell death. LH levels and HSC activity change considerably during several physiological conditions, including pregnancy, aging, stress, exercise and circadian rhythm, all of which have been implicated in hematopoiesis. These findings thus also lay the groundwork for revealing a potential role for LH in a range of aberrant hematopoietic conditions.

Methods. Mice: C57BL/6 (CD45.2) male mice (The Jackson Laboratory, MA) were used at 7 to 8 weeks of age. B6.SJL-Ptprca Pepcb/BoyJ (CD45.1) male mice (The Jackson Laboratory) were used between 7 and 12 weeks of age for transplant. Mice were irradiated with a Gammacell 40 Irradiator (Cs-137), with an average dose rate of 95 cGy/min, in a plexiglass mouse pie cage. To assess mouse survival after radiation, mice were monitored for up to 60 days after TBI. To adjust for differences in weight, identical mice were purchased from Jackson and cages randomly distributed over different groups. All animal protocols were approved by the Memorial Sloan Kettering Cancer Center Institutional Animal Care and Use Committee.

Reagents: Degarelix (as acetate), a LHRH-Ant (Firmagon), was resuspended in sterile water for injection and administered S.C. to mice at a dose of 40 mg/kg. To evaluate the radiomitigative effect of LHRH-Ant on survival, mice were treated subcutaneously (S.C.) with a single injection of the LHRH-Ant or a saline control solution (PBS). Degarelix was purchased from the Memorial Sloan-Kettering Cancer Center Pharmacy. Poly I:C (InvivoGen) was administered I.P to mice at a dose of 5 mg/kg. hCG (cellsciences) was resuspended in sterile PBS and administered S.C. to mice at a dose of 20 1U. LH from human pituitary (SIGMA) was resuspended in PBS for in vitro studies. MDV3100 (selleckchem) was resuspended in a mixture of 45% PBS, 45% PEG and 10% DMSO and administered daily to mice by oral gavage at a dose of 10 mg/kg. 5-FU (InvivoGen) was administered to mice intraperitoneally (I.P.) at a dose of 150 mg/kg once every 7 days consecutively for 3 times as previously described[34,47,49].

Colony-Forming Cell (CFC) and Cobblestone Areas Forming Cell (CAFC): Assays were performed as previously described with a minor modifications[50]. For CFC assays, $5 \times 10^4$ BM nucleated cells (BMNC) per 1 mL of Iscove's modified Dulbecco's medium (GIBCO) supplemented with 1.2% methylcellulose (Dow Chemicals, MI), 30% FBS, 2 mM glutamine, 0.1 mM monothioglycerol, 0.1 mg/ml hemin (Sigma Inc, MO), 0.05 mg gentamicin, 20 ng/mL murine c-kit ligand (Amgen Inc, CA), 6 units/ml human Epogen (Amgen Inc. CA), and 20 ng/mL murine IL-3 (Pepro Tech Inc., NJ) were plated in triplicates in 35-mm non-tissue culture dishes (Corning-Costar, NY). When there were fewer BMNC, all the BM cells were equally plated to Petri dishes in triplicates. Colonies were scored after 10 days of incubation at 37° C. and 5% CO2. For the CAFC assays, murine stromal cells MS-5[51] (kindly provided by Dr. KJ Mori, Niigata University, Niigata, Japan), was maintained in MEM alpha containing 10% FCS, 50 µg/ml gentamicin and tested with a MycoAlert Plus *mycoplasma* kit (Lonza) to ensure *mycoplasma*-free. When the MS-5 culture reached 90% confluence, the culture was passaged in 1:8 dilution. Two days prior to CAFC assay, confluent MS-5 cells were harvested, and $0.8-1 \times 10^5$ MS-5 cells/12.5 cm2 flasks were plated and cultured. For CAFC assay, $1.5-3 \times 10^3$ purified LSK cells were co-cultured with the confluent MS-5 cells in 3 ml of a-MEM containing 12.5% FBS (Atlanta Biologicals, GA), 12.5% horse serum (GE Health Life Science, Utah), 1 µM Hydrocortisone (Sigma Inc, MO) and $5 \times 10^{-5}$ M 2-mercaptoethanol (Fisher Scientific) in triplicates at 37° C. and 5% $CO_2$. Half of the culture medium was replenished weekly. After 3 weeks of co-culture, CAFCs were scored as phase-dark hematopoietic clones of at least 5 cells beneath the stromal layer using an inverted microscope.

In vitro effect of LH of HSCs, CAFC and CFC assays.

Mouse cells: Two thousand purified LSK cells and MS-5 cells were co-cultured in T-12.5 flasks with or without 0.5 or 5 µg/ml of LH in 4 replicates. LH was added daily for 3 day and media replenished with an half of fresh CAFC medium weekly. After three weeks, CAFC were scored. The co-cultures were further harvested by washing with 3 ml of cold PBS 3 times and detached with 0.05% trypsin solution. The harvested co-culture medium, the washes and the detached cells were pooled, pelleted and subjected to CFC bioassay.

Human cells: Human umbilical cord blood (UCB) CD34+ cells were harvested, enriched and cultured as previously described[52]. Briefly before enrichment of NHP CD34+ cells, red cells were lysed in ammonium chloride lysis buffer. For enrichment of human CD34+ cells, microbead conjugated anti-CD34 antibody (Miltenyi Biotech) was used. Enriched and sort-purified CD34+ cells were cultured in StemSpan (Stemcell Technologies) supplemented with 100 U/ml penicillin streptomycin (Gibco by Life Technologies) and SCF, TPO and FLT3-L (all Peprotech) (100 ng/ml each) with 50% exchange of culture medium on day 4. Fresh LH was added every day for the total duration of in vitro culture. For CFC assays 400 sorted cells were seeded into 1 ml MethoCult H4435 (StemCell Technologies). Hematopoietic colonies were scored after 12-14 days. Arising colonies were identified as colony forming unit-(CFU-) granulocyte (CFU-G), macrophage (CFU-M), granulocyte-macrophage (CFU-GM) and burst forming unit-erythrocyte (BFU-E). Colonies consisting of erythroid and myeloid cells were scored as CFU-MIX.

Flow cytometry and cell cycle analysis: Monoclonal antibodies recognizing the following markers were used for flow cytometric analyses and cell sorting of murine cells (LSR II or FACSAria III, BD Biosciences): (from BD Pharmingen) c-kit (2B8), Sca-1 (D7), CD11b (M1/70), CD11c (HL3), CD19 (ID3), CD3c (145-2C11), CD34 (RAM34), CD45 (30-F11), CD45.1 (A20), CD45.2 (104), CD48 (HM48-1), CD62L (MEL-14), CD135 (A2F10.1), Gr-1 (RB6-8C5), NK1.1 (PK136), TER-119 (TER-119); (from eBioscience) CD127 (A7R34), CD150 (mShad150); (from Invitrogen) B220 (RA3-6B2) and streptavidin (N/A). The mouse lineage antibody cocktail included anti-CD3, anti-CD4, anti-CD8α, anti-CD19, anti-CD11b, anti-CD11c, anti-Gr-1, anti-NK1.1, and anti-TER119. The following antibodies were used for flow cytometry analyses of human samples, CD49f (eBioGoH3), CD45RA (L48), CD34 (581), CD38 (HIT2). CD90 (5E10), CD10 (Hl10a). The human lineage antibody cocktail included anti-CD3, anti-CD14, anti-CD16, anti-CD19, anti-CD20, anti-CD56. To detect human LHCGR a polyclonal anti-LHCGR (Alomone, cat #: ALR-010) was used. For intracellular Ki67/DAPI staining, BM cells were stained with surface markers, fixed, and permeabilized using the Fixation/Permeabilization kit (cat. 00552100 ebioscience) and permeabilization buffer (cat. 008333 ebioscience). Cells were then incubated with Ki67-Alexa 700 (B56) (from BD Biosciences) for 45 minutes at 4 C. After centrifugation DAPI (5ug/ml) was added to cells and allowed to incubate for at least 30 min at RT before analysis.

Cell isolation and cord blood processing: BM cells were flushed from intact femurs and tibia, and spleens were mashed with glass slides to generate single-cell suspension. Collection of the cells was performed in RPMI media with 10% FBS or PBS with 0.5% BSA, and filtered through a 70-µm strainer. Unless otherwise stated, all cell numbers in this study were standardized as total counts per two legs or per spleen. Human cord bloods were obtained from New York Blood Center. Cord bloods were processed separately in each experiment. An equal volume of phosphate buffered saline was added prior to layering on Ficoll/Paque gradient and samples were processed according to manufacturer's protocol. CD34+ cells were enriched by magnetic separation using human CD34 MicroBead kit (Miltenyi Biotec).

Bone marrow transplant: In the competitive BM transplant, whole BM from CD45.2+ (vehicle or LHRH-Ant) donors and were collected and transplanted into lethally irradiated CD45.1+ mice (1100 cGy TBI, split dose) along with $2.5 \times 10^5$ CD45.1+ competitors, through tail vein injection. Donor chimerism was monitored monthly after transplant. In the LSK transplant, lineage-Sca-1+c-Kit+ cells from BM were selected using a FACS Aria II cell sorter (BD).

Real time PCR: Reverse transcription-PCR was performed with QuantiTect reverse transcription kit (QIAGEN). For real-time PCR, specific primer and probe sets were obtained from Applied Biosystems as follows: β-actin (Mm01205647_g1); HPRT (Mm00446968_m1); AR (Mm00442688_m1); FSHR (Mm00442819_m1); LHCGR (Mm00442931_m1). PCR was done on ABI 7500 (Applied Biosystems) or Step-One Plus (Applied Biosystems) with TaqMan Universal PCR Master Mix (Applied Biosystems). Relative amounts of mRNA were calculated by the Ct method.

Statistics: Bars and error bars represent the mean+SEM for the various groups. For most experiments, nonparametric testing was performed if normal distribution could not be assumed. All tests performed are two sided. Statistical analysis between two groups was performed with the nonparametric, unpaired Mann-Whitney U test. Tests performed are two sided, except for gene category analysis. Differential expression of gene categories was computed using Fisher's method and the input p-value for each individual gene from a category is computed from a one sided test. Survival data were analyzed with the Mantel-Cox log-rank test. Parametric t test was used for FIG. 6H right panel. The experiments were not randomized and the investigators were not blinded to the group allocation during the experiments or when assessing the outcomes. To ensure adequate power for statistical analysis at least five samples per group were tested. In general variation within groups and between experiments was low, however to take into account inter-experimental variation all experiments were performed at least twice. To account for intra-experimental variation, particularly for in vitro studies, several wells per conditions were assessed with primary sample material coming from at least two different mice. No samples or animals were excluded from the analysis except for mouse peripheral blood analysis where outliers were detected prior to the analysis with two-sided Grubbs' test for outliers (GraphPad). All statistics were calculated and display graphs generated using GraphPad 6.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in the ability to enrich for and isolate, expand and/or ablate pHSC.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

EXAMPLE 1 REFERENCES

1. Dainiak, Experimental hematology 30, 513-528 (2002).
2. Anno, et al., Health Phys 84, 565-575 (2003).
3. Mierzejewska, et al., Hematopoietic Stem/Progenitor Cells Express Several Functional Sex Hormone Receptors-Novel Evidence for a Potential Developmental Link Between Hematopoiesis and Primordial Germ Cells. Stem cells and development (2015).
4. Sanchez-Aguilera, et al., Cell stem cell 15, 791-804 (2014).
5. Nakada, et al., Nature 505, 555-558 (2014).
6. Dudakov, et al., Journal of Immunology 183, 7084-7094 (2009).
7. Khong, et al., Enhanced Hematopoietic Stem Cell Function Mediates Immune Regeneration following Sex Steroid Blockade. Stem cell reports (2015).
8. Thurmond, et al., Endocrinology 141, 2309-2318 (2000).
9. Williams, et al., Radiat Res 173, 557-578 (2010).
10. Drouet, & HerodinInt J Radiat Biol 86, 636-648 (2010).
11. Herodin, & Drouet, Experimental hematology 33, 1071-1080 (2005).
12. Koukourakis, Br J Radiol 85, 313-330 (2012).
13. Singh & Yadav, Exp Mol Pathol 78, 156-169 (2005).
14. Dudakov, et al., Journal of Immunology 182, 6247-6260 (2009).
15. Goldberg, Journal of Immunology 184, 6014-6024 (2010).
16. Velardi, et al., Sex steroid blockade enhances thymopoiesis by modulating Notch signaling. J Exp Med (2014).
17. Delic, et al., The British journal of cancer. Supplement 7, 105-107 (1986).
18. Delic, et al., Radiotherapy and oncology: journal of the European Society for Therapeutic Radiology and Oncology 5, 29-37 (1986).
19. Shalet, et al., The Journal of endocrinology 120, 161-165 (1989).
20. Meistrich, Pediatric blood & cancer 53, 261-266 (2009).
21. Heng, Painter, & Immunological Genome Project, C. Nat Immunol 9, 1091-1094 (2008).
22. Seita, et al., PLoS One 7, e40321 (2012).
23. Huntsman, et al., Blood 126, 1631-1633 (2015).
24. Notta, et al., Science 333, 218-221 (2011).
25. Luo, et al., Journal of the American Association for Laboratory Animal Science: JAALAS 50, 471-478 (2011).
26. Choi & Smitz, Molecular and cellular endocrinology 383, 203-213 (2014).
27. Zhang, et al., Mol Endocrinol 15, 172-183 (2001).
28. Lei, et al., Mol Endocrinol 15, 184-200 (2001).
29. Tsai, et al., Nature cell biology 15, 309-316 (2013).
30. Kharas, et al., Blood 115, 1406-1415 (2010).
31. Kharas, & Gritsman, Cell cycle 9, 1223-1224 (2010).
32. Wang, et al., Genes Dev 25, 1426-1438 (2011).
33. Wang et al., Blood 107, 358-366 (2006).
34. Cheng, et al., Science 287, 1804-1808 (2000).
35. Johnson, et al., J Clin Invest 120, 2528-2536 (2010).
36. Chen, et al., J Exp Med 205, 2397-2408 (2008).
37. Himburg, et al., J Clin Invest 124, 4753-4758 (2014).
38. Mak, et al., Nature neuroscience 10, 1003-1011 (2007).
39. Shiraishi & Ascoli, Endocrinology 148, 3214-3225 (2007).
40. McGee & Narayan, Endocrinology 154, 3900-3913 (2013).
41. Zsebo, et al., Proc Natl Acad Sci USA 89, 9464-9468 (1992).
42. Essers, et al., Nature 458, 904-908 (2009).
43. Doan, et al., Epidermal growth factor regulates hematopoietic regeneration after radiation injury. Nat Med (2013).
44. Yu, et al., Stem Cells 24, 876-888 (2006).
45. Opferman, et al., Science 307, 1101-1104 (2005).
46. Qing, et al., Blood 123, 1002-1011 (2014).
47. Randall & Weissman, Blood 89, 3596-3606 (1997).
48. Hai, et al., Biology of reproduction 93, 16 (2015).
49. Tsai, et al., Nature cell biology 15, 309-316 (2013).
50. Jo, et al., J Clin Invest 105, 101-111 (2000).
51. Itoh, et al Experimental hematology 17, 145-153 (1989).
52. Radtke, et al., Exp Hematol 44, 502-507 (2016).

What is claimed is:

1. A chimeric antigen receptor (CAR) comprising an extracellular domain linked to an intracellular signaling domain through a transmembrane domain wherein the extracellular domain comprises a luteinizing hormone (LH) alpha subunit and a LH beta subunit,
  wherein the LH alpha subunit comprises the sequence set forth in SEQ ID NO: 23 or a sequence having at least 90% sequence identity to the sequence set forth in SEQ ID NO: 23 and the LH beta subunit comprises the sequence set forth in SEQ ID NO: 22 or a sequence having at least 90% sequence identity to the sequence set forth in SEQ ID NO: 22 or
  the LH alpha subunit comprises the sequence set forth in SEQ ID NO: 11 or a sequence having at least 90% sequence identity to the sequence set forth in SEQ ID NO: 11 and the LH beta subunit comprises the sequence set forth in SEQ ID NO: 9 or a sequence having at least 90% sequence identity to the sequence set forth in SEQ ID NO: 9,
  and wherein the LH alpha subunit and the LH beta subunit bind the LH receptor.

2. The CAR of claim 1, wherein the LH alpha subunit and the LH beta subunit are linked by a sequence set forth in SEQ ID NO: 10 or a sequence having at least 90% sequence identity to the sequence set forth in SEQ ID NO: 10.

3. The CAR of claim 1, wherein the intracellular signaling domain comprises a CD3 zeta sequence set forth in SEQ ID NO: 27 or SEQ ID NO: 16.

4. The CAR of claim 1, comprising
  the sequence set forth in SEQ ID NO: 20 or a sequence having at least 90% sequence identity to SEQ ID NO: 20 or
  the sequence set forth in SEQ ID NO: 7 or a sequence having at least 90% sequence identity to SEQ ID NO: 7.

5. The CAR of claim 1, further comprising a tag sequence within the extracellular domain.

6. The CAR of claim 5, wherein the tag sequence comprises Myc tag, Strep tag, His tag, Flag tag, Xpress tag, Avi tag, Calmodulin tag, Polyglutamate tag, HA tag, or V5 tag.

7. An immune cell expressing a CAR of claim 1.

8. The immune cell of claim 7, wherein the immune cell is a pHSC, HSC, T cell or NK cell.

9. The CAR of claim 1, wherein the extracellular domain further comprises a CD28 hinge sequence.

10. The CAR of claim 1, wherein the transmembrane domain comprises a CD28 transmembrane domain sequence.

11. The CAR of claim 10, wherein the CD28 transmembrane domain sequence comprises the sequence set forth in SEQ ID NO: 25.

12. The CAR of claim 1, wherein the intracellular signaling domain comprises a 4-1BB sequence.

13. The CAR of claim 12, wherein the 4-1BB sequence comprises the sequence set forth in SEQ ID NO: 26.

14. The CAR of claim 1, wherein the intracellular signaling domain comprises a CD3 zeta sequence.

15. The CAR of claim 1, wherein the intracellular signaling domain comprises a CD28 cytoplasmic sequence.

16. The CAR of claim 1, wherein the intracellular signaling domain comprises a CD3 zeta sequence.

17. The CAR of claim 1, further comprising a linker within the extracellular domain that is 16 amino acids or less.

18. The CAR of claim 17, wherein the linker is a Gly-Ser linker.

19. The CAR of claim 18, wherein the Gly-Ser linker comprises the sequence set forth in SEQ ID NO: 10.

* * * * *

UNITED STATES PATENT AND TRADEMARK OFFICE
CERTIFICATE OF CORRECTION

| | | |
|---|---|---|
| PATENT NO. | : 11,786,557 B2 | Page 1 of 1 |
| APPLICATION NO. | : 16/753277 | |
| DATED | : October 17, 2023 | |
| INVENTOR(S) | : Jarrod Dudakov et al. | |

It is certified that error appears in the above-identified patent and that said Letters Patent is hereby corrected as shown below:

On the Title Page

After "item (73) Assignee," add --MEMORIAL SLOAN-KETTERING CANCER CENTER, New York, NY (US)-- after "Fred Hutchinson Cancer Center, Seattle, WA (US)"

Signed and Sealed this
Thirteenth Day of February, 2024

Katherine Kelly Vidal
*Director of the United States Patent and Trademark Office*